(12) United States Patent
Ecker et al.

(10) Patent No.: US 6,770,738 B1
(45) Date of Patent: Aug. 3, 2004

(54) HIGHER ORDER STRUCTURE AND BINDING OF PEPTIDE NUCLEIC ACIDS

(75) Inventors: David J. Ecker, Leucadia, CA (US); Ole Buchardt, Vaerlose (DK); Michael Egholm, Fredriksberg (DK); Peter E. Nielsen, Hjortevanget 509, DK 2980 Koddedal (DK); Rolf H. Berg, Rungsted Kyst (DK); Niels E. Mollegaard, Virum (DK)

(73) Assignees: ISIS Pharmaceuticals, Inc., Carlsbad, CA (US); Peter E. Nielsen (DK)

( * ) Notice: Subject to any disclaimer, the term of this patent is extended or adjusted under 35 U.S.C. 154(b) by 0 days.

(21) Appl. No.: 09/442,054

(22) Filed: Nov. 16, 1999

Related U.S. Application Data

(60) Division of application No. 08/471,907, filed on Jun. 7, 1995, now Pat. No. 5,986,053, which is a continuation-in-part of application No. 08/054,363, filed on Apr. 26, 1993, now Pat. No. 5,539,082, which is a continuation-in-part of application No. PCT/EP92/01219, filed on May 19, 1992.

(51) Int. Cl.[7] .......................... A61K 38/00; C12Q 1/68; A01N 37/18; A01N 43/04; C07K 1/00
(52) U.S. Cl. .............................. 530/300; 435/6; 514/2; 514/44; 530/333; 530/350
(58) Field of Search ................................. 530/300, 333, 530/350; 435/6; 514/2, 44; 536/23.1

(56) References Cited

U.S. PATENT DOCUMENTS

| | | | |
|---|---|---|---|
| 5,134,066 A | | 7/1992 | Rogers et al. ................. 435/91 |
| 5,539,082 A | * | 7/1996 | Nielsen et al. ............... 530/300 |
| 5,641,625 A | | 6/1997 | Ecker et al. ..................... 435/6 |
| 5,719,262 A | * | 2/1998 | Buchardt et al. ............ 530/300 |
| 5,773,571 A | * | 6/1998 | Nielsen et al. ............... 530/300 |
| 5,837,459 A | * | 11/1998 | Berg et al. ....................... 435/6 |
| 5,986,053 A | * | 11/1999 | Ecker et al. .................. 530/350 |
| 6,228,982 B1 | * | 5/2001 | Norden et al. ............... 530/300 |

FOREIGN PATENT DOCUMENTS

| WO | WO 92/20702 | 11/1992 |
|---|---|---|
| WO | WO 92/20703 | 11/1992 |

OTHER PUBLICATIONS

Demidov, V. et al., "Sequence selective double strand DNA cleavage by Peptide Nucleic Acid (PNA) targeting using nuclease S1", *Nucl. Acids Res.*, 1993, 21(19), 2103–2107.

Depto, A.S. et al., "Regulated Expression of the Human Cytomegalovirus pp65 Gene: Octamer Sequence in the Promoter is Required for Activation by Viral Gene Products", *J. Virology*, 1989, 63, 1232–1238.

(List continued on next page.)

*Primary Examiner*—Ardin H. Marschel
(74) *Attorney, Agent, or Firm*—Woodcock Washburn LLP

(57) ABSTRACT

Peptide nucleic acids and analogues of peptide nucleic acids are used to form duplex, triplex, and other structures with nucleic acids and to modify nucleic acids. The peptide nucleic acids and analogues thereof also are used to modulate protein activity through, for example, transcription arrest, transcription initiation, and site specific cleavage of nucleic acids.

9 Claims, 40 Drawing Sheets

OTHER PUBLICATIONS

Dubochet, J. et al., "A New Preparation Method for Dark–Field Electron Microscopy of Biomacromolecules", *J. Ultrastructure Res.*, 1971, 35, 147–167.

Egholm, M. et al., "Peptide Nucleic Acids (PNA). Oligonucleotide Analogues with an Achiral Peptide Backbone", *J. Am. Chem Soc.*, 1992, 114, 1895–1897.

Egholm, M. et al., "Peptide Nucleic Acids containing Adenine or Guanine recognize Thymine and Cytosine in Complementary DNA Sequences", *J. Chem. Soc. Chem. Comm.*, 1993, 800–801.

Froehler, B.C. et al., "Oligodeoxynucleotides Containing C–5 Propyne Analogs of 2'–Deoxyuridine and 2'–Deoxycytidine", *Tetrahedron Letts.*, 1992, 33, 5307–5310.

Hahn, B.H. et al., "Molecular cloning and characterization of the HTLV–III virus associated with AIDS", *Nature*, 1984, 312, 166–169.

Lal, B. et al., "Diphenylphosphoryl Azide: A Novel Reagent for the Stereospecific Synthesis of Azides from Alcohols", *Tetrahedron Letts.*, 1977, 23, 1977–1980.

McCurdy, S. et al., "Deoxyoligonucleotides with Inverted Polarity: Synthesis and use in Triple–helix Formation", *Nucleosides & Nucleotides*, 1991, 10, 287–290.

Nielsen, P.E. et al., "Sequence–Selective Recognition of DNA by Strand Displacement with a Thymine–Substituted Polyamide", *Science*, 1991, 254, 1497–1500.

Sagi et al., "Base–Modified Oligodeoxynucleotides. I. Effect of 5–Alkyl,5–(1–Alkenyl) and 5–(1–Alkynyl) Substitution of the Pyrimidines on Duplex Stability and Hydrophobicity", *Tetrahedron Letters*, 1993, 34, 2191–2194.

Spalholz, B.A. et al., "Bovine Papillomavirus Transcriptional Regulation: Localization of the E2–Responsive Elements of the Long Control Region", *J. Virology*, 1987, 61, 2128–2137.

Stenberg, R.M. et al., "Promoter–Specific trans Activation and Repression by Human Cytomegalovirus Immediate–Early Proteins Involves Common and Unique Protein Domains", *J. Virology*, 1990, 64, 1556–1565.

Tibanyenda, N. et al., "The effect of single base–pair mismatches on the duplex stability of d(T–A–T–T–A–A–T–A–T–C–A–A–G–T–T–G) d(C–A–A–C–T–T–G–A–T–A–T–T–A–A–T–A)", *Eur. J. Biochem.*, 1984, 139, 19–27.

Vasseur, J.J. et al., "Oligonucleosides: Synthesis of a Novel Methylhydroxylamine–linked Nucleoside Dimer and Its Incorporation into Antisense Sequences", *J. Am. Chem. Soc.*, 1992, 114, 4006–4007.

Vickers, T. et al., "Inhibition of HIV–LTR gene expression by oligonucleotides targeted to the TAR element", *Nuc. Acids. Res.*, 1991, 19, 3359–3368.

Almarsson, Ö. et al., "Molecular mechanics calculations of the structure of polyamide nucleic acid DNA duplexes and triple helical hybrids", *Proc. Natl. Acad. Sci.*, 1993, 90, 7518–7522.

Almarsson, O. et al., "Peptide Nucleic Acid (PNA) Conformation and Polymorphism in PNA–DNA and PNA–RNA hybrids," *Proc. Natl. Acad. Sci. USA*, 1993, 90(20), 9542–9546.

Brown et al., "NMR Solution Structure of a Peptide Nucleic Acid Complex with RNA," *Science*, 1994, 265, 777–780.

Chen et al., "Molecular Dynamics and NMR Studies of Single–Stranded PNA's," *Tetrahedron Lett.*, 1994, 35(29), 5150–5108.

Demidov, V.V. et. al., "Stability of peptide nucleic acids in human serum and cellular extracts", *Biochem. Pharmacol.*, 1994, 48(6), 1309–1313.

Dueholm, K.L. et al., "An Efficient Synthesis of BOC–Aminoacetaldehyde and its Application to the Synthesis of N–(2–BOC–Aminoethyl)Glycine Esters", *Organic Prep. & Proc.*, 1993, 25, 457–461.

Dueholm, K.L. et al., "Peptide Nucleic Acid (PNA) with a Chiral Backbone Based on Alanine", *Biorg. Med. Chem. Letts.*, 1994, 4, 1077–1080.

Dueholm, K.L. et al., "Synthesis of Peptide Nucleic Acid Monomers Containing the Four Natural Nucleobases: Thymine, Cytosine, Adenine, and Guanine and Their Oligomerization", *J. Org. Chem.*, 1994, 59, 5767–5773.

Egholm, M. et al., "Recognition of Guanine and Adenine in DNA by Cytosine and Thymine Containing Peptide Nucleic Acids (PNA)", *J. Am. Chem Soc.*, 1992, 114, 9677–9678.

Flam, F., "Can DNA Mimics Improve On the Real Thing?", *Science*, 1993, 262, 1647–1649.

Frank–Kamenetskii, M., "A Change of Backbone" *Nature* 1991, 354, 505.

Griffith et al, "Single and Bis Peptide Nucleic Acids as Triplexing Agents: Binding and Stoichiometry," *J. Am. Chem. Soc.*, 1995, 117(2), 831–832.

Hyrup, B. et al., "Modification of the Binding Affinity of Peptide Nucleic Acids (PNA). PNA with Extended Backbones consisting of 2–Aminoethyl–B–alanine or 3–Aminopropylglycine Units," *J. Chem. Soc. Chem. Commun.*, 1993, 518–519.

Hyrup et al., "Structure–activity Studies of the Binding of Modified Peptide Nucleic Acids (PNA) to DNA," *J. Am. Chem. Soc.*, 1994, 116(18), 7964–7970.

Kosynkina, L. et al., "A Convenient Synthesis of Chiral Peptide Nucleic Acid (PNA) Monomers", *Tetrahedron Letts.*, 1994, 35, 5173–5176.

Lagriffoul, P.H. et al., "The Synthesis, Co–Oligomerization and Hybridization of a Thymine–Thymine Heterodimer Containing PNA", *Bioorg. Med. & Chem. Letts.*, 1994, 4, 1081–1082.

Leijon et al., "Structural Characterization of PNA–DNA Duplexes by NMR. Evidence for DNA in a B–like Conformation," *Biochemistry*, 1994, 33(33), 9820–9825.

Mollegaard et al., "Peptide Nucleic Acid–DNA Strand Displacement Loops as Artificial Transcription Promoters," *Proc. Natl. Acad. Sci. USA*, 1994, 91(9), 3892–3895.

Nielsen et al., "Peptide Nucleic Acids (PNA). Potential Anti–Sense and Anti–Gene Agents," *Anticancer Drug Des.*, 1993, 8(1), 53–63.

Nielsen, P.E., "Peptide Nucleic Acids (PNA): Potential Antiviral Agents," *Int'l. Antiviral News*, 1993, 1, 37–39.

Nielsen et al., "Peptide Nucleic Acids (PNA). DNA Analogues with a Polyamide Backbone," *Antisense Research and Applications, CRC Press*, 1993, p. 363–373.

Nielsen, P.E., "Peptide Nucleic Acid (PNA): A Model Structure for the Primordial Genetic Material," *Orig. Life Evol. Biosph.*, 1993, 23(5–6), 323–327.

Nielsen et al., "Peptide Nucleic Acid (PNA). A DNA Mimic with a Peptide Backbone," *Bioconjugate Chem.*, 1994, 5(1), 3–7.

Nielsen et al., "Sequence–specific Transcription Arrest by Peptide Nucleic Acid Bound to the DNA Template Strand," *Gene*, 1994, 149(1), 139–145.

Orum et al., "Single Base Pair Mutation Analysis by PNA Directed PCR Clamping", *Nucleic Acids Res.*, 1993, 21(23), 5332–5336.

Peffer et al., "Strand–Invasion of Duplex DNA by Peptide Nucleic Acid Oligomers," *Proc. Natl. Acad. Sci. USA*, 1993, 90(22), 10648–10652.

Rose, D.J., "Characterization of Antisense Binding Properties of Peptide Nucleic Acids By Capillary Gel Electrophoresis," *Anal. Chem.*, 1993, 65(24), 3545–3549.

Wittung et al., "DNA–like Double Helix Formed by Peptide Nucleic Acid," *Nature*, 1994, 368, 561–563.

\* cited by examiner

PNA/DNA   0   0.006  0.02  0.06  0.2  0.6

PNA Target

```
5'------GGATCCAAAAAAAAAAGGATCC-------
3'------CCTAGGTTTTTTTTTTCCTAGG-------
       ‾‾‾‾‾‾              ‾‾‾‾‾‾
       BamH1               BamH1
```

```
PNA   - - -  1  1  10 10
      P B X  P  X  P  X
      1 2 3  4  5  6  7
```

← PvuII

← XbaI

← BamHI 1 2 3 4

XbaI

ARREST

HIGHER ORDER STRUCTURE AND BINDING OF PEPTIDE NUCLEIC ACIDS

CROSS-REFERENCE TO RELATED APPLICATIONS

This patent application is a divisional of application Ser. No. 08/471,907, filed Jun. 7, 1995, now U.S. Pat. No. 5,986,053, which is a continuation-in-part of patent application Ser. No. 08/054,363, filed Apr. 26, 1993, now U.S. Pat. No. 5,539,082, which is a continuation-in-part of application PCT EP92/01219, filed May 19, 1992 and published Nov. 26, 1992 as WO 92/20702. This patent application is related to application Ser. No. 08/088,661, filed Jul. 2, 1993, now U.S. Pat. No. 6,228,982. The entire contents of each of the foregoing patent applications are incorporated herein by reference.

FIELD OF THE INVENTION

This invention is directed to compounds that form triple-stranded structures with single-stranded and double-stranded nucleic acids. It is further directed to the use of such compounds to cause strand displacement in double-stranded nucleic acids. The invention further is directed to processes for modifying double-stranded nucleic acid utilizing such strand displacement. Such processes for modifying double-stranded nucleic acids include cleavage of the nucleic acid strand or strands. In particular, such cleavage includes sequence specific cleavage of double-stranded nucleic acids using a nuclease which normally is nonsequence specific. Such process also include transcription inhibition or arrest as well as transcription initiation. The processes of the invention are effected, in particular, with compounds that include naturally-occurring nucleobases or other nucleobase-binding moieties covalently bound to a polyamide backbone.

BACKGROUND OF THE INVENTION

The function of a gene starts by transcription of its information to a messenger RNA (mRNA) which, by interaction with the ribosomal complex, directs the synthesis of a protein coded for by the mRNA sequence. The synthetic process is known as translation. Translation requires the presence of various co-factors and building blocks, the amino acids, and their transfer RNAs (tRNA), all of which are present in normal cells.

Transcription initiation requires specific recognition of a promoter DNA sequence by the RNA-synthesizing enzyme, RNA polymerase. In many cases in prokaryotic cells, and probably in all cases in eukaryotic cells, this recognition is preceded by sequence-specific binding of a protein transcription factor to the promoter. Other proteins which bind to the promoter, but whose binding prohibits action of RNA polymerase, are known as repressors. Thus, gene activation typically is regulated positively by transcription factors and negatively by repressors.

Most conventional drugs function by interaction with and modulation of one or more targeted endogenous proteins, e.g., enzymes. Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug necessary likely could be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Synthetic reagents that bind sequence selectively to single-stranded and especially to double-stranded nucleic acids are of great interest in molecular biology and medicinal/chemistry, since such reagents may provide the tools for developing gene-targeted drugs and other sequence-specific gene modulators. Until now oligonucleotides and their close analogues have presented the best candidates for such reagents.

Oligodeoxyribonucleotides as long as 100 base pairs (bp) are routinely synthesized by solid phase methods using commercially available, fully automatic synthesis machines. Oligoribonucleotides, however, are much less stable than oligodeoxyribonucleotides, a fact which has contributed to the more prevalent use of oligodeoxyribonucleotides in medical and biological research directed to, for example, gene therapy and the regulation of transcription and translation. Synthetic oligodeoxynucleotides are being investigated for used as antisense probes to block and eventually breakdown mRNA.

It also may be possible to modulate the genome of an animal by, for example, triple helix formation using oligonucleotides or other DNA recognizing agents. However, there are a number of drawbacks associated with oligonucleotide triple helix formation. For example, triple helix formation generally has only been obtained using homopurine sequences and requires unphysiologically high ionic strength and low pH. Whether used as antisense reagents or a triplexing structures, unmodified oligonucleotides are unpractical because they have short in vivo half-lives. To circumvent this, oligonucleotide analogues have been used.

These areas for concern have resulted in an extensive search for improvements and alternatives. For example, the problems arising in connection with double-stranded DNA (dsDNA) recognition through triple helix formation have been diminished by a clever "switch back" chemical linking whereby a sequence of polypurine on one strand is recognized, and by "switching back", a homopurine sequence on the other strand can be recognized. See, e.g., McCurdy, Moulds, and Froehler, *Nucleosides,* in press. Also, helix formation has been obtained by using artificial bases, thereby improving binding conditions with regard to ionic strength and pH.

In order to improve half-life as well as membrane penetration, a large number of variations in polynucleotide backbones has been undertaken. These variations include the use of methylphosphonates, monothiophosphates, dithiophosphates, phosphoramidates, phosphate esters, bridged phosphoramidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives. The great majority of these backbone modifications have decreased the stability of hybrids formed between a modified oligonucleotide and its complementary native oligonucleotide, as assayed by measuring $T_m$ values. Consequently, it is generally believed in the art that backbone modifications destabilize such hybrids, i.e., result in lower $T_m$ values, and should be kept to a minimum.

The discovery of sequence specific endonucleases (restriction enzymes) was an essential step in the development of biotechnology, enabling DNA to be cut at precisely specified locations containing specific base sequences. However, although the range of restriction enzymes now known is extensive, there is still a need to obtain greater flexibility in the ability to recognize particular sequences in double-stranded nucleic acids and to cleave the nucleic acid specifically at or about the recognized sequence.

Most restriction enzymes recognize quartet or sextet DNA sequences and only a very few require octets for recognition. However, restriction enzymes have been identified and isolated only for a small subset of all possible sequences within these constraints. A need exists, especially in connection with the study of large genomic DNA molecules, in general, and with the human genome project, in particular, to recognize and specifically cleave DNA molecules at more rarely occurring sites, e.g., sites defined by about fifteen base pairs.

Efforts have therefore been made to create artificial "restriction enzymes"or to modify the procedures for using existing restriction enzymes for this purpose. Methods investigated include the development of oligonucleotides capable of binding sequence specifically via triple helix formation to double-stranded DNA tagged with chemical groups (e.g., photochemical groups) able to cleave DNA or with non-specific DNA cleaving enzymes and other such modifications consistent with an "Achilles heel" general strategy. Such methods are described by: Francois, J. C., et al. PNAS 86,9702–9706 (1989); Perrouault, L., et al. Nature 344,358–360 (1990); Strobel, S. A. & Dervan P. B. Science 249,73–75 (1990); Pei, D., Corey D. R. & Schultz P. G. PNAS 87,9858 (1990); Beal, P. A. & Dervan P. B., Science 251,1360 (1991); Hanvey, J. C., Shimizu M. & Wells R. D. NAR 18,157–161 (1990); Koob, H. & Szybalski W. Science 250,271 (1990); Strobel, S. A. & Dervan P. B. Nature #50,172 (1991); and Ferrin, L. J. & Camerini-Otero R. D. Science 254,1494–1497 (1991).

In Patent Cooperation Treaty Applications No. PCT/EP92/01220, and PCT/EP92/01219, both filed on 22nd May 1992, we described certain nucleic acid analogue compounds that have a strong sequence specific DNA binding ability. Examples of such compounds were also disclosed by us in Science 1921, 254 1497–1500. We have shown that a nucleic acid analogue of this type containing 10 bases hybridized to a non-terminal region of a double-stranded DNA and rendered the strand of DNA which was non-complementary to the nucleic acid analogue susceptible to degradation by $S_1$ nuclease. No increased cleavage of the DNA strand complementary to the nucleic acid analogue was seen, so no cleavage of double-stranded DNA was obtained.

OBJECT OF THE INVENTION

It is an object of the invention to provide compounds that bind DNA and RNA strands.

It is a further object of the invention to provide triple x structures between DNA or RNA strands and these compounds.

It is yet another object to provide compounds other than RNA that can bind on strand of a double-stranded polynucleotide, thereby displacing the other strand.

It is still another object to provide therapeutic, diagnostic, and prophylactic methods that employ such compounds.

BRIEF DESCRIPTION OF THE INVENTION

In the cell, DNA exists as a double stranded structure. During certain cellular events, as for instance transcription or during cell division, portions of the double stranded DNA are transiently denatured to single strand. Further DNA can be isolated outside of a cell and can be purposefully denatured to single stranded DNA. RNA generally exist as a single stranded structure; however, in a local area of secondary structure a RNA, as for instance the stem of a stem loop structure, the RNA can exist as a double stranded structure.

We have found that certain compounds that have nucleobases attached to an aminoethylglycine backbone and other like backbones including polyamides, polythioamides, polysulfinamides and polysulfonamides, which compounds we call peptide nucleic acids or PNA, surprisingly bind strongly and sequence selectively to both RNA and DNA.

We have surprisingly found that these PNA compounds recognize and bind sequence-selectively and strand-selectively to double-stranded DNA (dsDNA). We have found that the binding to double-stranded DNA is accomplished via strand displacement, in which the PNA binds via Watson-Crick binding to its complementary strand and extrudes the other strand in a virtually single-stranded conformation. We have also surprisingly found that these PNA compounds recognize and bind sequence-selectively to single-stranded DNA (ssDNA) and to RNA.

The recognition of PNA to RNA, ssDNA or dsDNA can take place in sequences at least 5 bases long. A more preferred recognition sequence length is 5–60 base pairs long. Sequences between 10 and 20 bases are of particular interest since this is the range within which unique DNA sequences of prokaryotes and eukaryotes are found. Sequences of 17–18 bases are of special interest since this is the length of unique sequences in the human genome.

We have further surprisingly found that the PNA compounds are able to form triple helices with dsDNA. We have found that PNA compounds are able to form triple helices with RNA and ssDNA. The resulting triplexes, e.g., $(PNA)_2$/DNA or $(PNA)_2$/RNA, surprisingly have very high thermal stability. It has been found that the PNA binds with a DNA or RNA in either orientation, i.e., the antiparallel orientation where the amino-terminal of the PNA faces the 3' end of the nucleic acid or the parallel orientation where the amino-terminal of the PNA faces the 5' end of the nucleic acid. PNAs are able to form triple helices wherein a first PNA strand binds with RNA or ssDNA and a second PNA strand binds with the resulting double helix or with the first PNA strand.

We further have found that the PNA compounds are able to form triple helices wherein a first PNA strand binds with the ssDNA or RNA or to one of the strands of dsDNA and in doing so displaces the other strand, and a second PNA strand then binds with the resulting double helix. While we do not wish to be bound by theory, it is further believed that other triple helices might be formed wherein a single PNA strand binds to two single stranded nucleic acids strands. In binding with nucleic acids both Watson-Crick and Hoogsteen bind is utilized. It is further believed that PNA might also bind via reverse Hoogsteen binding.

We have further surprisingly found that the PNA compounds form double helices with RNA and ssDNA. Such double helices are hetero duplex structures between the PNA and the respective nucleic acid. Such double helices are preferably helices formed when the PNA strand includes a mixture of both pyrimidine and purines nucleobases.

For therapeutic use of PNA compounds the targets of the PNA compounds would generally be double stranded DNA and RNA. For diagnostic use, investigations methods and reagents where DNA is isolated outside of a cell, the DNA can be denatured to single stranded DNA and use of the PNA compound would be targeted to such single stranded DNA as well as RNA.

PNA compounds useful to effect binding to RNA, ssDNA and dsDNA and to form duplex and triplex complexes are in one sense polymeric strands formed from a polyamide, polythioamide, polysulfinamide or polysulfonamide backbone with a plurality of ligands located at spaced locations along the backbone. At least some of the ligands are capable of hydrogen bonding with other ligands either on the compounds or nucleic acid ligands.

More preferred PNA compounds according to the invention have the formula:

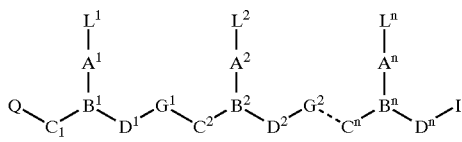

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands;

each of $C^1$–$C^n$ is ($CR^6R^7$), where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^6$ and $R^7$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is ($CR^6R^7$) where $R^5$ and $R^7$ are as defined above;

each of y and z is zero or an integer from 1 to 10, the sum y+z being greater than 2 but not more than 10;

each of $G^1$–$G^n$ is —$NR^3CO$—, —$NR^3CS$—, —$NR^3SO$— or —$NR^3SO_2$—, in either orientation, where $R^3$ is as defined above;

each of $A^1$–$A^n$ and $B^1$–$B^n$ are selected such that:
(a) A is a group of formula (IIa), (IIb), (IIc) or (IId), and B is N or $R^3N^4$; or
(b) A is a group of formula (IId) and B is CH;

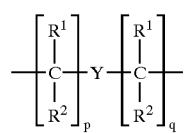

(IIa)

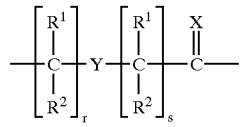

(IIb)

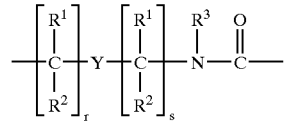

(IIc)

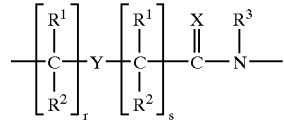

(IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and each $R^3$ and $R^4$ is independently selected from the group consisting of hydrogen, ($C_1$–$C_6$)alkyl, hydroxy- or alkoxy- or alkylthio-substituted ($C_1$–$C_6$)alkyl, hydroxy, alkoxy, alkylthio and amino;

Q is —$CO_2H$, —$CONR'R''$, —$SO_3H$ or —$SO_2NR'R''$ or an activated derivative of —$CO_2H$ or —$SO_3H$; and I is —$NHR'''R''''$ or —$NR'''C(O)RI''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

In the above structures wherein R', R'', R''' and R'''' are oligonucleotides or oligonucleosides, such structures can be considered chimeric structures between PNA compounds and the oligonucleotide or oligonucleoside.

Preferred PNA-containing compounds useful to effect binding to RNA, ssDNA and dsDNA and to form triplexing structure are compounds of the formula III, IV or V:

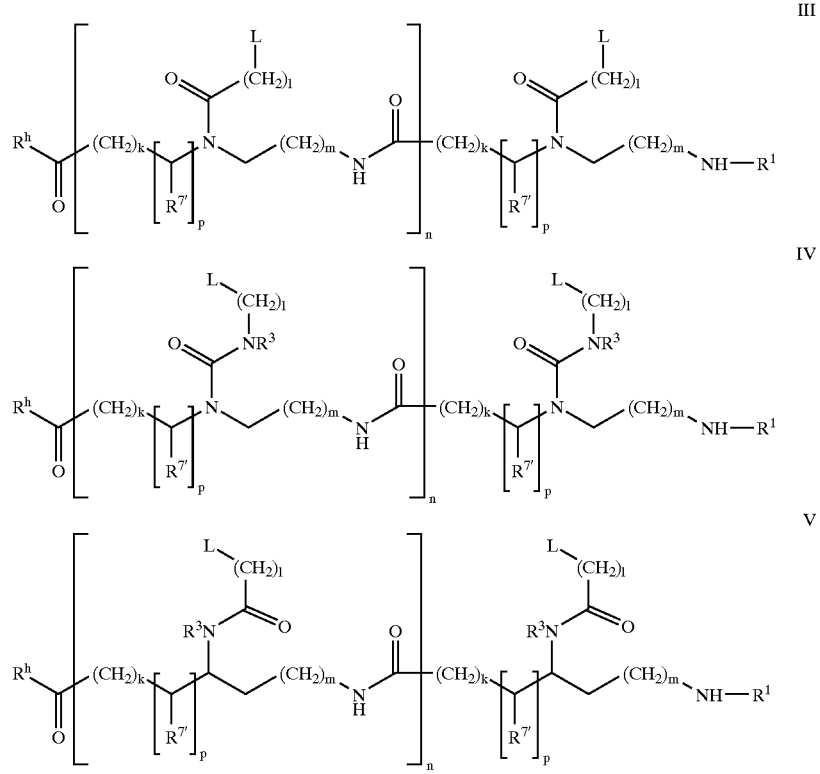

where in:
each L independently selected from the group consisting of hydrogen, phenyl, heterocyclic moieties, naturally occurring nucleobases, and non-naturally occurring nucleobases;
each $R^{7'}$ is independently selected from the group consisting of hydrogen and the side chains of naturally occurring alpha amino acids;
n is an integer greater than 1,
each k, l, and m is, independently, zero or an integer from 1 to 5;
each p is zero or 1;
$R^b$ is OH, $NH_2$ or —$NHLysNH_2$; and
$R^i$ is H or $COCH_3$.

The improved binding of the PNA compounds of the invention with single-stranded RNA and DNA renders them useful as antisense agents. In addition, the binding to double-stranded DNA renders these compounds useful for gene inhibition via various mechanisms. Further, the binding to double-stranded DNA renders these compounds useful as gene activators to initiate transcription.

In one embodiment, the present invention provides methods for inhibiting the expression of particular genes in the cells of an organism, comprising administering to said organism a reagent as defined above which binds specifically to sequences of said genes.

In a further embodiment, the invention provides methods for inhibiting transcription and/or replication of particular genes or for modifying double-stranded DNA as, for instance, by inducing degradation of particular regions of double-stranded DNA in cells of an organism comprising administering to said organism a reagent an defined above.

In a still further embodiment, the invention provides methods for killing cells or virus by contacting said cells or virus with a reagent as defined above which binds specifically to sequences of the genome of said cells or virus.

A novel strategy for sequence-selective cleavage of double-stranded DNA is described. For cases were two closely positioned homo-pyrimidin stretches (of 7–10 bas s and preferably on opposite strands) can be identified, this can be done by synthesizing pairs of PNAs complementary to two parts of this DNA sequence and separated by several base pairs. These PNA molecules are then reacted with the dsDNA and the resulting complex is allowed to react with an endonuclease.

In practicing certain embodiments of the invention, the PNA compounds are able to recognize duplex DNA by displacing one strand, thereby presumably generating a hetero duplex with the other one. Such recognition can take place with dsDNA sequences 5–60 base pairs long. Sequences between 10 and 20 bases are of interest since this is the range within which unique DNA sequences of prokaryotes and eukaryotes are found. Reagents which recognize 17–18 bases are of particular interest since this is the length of unique sequences in the human genome.

The PNA compounds are able to form triple helices with dsDNA, ssDNA or RNA and double helices with RNA or ssDNA. In one embodiment of the invention, the PNA compounds form triple helices wherein a first PNA strand binds with a nucleic acid strand forming a hetero duplex and a second PNA strand then binds with the resulting hetero duplex. In other embodiments of the invention, a PNA compound or a PNA chimera compound forms triple helices wherein a single PNA strand or PNA chimera strand binds with two nucleic acid strands, with a nucleic acid strand and a PNA strand or with two chimera PNA strands.

The invention further provides methods for inhibiting the action of restriction enzymes at restriction sites in nucleic acids. Such methods comprise contacting a nucleic acid with a reagent as defined above under conditions effective to bind such reagent to the nucleic acid proximal to a restriction site.

The invention further provides methods of sequencing DNA by binding the DNA with a reagent as defined above at a site proximal to a restriction site, cleaving the DNA with a restriction enzyme, and identifying the cleaved products.

The invention further provides methods for initiating transcription in cells or organisms comprising administering to the organism a reagent as defined above which initiates transcription of a gene in such cells or organisms.

The invention further provides methods for modulating binding of RNA polymerase to dsDNA by binding the dsDNA with a reagent as defined above that binds with the DNA and then exposing the complex formed thereby to a RNA polymerase.

The invention further provides methods for initiating transcription of a gene by binding the gene with a reagent as defined above that interacts with the gene to melt the double-stranded DNA of the gene and to form a transcription elongation loop.

The invention further provides methods for binding RNA polymerase to dsDNA by contacting the dsDNA with a reagent as defined above that is capable of interacting with the DNA and then exposing the complex formed thereby to a RNA polymerase. More particularly, the interaction is via binding to said dsDNA.

The invention further provides a hybrid complex for modulating transcription wherein the complex comprises dsDNA and a reagent as defined above that binds with the dsDNA, and a RNA transferase.

The invention further provides a synthetic transcription factor comprising a dsDNA and a reagent as defined above that is capable of interaction with the dsDNA. More particularly, the interaction is via binding to said dsDNA.

The invention further provides specific gene activators comprising first and second strands, as defined above, that have specific sequences that bind to selected DNA regions of the gene.

The invention further provides chimeric structures comprising PNAs and DNA or RNA. Such chimeric structures will be used in place of or in addition to a normal PNA strand to effect duplexing, triplexing, nucleic acid binding or protein binding.

BRIEF DESCRIPTION OF THE DRAWINGS

FIG. 5 refers to GGATC-CAAAAAAAAAAGGATCC (SEQ. ID. NO: 60); CCTAG-GTTTTTTTTTTCCTAGG (SEQ. ID. NO: 61) and CCTAGGTTTTTTTTTTCCTAGG (SEQ. ID. NO: 85);

DETAILED DESCRIPTION OF THE INVENTION

For the purposes of this invention the term "purine rich" shall mean a preponderance (I.e., greater than 50%) of purine bases, preferably greater than about 65% and most preferrably greater than about 90%. Further, the term "modify" shall mean to change properties by addition to, subtraction from, cleavage of or otherwise, such that which results is intrinsically different from that which is modified. The term "modulate" shall mean to change (i.e., increase or decrease) the magnitude of a property.

Figure 2:
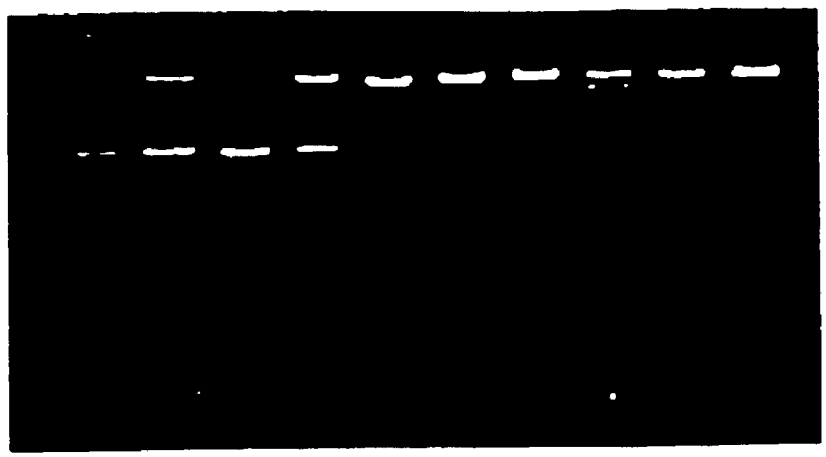
FIG. 2 is an ethidium bromide stained gel showing a similar cleavage of a double-stranded DNA having two closely spaced sites for hybridization to the nucleic acid analogue on the same DNA strand (Example 2)

In accordance with the present inventions, the ligand L is primarily a naturally occurring nucleobase attached at the position found in nature, i.e., position 9 for purines including adenine, guanine or inosine, and position 1 for pyrimidines including thymine, uridine, or cytosine. Alternatively, L may be a non-naturally occurring nucleobase (nucleobase analog), another base-binding moiety, an aromatic moiety, $(C_1-C_6)$alkanoyl, hydroxy or even hydrogen. It will be understood that the term nucleobase includes nucleobases bearing removable protecting groups. Some typical nucleobase ligands and illustrative synthetic ligands are shown in FIG. 2 of WO 92/20702. Two particular nucleobase ligands, 5-propynylthymine and 3-deazauracil, have been shown to increase binding affinity of an oligonucleotide to a target nucleotide (see Froehler, B. C. et. al., *Tetrahedron Letters*, 1992 33:5307–5310 and U.S. Pat. No. 5,134,066). Other like analogues are shown by Sagi, J. et. al., *Tetrahedron Letters*, 1993 34:2191–2194. Incorporation of these nucleobase can be effected to increase the binding affinity of the PNA product with a nucleic acid target. Further useful non-naturally occurring nucleobases include 6-thioguanine, i.e., purine-6(1H)-thione, and pyrazolo[4,3-d]pyrimidines especially useful as triplexing bases (see PCT application PCT/US92/04795).

Figure 4:
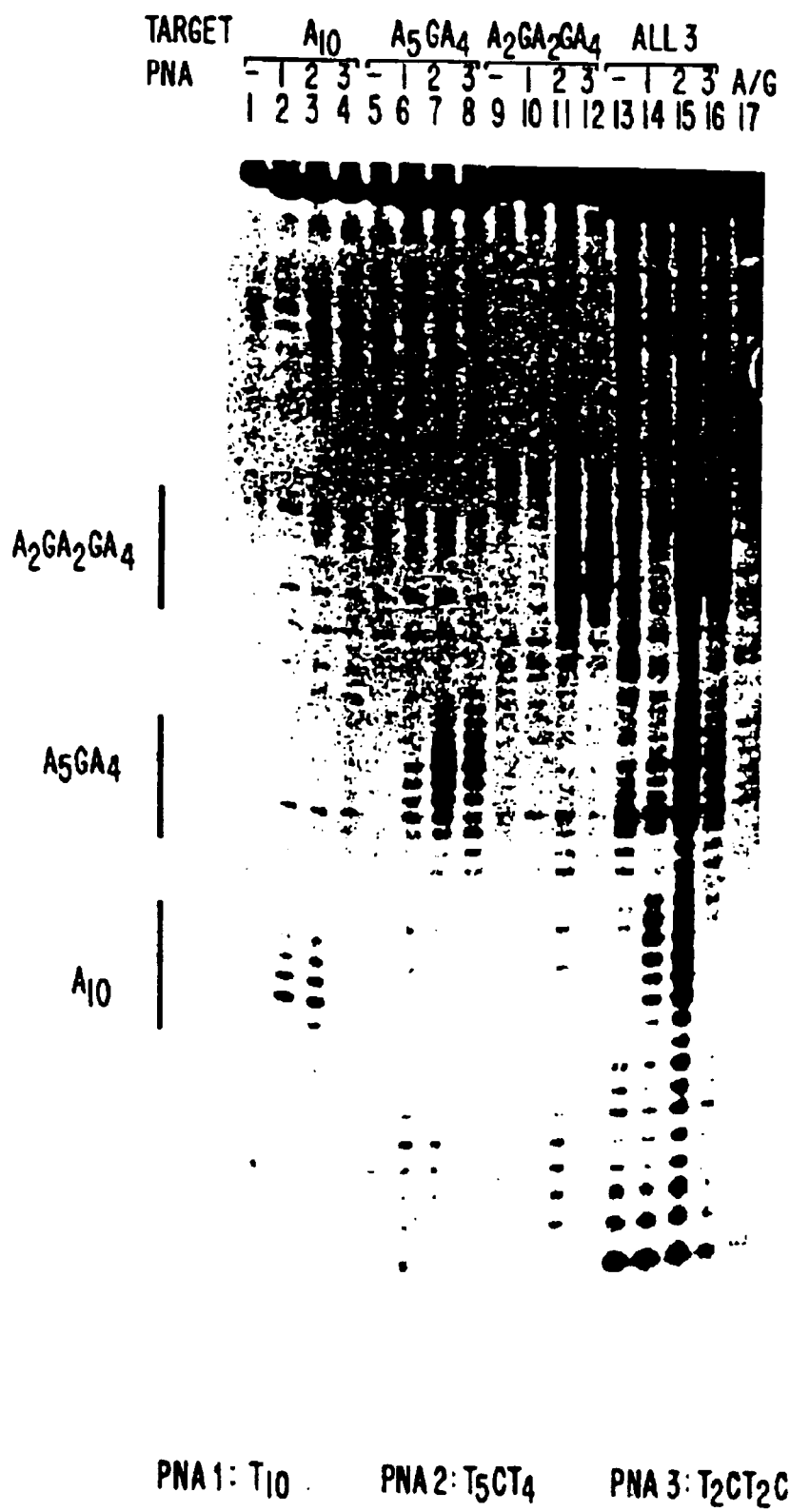
FIG. 4 shows a PAGE autoradiograph demonstrating that PNAs-$T_{10}$ (SEQ ID NO:2), -$T_9C$ and -$T_8C_2$ bind to double-stranded DNA with high sequence specificity.

Furthermore, L can be a DNA intercalator, a reporter ligand such as, for example, a fluorophor, a radio lab 1, a spin label, hapten, or a protein-recognizing ligand such as biotin. In monomer synthons, L may be blocked with protecting groups, as illustrated in FIG. 4 of WO 92/20702.

Linker A can be a wide variety of groups such as —$CR^1R^2CO$—, —$CR^1R^2CS$—, —$CR^1R^2CSe$—, —$CR^1R^2CNHR^3$—, —$CR^1R^2C=CH_3$— and —$CR^1R^2C=C(CH_3)_2$—, where $R^1$, $R^2$ and $R^3$ are as defined above Preferably, A is methylenecarbonyl (—$CH_2CO$—), amido (—$CONR^3$—), or ureido (—$NR^3CONR^3$—). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a $(C_1-C_6)$alkylene chain, a $(C_2-C_6)$alkylene chain substituted with $R^1R^2$ or can be heterogenous, containing Y. In certain cases, A can just be a single bond.

In one preferred form of the invention, B is a nitrogen atom, thereby presenting the possibility of an achiral backbone. B can also be $R^3N^+$, where $R^3$ is as defined above, or CH.

In the preferred form of the invention, C is —$CR^6R^7$—, but can also be a two carbon unit, i.e., —$CHR^6CHR^7$— or —$CR^6R^7CH_2$—, where $R^6$ and $R^7$ are as defined above. $R^6$ and $R^7$ also can be heteroaryl groups such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In the preferred form of the invention, E in the monomer synthon is COOH or an activated derivative thereof, and G in the oligomer is —$CONR^3$— (amide). As defined above, E may also be CSOH, SOOH, $SO_2OH$ or an activated derivative thereof, whereby G in the oligomer becomes —$CSNR^3$—, —$SONR^3$— and —$SO_2NR^3$—, (thioamide, sulfinamide or sulfonamide, respectively). The G group can be in either orientation, e.g., for amide —$CONR_3$— or —$R_3NCO$—. The activation may, for example, be achieved using an acid anhydride or an active ester derivative, wherein hydrogen in the groups represented by E is replaced by a leaving group suited for generating the growing backbone.

The amino acids which form the backbone may be identical or different. We have found that those based on 2-aminoethylglycine are especially well suited to the purpose of the invention.

In some cases it may be of interest to attach ligands at either terminus (Q, I) to modulate the binding characteristics of the PNAs. Representative ligands include DNA intercalators, which improve dsDNA binding or basic groups, such as lysine or polylysine, which strengthen the binding of the PNA due to electrostatic interaction. To decrease electrostatic repulsion charged groups such as carboxyl and sulfo groups could be used. The design of the synthons further all we such other moieties to be located on non-terminal positions. Oligonucleotides and/or oligonucleoside can be covalently bound to terminal positions Q or I to form chimeras containing PNA portions and oligonucleotide and/or oligonucleoside portions. Nucleosides and/or nucleotides (mono, di or tri-phosphates) also can be attached to the terminal positions.

In a further aspect of the invention, the PNA oligomers are conjugated to low molecular weight effector ligands such as ligands having nuclease activity or alkylating activity or reporter ligands (fluorescent, spin labels, radioactive, protein recognition ligands, for example, biotin or haptens). In a further aspect of the invention, the PNAs are conjugated to peptides or proteins, where the peptides have signaling activity and the proteins are, for example, enzymes, transcription factors or antibodies. Also, the PNAs can be attached to water-soluble or water-insoluble polymers. In another aspect of the invention, the PNAs are conjugated to oligonucleotides or carbohydrates. When warranted, a PNA oligomer can be synthesized onto some moiety .(g., a peptide chain, reporter, intercalator or other type of ligand-containing group) attached to a solid support.

Such conjugates can be used for gene modulation (e.g., gene targeted drugs), for diagnostics, for biotechnology, and for scientific purposes.

As a further aspect of the invention, PNAs can be used to target RNA and ssDNA to produce both antisense-type gene regulating moieties and hybridization probes for the identification and purification of nucleic acids. Furthermore, the PNAs can be modified in such a way that they form triple helices with dsDNA. Reagents that bind sequence-specifically to dsDNA have applications as gene targeted drugs. These are foreseen as extremely useful drugs for treating diseases like cancer, AIDS and other virus infections, and may also prove effective for treatment of some genetic diseases. Furthermore, these reagents may be used for research and in diagnostics for detection and isolation of specific nucleic acids.

Triple helix formation, wherein an oligonucleotide is triplexed to a dsDNA, is believed to be the only means known in the art for sequence-specific recognition of dsDNA. However, triple helix formation is largely limited to recognition of homopurine-homopyrimidine sequences. Triplexing with strand displacement using PNAs of this invention is superior to oligonucleotide-dsDNA triple helix recognition in that it may allow for recognition of any sequence by use of the four natural bases.

Gene targeted drugs are designed with a nucleobase sequence (containing 10–20 units) complementary to the regulatory region (the promoter) of the target gene. Upon administration, the drug binds to the promoter and blocks access thereto by RNA polymerase. Consequently, no MRNA, and thus no gene product (protein), is produced. If the target is within a vital gene for a virus, no viable virus particles will be produced. Alternatively, if the target is downstream from the promoter, RNA polymerase will terminate at this position, thus forming a truncated mRNA/protein which is nonfunctional.

Sequence-specific recognition of ssDNA by base complementary hybridization can be exploited to target specific genes and viruses. In this case, the target sequence is contained in the mRNA such that binding of the drug to the target hinders the action of ribosomes and, consequently, translation of the mRNA into protein. The peptide nucleic acids of the invention are superior to prior reagents in that they have significantly higher affinity for complementary SSDNA. Also while a charged species such as a lysine moiety can be added, PNAs possess no charge, they are water soluble (which should facilitate cellular uptake), and they contain amides of non-biological amino acids (which should make them biostable and resistant to enzymatic degradation by, for example, proteases). Further, they can triplex with the mRNA.

The PNA compounds used in this invention can be synthesized by the methodologies disclosed in WO 92/20702, WO/92/20703 and the foregoing United States patent application Ser. No. 08/054,363. Monomer synthons according to those disclosures are coupled using standard protocols to give the desired PNA oligomeric sequences. The synthesis of additional synthetic monomers are given by example 33 through 45 of this specification.

Binding of PNA compounds to double-stranded DNA accompanied by strand displacement is shown in illustrative examples in this specification by both enzymatic and chemical probing. Our illustrative examples show that the PNA compounds bind via Watson-Crick binding to their complementary strand and extrudes the other strand in a virtually single-stranded conformation.

Using the PNA compound to locally unwind the DNA duplex and effect strand displacement can render the displaced DNA strand sensitive to cleavage (e.g., cleavage by $S_1$ nuclease). This gives or induces high yield double strand DNA breaks at the site of PNA binding. PNA-directed and PNA-provoked double strand DNA cleavage by $S_1$ nuclease is especially efficient when two adjacent PNA sites are targeted, yielding guantitative conversion of the target site into double-strand breaks.

As an illustrative example of use as an artificial restriction enzyme, the targets are cloned within a pUC19 polylinker and the plasmids are linearized with the Cfr10I restriction enzyme. In the linear DNA, the resulting polylinker region is in the middle (1.33 kb from one end and 1.36 kb from the other). A pT10 plasmid carrying a known sequence is then inserted in the unique BamHl site in the polylinker. This is complexed with a complementary PNA compound and subjected to treatment with $S_1$ nuclease. Upon nuclease treatment, a significant fraction of DNA is cut, as shown by gel electrophoresis of the resulting fragments. Cross reactivity experiments show that the targeting is sequence-specific; only corresponding PNAs mediated cutting of the targets. The yield of digested molecules is high and one can reach the quantitative digestion with increasing exposure to nuclease.

The results of such treatment demonstrate a novel method for sequence-selective cleavage of double-stranded DNA. If two closely positioned homo-pyrimidine stretches can be identified (as for example 7–10 bases, preferably on opposite strands), this can be done by synthesizing pairs of PNAs complementary to two parts of this DNA sequence and separated by several base pairs. If this strand displacement binding mode is extended to include PNAs recognizing DNA sequences containing thymine and cytosine, this strategy allows targeting and specific cleavage of any desired sequence of 10–20 base pairs. In effecting such cleavage, the high stability of PNA-DNA complexes consisting of two PNA strands (one "Watson-Crick" and one "Hoogsteen") and one DNA strand must be considered, as must the sequence of the "Hoogsteen-like" strand.

We have found that complexes between homopyrimidine PNA and complementary oligonucleotides show 2:1 stoichiometry. Further we have found that the thermal stability of triplexes between cytosine-containing homopyrimidine PNA and complementary oligonucleotides is strongly pH dependent, indicating the involvement of $C^+G$-C Hoogsteen hydrogen bonding in $(PNA)_2$ DNA triplexes. Further, while we do not wish to be bound by any particular theory, we believe that the strand displacement binding of homopyrimidine PNA to dsDNA is dependent on the formation of such (PHA)$_2$/DNA triplexes with the complementary strand of the dsDNA target. It is our present belief that formation of the strand displacement complex proceeds via a DNA/PNA Watson-Crick duplex which is subsequently stabilized by a Hoogsteen bound second strand having C$^+$-G Hoogsteen hydrogen bonds.

Figure 8:
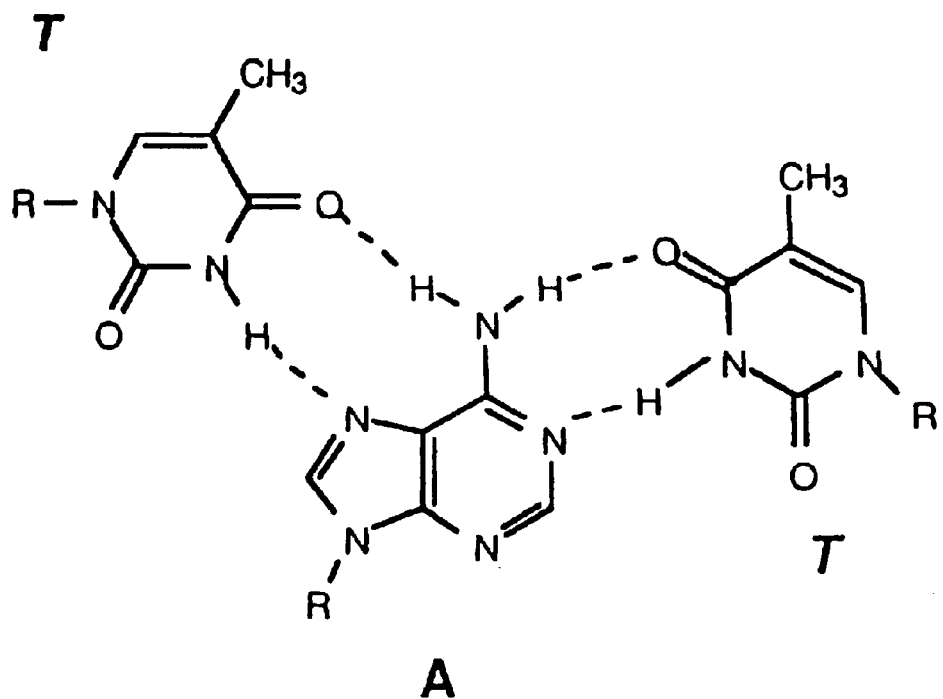
FIG. 8 is a schematic model of $C^+$G-G and T A-T triplets with Hoogsteen and Watson-Crick hydrogen bonds.
Figure 8:
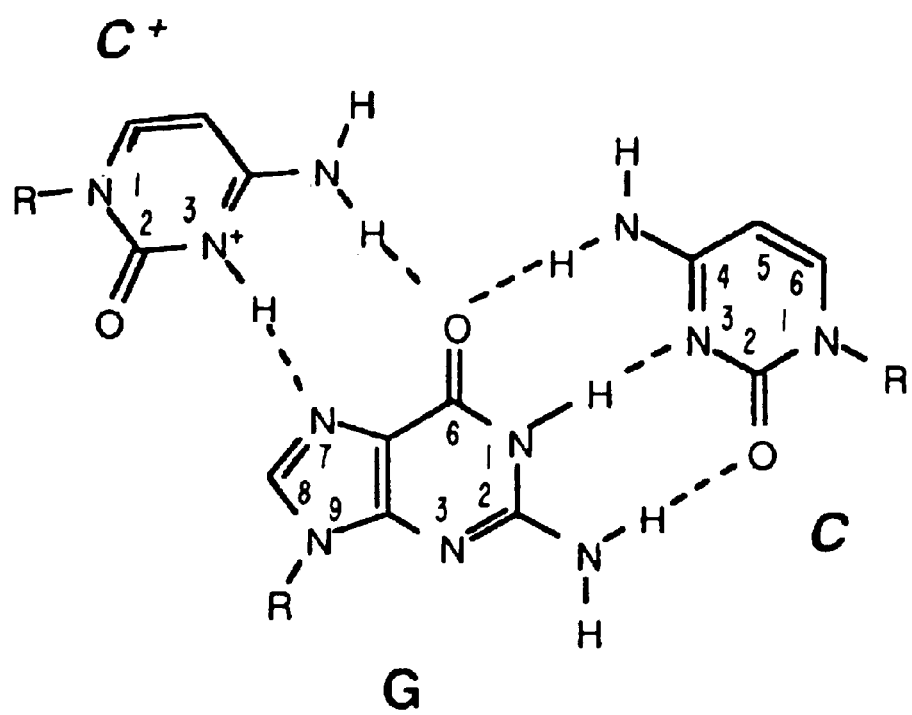
Figure 9:
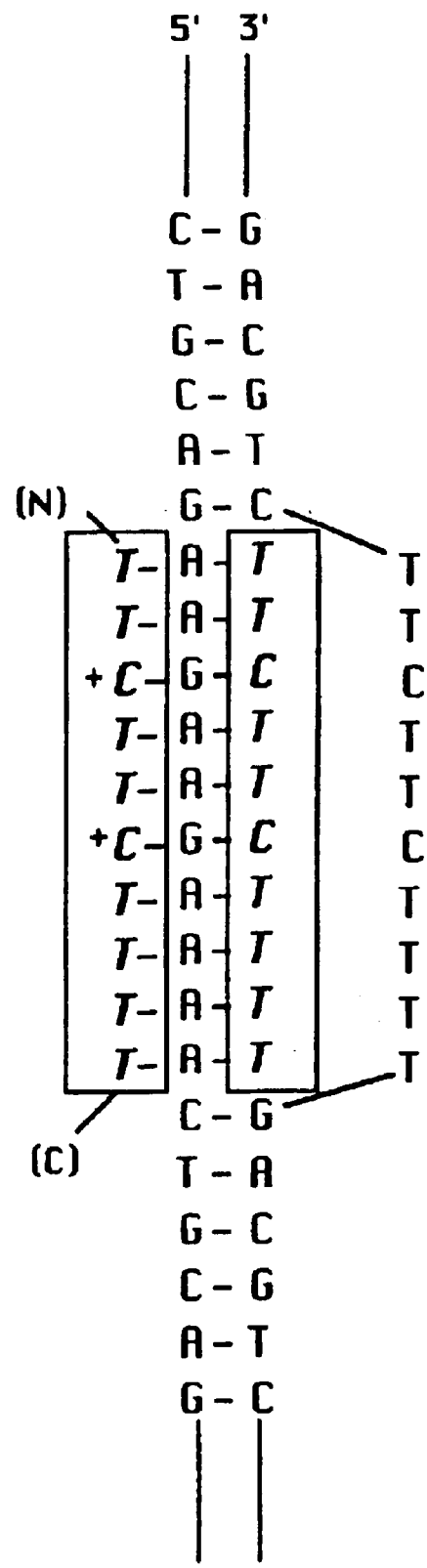
FIG. 9 is a schematic model of the binding of PNA ($T_2CT_2CT_4$) (SEQ ID NO:1) to a double-stranded DNA target.

In further studies of triplexing and strand displacing, we utilized a cytosine containing homopyrimidine PNA (T$_2$CT$_2$CT$_4$-LysNH$_2$; SEQ ID NO:1) and studied its binding to a dimeric target. Stability of the complex was probed by both dimethylsulfate (DMS) probing and KMnO$_4$ probing. In these studies, we found that triple strand formation involve a Hoogsteen hydrogen bonding. This was evidenced by our showing that the N7 atoms of guanines of the target participate in base pairing and, thus, are protected from reaction with DMS upon triplexing binding of the PNA. A model of; this triplexing binding is shown in FIGS. 8 and 9.

We have also used electron microscopy to confirm strand displacement. In these examples, a PNA-DNA complex was formed with a target. Full occupancy of the target resulted in a strand displacement loop of 90–100 bases, as detected by electron microscopy. The DNA molecules carry an open region in the form of an "eye". In all cases, one of the two strands in the open region is thicker than the other one and has the same thickness as the normal DNA duplex. The thicker strand corresponds to the strand covered by PNA while the thinner strand corresponds to the displaced strand. In control experiments carried out without added PNA, the displaced structures are not observed.

Discrimination of PNA compounds in binding to targets was also observed utilizing labeled DNA fragments that were challenged with various PNA compounds. We show that PNA compounds bind with high preference to the complementary target. Binding decreases with increasing mismatches in the targets. Binding to a target containing one mismatch was weaker than for a fully complementary target, while no binding was observed with a two-mismatch target.

We have further found that PNA compounds truly mimic DNA in terms of base pair specific hybridization to complementary strands of oligonucleotides as measured by thermal stability of complexes. We have shown that the formation of PNA/DNA duplexes exhibits a decrease in entropy almost identical to that for the formation of DNA/DNA duplexes and that like the formation of a DNA/DNA it is strongly enthalpy driven. From this we deduce that single stranded PNA must have the same degree of base stacking as single stranded DNA and thus appears to be highly structured. Further we have found that the rate of hybridization of PNA/RNA duplexes is at least as fast as that for 2'-O-methyl RNA/RNA or DNA/DNA duplex formation again supporting our findings that single stranded PNA is at least as prestructured for duplex formation as is DNA or RNA.

We have further found that in contrast to DNA or RNA, PNA compounds may bind to complementary DNA or RNA in one of two orientations, a parallel orientation or an anti-parallel orientation. We have further found that the PNA compounds prefer the anti-parallel orientation (wherein the amino end of the PNA strand is complementary to the 3'-end of the nucleic acid) over the parallel orientation ((wherein the amino end of the PNA strand is complementary to the 5'-end of the nucleic acid).

In our studies we have shown that homo-pyrimidine PNA binds strongly to ssDNA, dsDNA or RNA with 2:1 stoichiometry (triplexing) and effects stable strand displacement complexes with dsDNA. Further, purine-pyrimidine PNA binds to Watson-Crick complementary oligonucleotides, either RNA or DNA, with 1:1 stoichiometry. Utilizing these findings, one embodiment of this invention is directed to use of PNA compounds as effective inhibitors of the elongation activity of RNA and DNA polymerases. As contrasted to oligonucleotides, this allows use of PNA compounds to target genes not only at promoter or regulatory regions of the genome but to other regions as well. Furthermore, only decamer targets are required for efficient binding of the PNA to dsDNA. Consequently, it is easier to identify suitable PNA targets as compared to oligonucleotide triple helix targets.

We have further found that PHA compounds have certain effects on transcription in both prokaryotic and eukaryotic systems. Transcription by RNA polymerases T$_3$ or T$_7$ of PNA T$_{10}$-LysNH$_2$ (SEQ. ID NO:2) and T$_2$CT$_2$CT$_4$-LysNH$_2$ (SEQ ID NO:1) bound to dsDNA targets A$_{10}$ (SEQ ID NO:3), A$_5$GA$_4$ (SEQ ID NO:4) and A$_2$GA$_2$GA$_4$ (SEQ ID NO:5) positioned downstream from T$_3$ or T$_7$ promoters in pBluescriptKS$^+$ plasmids were studied. As shown in our illustrative examples below, transcription elongation is arrested at the site of PNA binding to the template strand, whereas only a marginal effect is observed at the site of PNA binding to the non-template strand. With PNA T$_{10}$-LysNH$_2$ (SEQ ID NO:2), transcription arrest occurs at the first base of the PNA binding site, while arrest with PNA T$_5$CT$_4$-LysNH$_2$ (SEQ ID NO:6) takes place 2–3 bases inside the PNA binding site. In the case of PNA T$_2$CT$_2$CT$_4$-LysNH$_2$ (SEQ ID NO:1), arrest is less efficient and occurs at the last 1–3 bases of the binding site Transcription arrest has ale been shown for PNA T$_6$-LysNH$_2$ (SEQ ID NO:7) and T$_8$-LysNH$_2$, although at lower efficiency compared to longer PNA compounds. These results show that efficient transcription elongation arrest can be obtained by PNA targeting of the transcribed strand, and that "read through" by the polymerase takes place in a sequence dependent manner.

Transcription arrest in eukaryotic systems has further been shown for PNA compounds. For these studies plasmids were constructed with the CMV IE 1 promoter driving the transcription of viral DNA sequences. The viral DNA sequences containing homopurine target sites for the PNAs were cloned downstream of the CMV IE 1 promoter. The plasmids were incubated with PNA oligomers under various conditions then added to eukaryotic nuclear extracts to initiate In vitro transcription. Transcripts were specifically truncated at the site of PNA binding. This effect was dependent upon hybridization of the PNA to the template strand, i.e., the inhibition of transcription was sequence specific. Binding affinity was increased by either lowering the ionic strength or pH of the binding buffer. These results are consistent for PNA binding in which homopyrimidine PNA's invade duplex DNA binding the complementary DNA strand, while displacing the non-complementary strand. A second PNA then interacts with the PNA/DNA duplex forming a stable triple stranded structure which is capable of blocking RNA polymerase II and terminating transcription thus specifically inhibiting eukaryotic gene expression. This use of PNA compounds to inhibit eukaryotic gene expression renders the PNA compounds useful for antigen therapeutics.

In a further embodiment of this invention, we have found that PNA compounds also can be used as sequence specific gene activators and synthetic transcription factors. Transcription initiation by RNA polymerase involves the sequence specific recognition of the double-stranded DNA promoter either by the polymerase itself or by auxiliary transcription factors. Subsequently a transcription initiation open complex is formed in which about 12 base pairs of the DNA helix are melted. This exposes the bases of the template strand for bas pairing with the RNA strand being synthesized. It has been shown that an *E. coli* phage $T_7$ RNA polymerase can utilize synthetic "RNA/DNA bubble duplex" complexes containing an RNA/DNA duplex and a single-stranded DNA D-loop for transcription elongation. We have found that homopyrimidine PNAs also form D-loop structures when binding to complimentary double-stranded DNA by strand displacement. We believe that these structures behave like RNA/DNA open complex structures and are recognized by RNA polymerase.

In the illustrative examples below, we show that *E. Coli* RNA polymerase does indeed bind to PNA/dsDNA strand displacement complexes and initiates RNA transcription therefrom. The results of these examples further suggest that a single-stranded DNA loop is a major structural determinant for RNA polymerase upon transcription initiation and elongation. The results of these examples also have implications for elucidating the mechanism of action of RNA polymerase.

In further embodiments of the invention chimera strands are formed between PNAs and either RNA or DNA. Such chimeric strands can then in the same manner as the "homo" PNA strands described above. Such chimeric structures thus will be used, as described above, for binding, duplexing, triplexing and the like. In one particularly preferred use, either a PNA strand or a PNA containing chimera strand will be used to bind to or otherwise modulate proteins in cells. Such proteins will include transcription factors and other regulatory proteins.

The chimeric structure between PNAs and DNA or RNA are used in place of or in addition to a normal PNA strand to effect duplexing, triplexing, nucleic acid binding or protein binding. The RNA or DNA nucleic acid portion of such chimeric structures include nucleic acid connected via phosphodiester, phosphorothioate, phosphorodithioate, alkyl phosphonate hydrogen phosphonate, phosphotriester, phosphoramidite and other like phosphorus linkages. They further can include other substitutions such as substitution at the 2' position of a ribose sugar. Particularly preferred are 2'-deoxy-2'-fluoro since they increase affinity of the nucleic acid portion of the chimera to other nucleic acids and 2'-O-alkyl, particularly 2'-O-propyl, 2'-O-allyl and the like since they confer nuclease resistance to the nucleic acid strand.

The following examples are given to illustrate the invention. These examples are given for illustrative purposes and are not meant to be limiting.

EXAMPLE 1

General Method for the Synthesis of PNA Oligomers

PNA oligomeric compounds were prepared generally in accordance with the methods disclosed by WO 92/20702, WO 92/20703 and the foregoing United States patent application bearing attorney docket ISIS-1017. Other PNA monomers are prepared as per Examples 34–46 below. Briefly, benzyhydrylamine resin (initially loaded 0.28 mmol/gm with Boc-L-Lys(2-chlorobenzyloxycarbonyl)) was swollen in DMF and an excess of a monomer to be coupled was added, followed by dicyclohexylcarbodiimide (0.15M in 50% DMF in dichloromethane). The Boc deprotection was accomplished by trifluoroacetic acid treatment. The progress of the coupling reactions was monitored by qualitative or quantitative ninhydrin analysis. The PNA was released from the resin using anhydrous HF or trifluoromethyl sultonic acid under standard conditions. The products were purified using HPLC with acetonitrile-water (0.1%TFA) gradient and structure confirmed by fast atom bombardment mass spectrometry.

Representative sequences synthesized by these methods include the following as well as other sequences noted in the various examples:

H-$T_{10}$LysNH$_2$ (SEQ ID NO:2)
H-$T_4CT_5$LysNH$_2$ (SEQ ID NO:8)
H-$T_2CT_2CT_4$LysNH$_2$ (SEQ ID NO:1)
H-$T_4CT_2CT_2$LysNH$_2$ (SEQ ID NO:9)
H-TGTACGTCACAACTA-NH$_2$ (SEQ ID NO:10)
H-CCTTCCCTT-NH$_2$ (SEQ ID NO:11)
H-TTCCCTTCC-NH$_2$ (SEQ ID NO:12)
H-TAGTTATCTCTATCT-NH$_2$ (SEQ ID NO:13)
H-TGTACGTCACAACTA-NH$_2$ (SEQ ID NO:14)
H-GCACAGCC-LYS-NH$_2$ (SEQ ID NO:15)
H-TTTTCTTTT-NH$_2$ (SEQ ID NO:16)
H-TTTTTTTTTCCCCCCC-NH$_2$ (SEQ ID NO: 17)
H-CCCCCCCTTTTTTTTT-NH$_2$ (SEQ ID NO:18)
H-CCTCCTTCCC-NH$_2$ (SEQ ID NO:19)
H-TTCTCTCTCT-NH$_2$ (SEQ ID NO:20)
H-TTTTTCTCTCTCTCT-NH$_2$ (SEQ ID NO:21)
H-CCCCCACCACTTCCCCTCTC-(Lys)$_9$NH$_2$ (SEQ ID NO:22)
H-CTTATATTCCGTCATCGCTC-Lys-NH$_2$ (SEQ ID NO:23)
H-CTGTCTCCATCCTCTTCACT-NH$_2$ (SEQ ID NO:24)
H-TATTCCGTCATCGCTCCTCA-Lys-NH$_2$ (SEQ ID NO:25)
H-CCCCCACCACTTCCCCTCTC-NH$_2$ (SEQ ID NO:26)
H-CTGCTGCCTCTGTCTCAGGT-LysNH$_2$ (SEQ ID NO:27)
H-$T_4$-(β-alanine)C-$T_5$-LysNH$_2$ (SEQ ID NO:28)
H-$T_4$-(β-alanine)T-$T_5$-LysNH$_2$ (SEQ ID NO:29)

The PNA's are written from amino to the carboxyterminal. LysNH$_2$ designates a lysine amide is attached to the PNA and NH$_2$ indicates a free c-terminal carboxamide without lysine.

EXAMPLE 2

Site-specific $S_1$ Nuclease Digestion of the pT10 Plasmid Linearized with CfrlOI Restriction Enzyme and Complexed with PNA (a Double-stranded Target)

Figure 1:
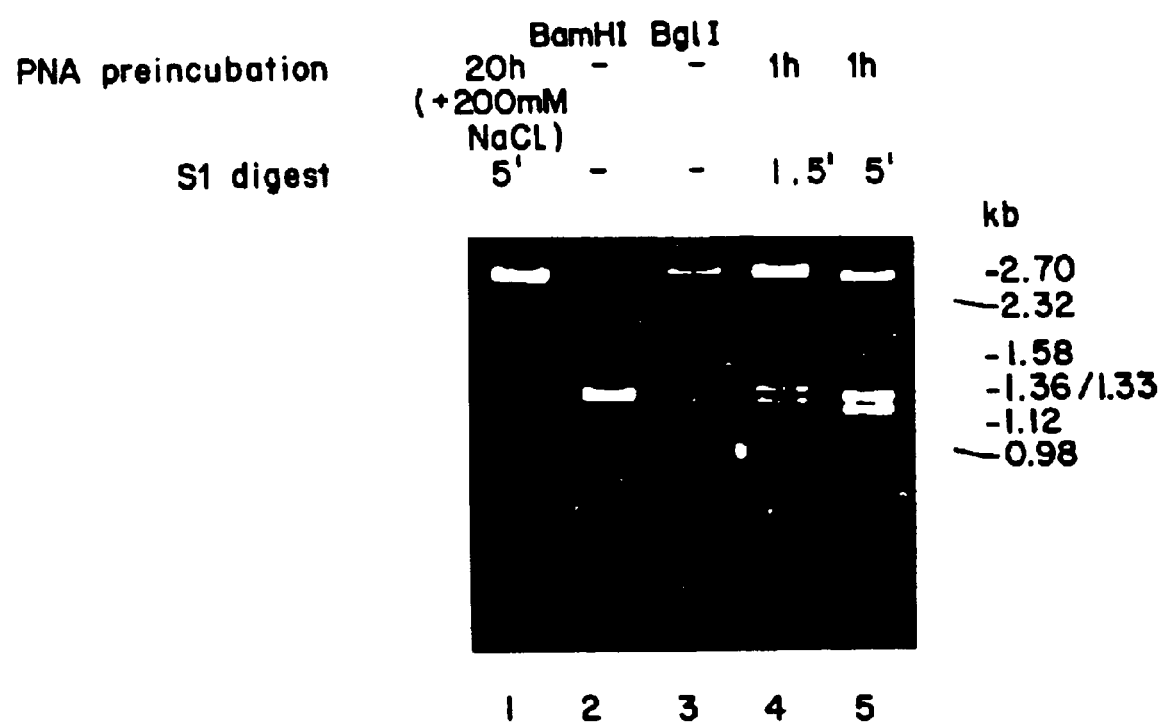
FIG. 1 is an ethidium bromide stained gel showing cleavage in a sequence specific manner by $S_1$ nuclease and a nucleic acid analogue of a double-stranded DNA having a single site for hybridization to the nucleic acid analogue (Example 1)

PNA H-$T_{10}$-LysNH$_2$ (SEQ ID NO:2) was synthesized as described in Example 1. A pT10 plasmid was prepared from the pUC19 plasmid by inserting the dA$_{10}$/dT10 (SEQ ID NO:3) sequence into the BamHl site of the polylinker as per the method of Egholm, N et al., *J.A.C.S.* 1992 114:1895–1897. The pT10 plasmid was linearized with CfrlOI restriction enzyme in the unique site. To form complex with the PNA, about0.1 μg of the linearized plasmid was incubated with 2 o.u./ml of PNA in 3 μl of the TE buffer (10 mM Tris-HCl; 1 mM EDTA, pH 7.4) at 37° C. To perform the $S_1$ nuclease reaction, 10 μl of Na-Acetate buffer (33 mM NaAc; 50 mM NaCl; 10 mM ZnSO$_4$; 0.5% of glycerol, pH 4.6) and 145 units of $S_1$ nuclease (Sigma) were added and incubated for various time periods at room temperature. The reaction was terminated by adding 1 μl of 0.5 M EDTA and cooling to −20° C. Electrophoresis was performed in 1% agarose gel in the TBE buffer with subsequent staining with ethidium bromide. The results of this example are shown in FIG. 1 wherein the size of the markers are shown as are the incubation time periods. In FIG. 8 Lane 1: control—preincubation of DNA with PNA was performed under conditions unfavorable for complex formation (200 mM of NaCl). Lane 2: the reference band obtained by digestion with BamHI restriction enzyme. Lane 3: reference bands obtained by the digestion with BglI restriction enzyme. Lanes 4,5: the results of $S_1$ nuclease digestion for different times of DNA-PNA complex.

As is shown in this example, targets were cloned within a pUC 19 polylinker. The plasmids were linearized with the CfrlOI restriction enzyme. In the linear DNA, the obtained polylinker region is in the middle (1.33 kb from one end and 1.36 kb from the other). Utilizing a direct approach, a pTlO plasmid carrying the sequence $dA_{10}dT_{10}$ (SEQ ID NO:31) was inserted in the unique BamHl site in the polylinker. This was complexed with PNA H-$T_{10}$-LysNH$_2$ (SEQ ID NO:2) and subjected to treatment with $S_1$ nuclease. After treatment with 145 units of $S_1$ nuclease at room temperature a significant fraction of DNA was cut. The mobility by gel electrophoresis of the resulting fragments was very close to the mobility of fragments obtained by cutting with restriction enzyme BamHl . Similar results were obtained for H-$T_5CT_4$-LysNH$_2$ (SEQ ID NO:6) and H-$T_2CT_2$CT-LysNH$_2$ (SEQ ID NO:51) PNAs and corresponding plasmids carrying the d($A_5GA_6$)/d($T_4CT_5$) (SEQ ID NO:4) and d($A_4GA_2GA_2$)/d($T_2CT_2CT_4$) (SEQ ID NO:44) inserts. Cross reactivity experiments showed that the targeting was sequence specific: only corresponding PNAs mediated cutting of the targets. It was noted that two very week bands are seen in lanes 4,5, which correspond to lengths 2.32 and 0.98 kb. These bands are due to weak binding of PNA-TlO to the intrinsic pUC19 site d(TTGT3)/d(A3CAT), which is 0.37 kb apart from the CfrlOI restriction site. This is consistent with the results of Example 3 above that shows that the introduction of mismatches dramatically decreases the affinity of PNA to DNA.

From this example it is believed that the enzyme first digests the displaced strand, then to some extent enlarges the gap after which the opposite strand becomes a substrate for the enzyme. As a result, the double-stranded break is created. The yield of digested molecules is high and one can reach the quantitative digestion with increasing exposure to $S_1$ nuclease (data not shown). However, while the two fragments are poorly resolved after digestion with BamHI restriction enzyme, the PNA-mediated digestion with the $S_1$ nuclease leads to the clear-cut doublet. While not wishing to be bound by theory, we believe this probably reflects a widening of thee gap by the $S_1$ nuclease as well as digestion from the ends of the CfrlOI site with longer treatment the downward shift of the doublet becomes noticeable (see lane 5). Thus, quantitative digestion is clearly accompanied by a truncation of the fragments (by about hundred base pairs). To obtain further precision of cutting comparable with that exhibited by natural restriction enzymes the original approach is modified as per Example 4 below. Alternate Site-specific $S_1$ Nuclease Digestion of Plasmid with PNA)

As an alternative target, the insert:

5'-$A_5GA_4$GTCGAC$A_5GA_4$-3' (SEQ ID NO:30)
3'-$T_5CT_4$CAGCTG$T_5CT_4$-5' (SEQ ID NO:84)

was cloned into the Sal1 site of the pUC19 plasmid. This plasmid, which contained two binding sites for PNA H-$T_5CT_4$-LysNH$_2$ (SEQ ID NO:6) separated by six base pairs, was designated pT9CT9C. Strand displacement in the two $T_5CT_4$ sites led to opening of the entire region, including the sequence GTCGAC/GACGAC, providing a substrate for the $S_1$ nuclease in both strands. As control, a pT9C-5 plasmid was used, which carried only one $T_5CT_4$ (SEQ ID NO:6) insert cloned into the Sall site of the pUC19 plasmid.

EXAMPLE 3

Site-specific $S_1$ Nuclease Digestion of the pT9C Plasmid Linearized by CfrlOI Restriction Enzyme and Complexed with PNA H-$T_5CT_4$-LysNH$_2$ This example illustrates the use of one molecule of PNA hybridized to a target DNA to define a restriction site.

PNA 1,2 and 3 were synthesized as Example 1 and the results are shown in FIG. 2. A pT9C plasmid carried the insert:

5'-$A_5GA_4$GTCGAC$A_5GA_4$-3' (SEQ ID NO:30)
3'-$T_5CT_4$CAGCTG$T_5CT_4$-5' (SEQ ID NO:84), cloned in the Sal1 site of the pUC19 polylinker. The pT9C-5 plasmid carried the single insert $A_5GA_4/CT_5$ (SEQ ID NO:4) cloned in the same site. The PNA-DNA complexes were prepared as described in Example 2 with the only difference being the duration of the incubation was 2 hours. Digestion by 30 units of the $S_1$ nuclease was performed in the same buffer as described in Example 2 with two exceptions, lanes 2 and 4. In lane 2, 15 units of the enzyme were used, whereas in lane 4 200 mM NaCl and 1 mM of ZnSO$_4$ were added to the buffer. Lane 1: the reference band obtained by digestion with the BamHI restriction enzyme of the pUC 19 plasmid linearized by the CfrlOI restriction enzyme. Lanes 2–4 site-specific digestion by the $S_1$ nuclease of the linearized pT9C plasmid complexed with PNA H-$T_5CT_4$-LysNH$_2$ (SEQ ID NO:6). Lanes 5–7: various controls. Lane 8: the same experiment as in lane 3, but using PNA $T_{10}$ (SEQ ID NO:2) instead of $T_4CT_5$ (SEQ ID NO:8). Lane 9: the same experiment as in lane 3, but using PNA $T_2CT_2CT_4$ (SEQ ID NO:1) instead of $T_4CT_5$ (SEQ ID NO:8). Lane 10: the same experiment as in lane 3, but using the pT9C-5 plasmid instead of the pT9C. In the header PNA $T_5CT_4$ (SEQ ID NO:6) is labelled as 1, $T_{10}$ (SEQ ID NO:2) as 2 and $T_2CT_2CT_4$ (SEQ ID NO:1) as 3.

This example show that subjecting the pT9CT9C plasmid, linearized by the CfrlOI restriction enzyme and complexed with PNA H-$T_5CT_4$-LysNH$_2$ (SEQ ID No:6), to 30 units of the $S_1$ nuclease results in full conversion of the full-length DNA molecules into half-length fragments. The bands observed by gel electrophoresis have the same position and width as the band created by the BamHI restriction enzyme. Sequence specificity of this artificial "restriction enzyme" was confirmed by the very weak digestion of the pT9C plasmid in case of complexing with PNA H-$T_{10}$-LysNH$_2$ (SEQ ID NO:2) and H-$T_2CT_2CT_4$-LysNH$_2$ (SEQ ID NO:1) under conditions which result in quantitative cutting of the plasmid in the presence of PNA H-$T_5CT_4$-LysNH$_2$ (SEQ ID NO:6) (see lanes 8,9). Moreover, under the much milder $S_1$ nuclease treatment necessary to generate the data for the pT9CT9C, the yield of double-stranded breaks in the pT9C-5 plasmid was extremely low (lane 10).

EXAMPLE 4

Figure 3:
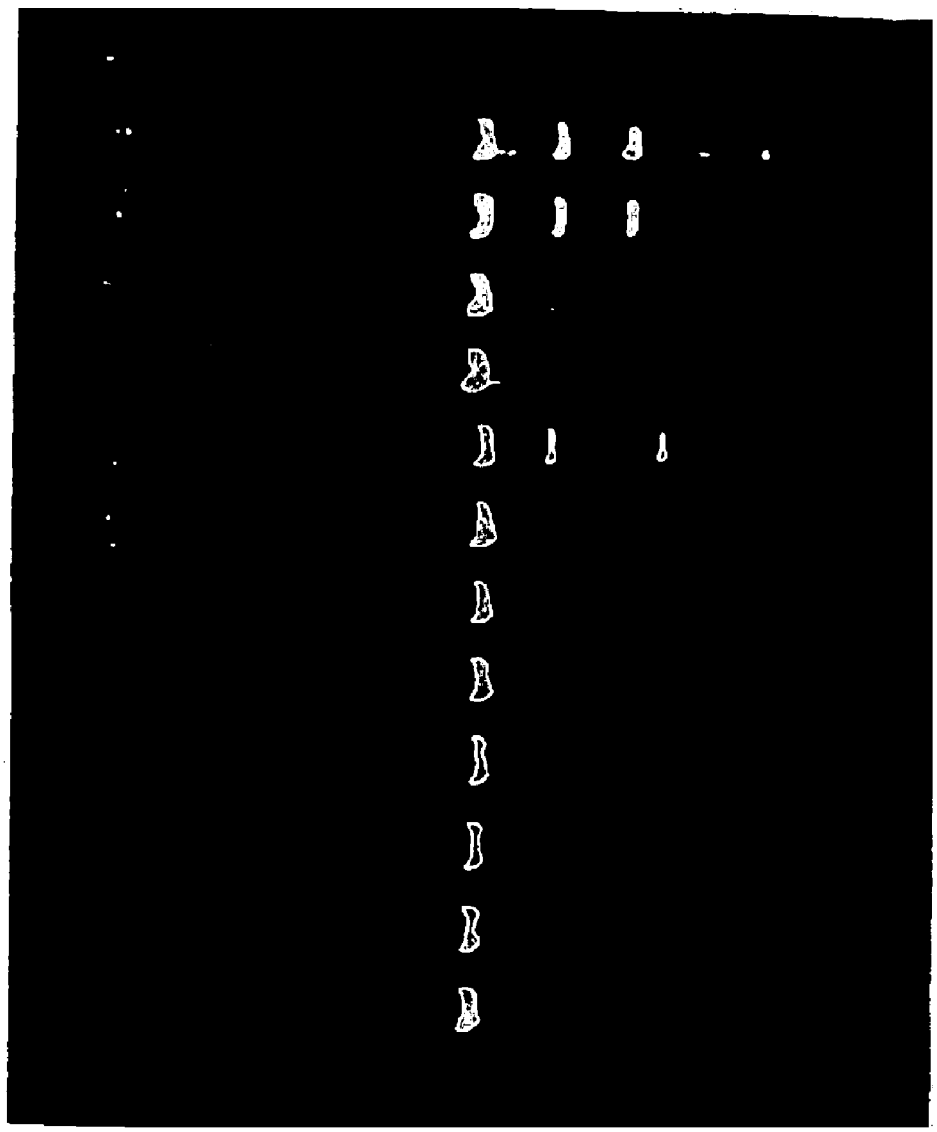
FIG. 3 is an ethidium bromide stained gel showing a similar cleavage of a double-stranded DNA having two closely spaced sites for hybridization to a nucleic acid analogue on opposite strands (Example 3)

Site Specific $S_1$ a Nuclease Cleavage of the Plasmids pT9C-5, pT9CT9C and pT9CA9GKS (Linearized with Sca1) Targeted by PNA $T_4CT_5$-LysNH$_2$ This example illustrates the use of two molecules of PNA bound to opposite strands of a DNA target. A further plasmid pT9CA9GKS was produced by cloning the insert GTCGAC$A_5GA_4$GTCGAC$T_4CT_5$GTCGAC (SEQ ID NO:32) into pUC$_{19}$ at the Sal I site and linearizing with Sca I restriction enzyme. The linearized plasmid has two hybridization sites for PNA H-$T_4CT_5$-Lys NH$_2$ (SEQ ID NO:8) on opposite strands spaced by six bas pairs. The protocol of Example 3 was use except the samples were treated using 1 U/$\mu$l of $S_1$ and 15 min incubation at 37° C. The results are shown in FIG. 3 Lanes 1–4: pT9C-5; lanes 5–8: pT9CT9C;

lanes 9–12: pT9CA9GKS. Lanes 1, 5 & 9: no PNA; lanes 2, 6 & 10: 50 µM; lanes 3, 7, 11: 500 uM; lanes 4, 8, 12: 5 mM.

EXAMPLE 5

Use of PIM/nuclease to Cut Selectively Large DNA Molecule

The standard strain lambda cI ind1 ts857 Sam7 (New England Biolab) was used. The PNA double target was $T_7N_6T_7$ (SEQ ID NO:33) which upon cleavage should give rise to a 6.1 kb fragment. The PNA was a PNA $(T_7)_2$ and the conditions were as follows: 0.1 µg DNA and 1–2 OD units of PNA were incubated in 5 µl TE buffer for 10 min at 37° C. 5 µl buffer (33 mM NaAc, 30 mM NaCl, 10 µM $ZnSO_4$, pH 4.5) and 20 U mung bean nuclease were added and the mixture was incubated for 5 min at room temperature. Upon analysis by electrophoresis in 0.5% agarose in TBE buffer, fragments of sizes 6 kb and 42 kb were observed using lambda x Hind III or Sal I as size markers. Without additions of PNA no bands were seen.

This example demonstrates the ability of PNA/nuclease to cut selectively a large DNA molecule (by comparison to the much smaller plasmids used in Examples 1 to 3).

EXAMPLE 6

Binding of PNAS-$T_{10}/T_9C/T_8C_2$ to Double-stranded DNA Targets $A_{10}/A_9G/A_8G_2$ A mixture of 200 cps $^{32}$P-labeled EcoRI-PvuII fragment (the large fragment labeled at the 3'-end of the EcoRI site) of the indicated plasmid, 0.5 µg carrier calf thymus DNA, and 300 ng PNA in 100 µl buffer (200 mM NaCl, 50 mM Na-acetate, pH 4.5, 1 mM $ZnSO_4$) was incubated at 37° C. for 120 min. A 50 unit portion of nuclease $S_1$ was added and incubated at 20° C. for 5 min. The reaction was stopped by addition of 3 µl 0.5 M EDTA and the DNA was precipitated by addition of 250 µl 2% potassium acetate in ethanol. The DNA was analyzed by electrophoresis in 10% polyacrylamide sequencing gels and the radiolabeled DNA bands visualized by autoradiography.

The target plasmids were prepared by cloning of the appropriate oligonucleotides into pUC19. Target Alo (SEQ ID NO:50): oligonucleotides GATCCA$_{10}$G (SEQ ID NO:34) & GATCCT$_{10}$G (SEQ ID NO:35) cloned into the BamHI site (plasmid designated pT$_{10}$). Target $A_5GA_4$ (SEQ ID NO:4): oligonucleotides TCGACT$_4$CT$_5$G (SEQ ID NO:36) & TCGACA$_5$GA$_4$G (SEQ ID NO:37) cloned into the SalI site (plasmid pT9C). Target $A_2GA_2GA4$ (SEQ ID NO:57): oligonucleotides CA$_2$GA$_2$GA$_4$CTGCA (SEQ ID NO:38) and GT$_4$CT$_2$CT$_2$CTGCA (SEQ ID NO:39) into the PstI site (plasmid pT8C2). The results are shown in FIG. 4. The positions of the targets in the gel are indicated by bars to the left. A/G is an A+G sequence ladder of target P10.

EXAMPLE 7

Figure 5:
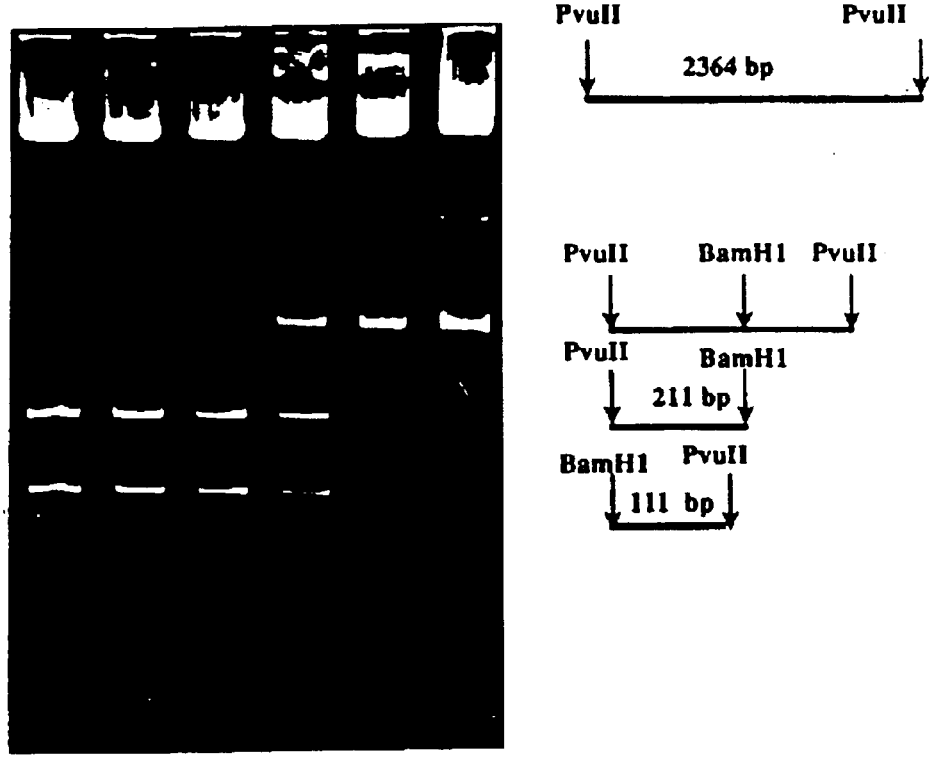
FIG. 5 shows an electrophoretic gel staining demonstrating that restriction enzyme activity towards DNA is inhibited when PNA is bound proximal to the restriction enzyme recognition site.

Inhibition of Restriction Enzyme Cleavage by PNA (FIG. 5).

A 2 µg portion of plasmid pT10 was mixed with the indicated amount of PNA-$T_{10}$ (SEQ ID NO:2) in 20 µl TE buffer (10 mM Tris-HCl, 1 mH EDTA, pH 7.4) and incubated at 37° C. for 120 min. 2 µl 10×buffer (10 mM Tris-HCl, pH 7.5, 10 mM, $MgCl_2$, 50 mM NaCl, 1 mM DTT). PvuII (2 units) and BamHI (2 units) were added and the incubation was continued for 60 min. The DNA was analyzed by gel electrophoresis in 5% polyacrylamide and the DNA was visualized by ethidium bromide staining. This gel is illustrated in FIG. 5.

EXAMPLE 8

Kinetics of PNA-$T_{10}$—dsDNA Strand Displacement Complex Formation

Figure 6:
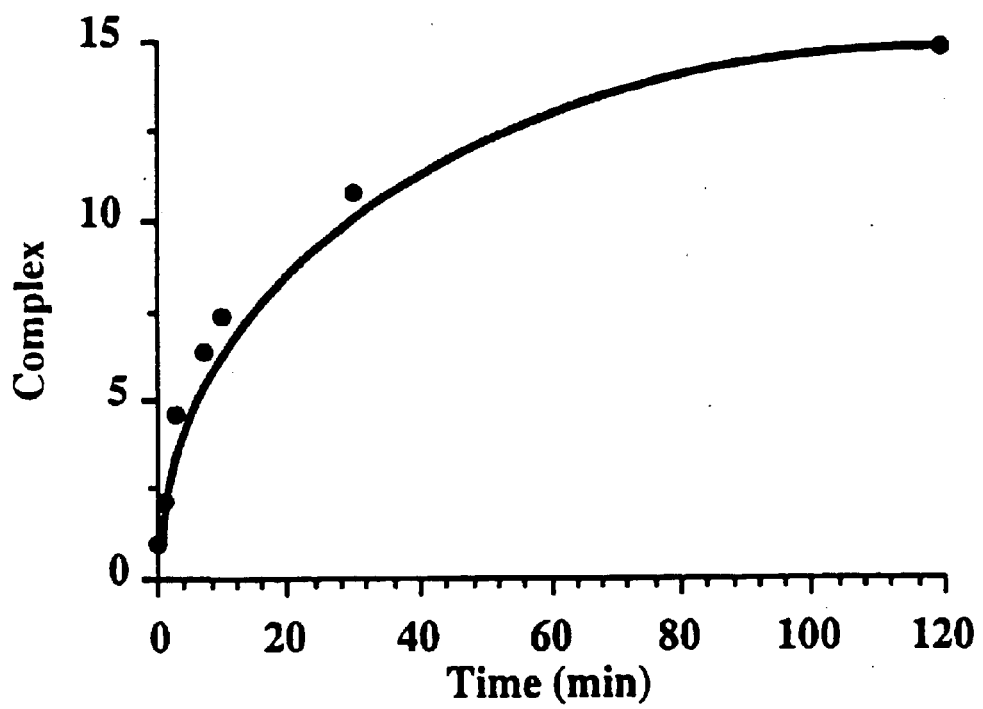
FIG. 6 shows a graph based on densitometric scanning of PAGE autoradiographs demonstrating the kinetics of the binding of PNA-$T_{10}$ to a double-stranded target.

A mixture of 200 cps $^{32}$P-labeled EcoRI-PvuII fragment of pTlO (the large fragment labeled at the 3'-end of the EcoRI site), 0.5 µg carrier calf thymus DNA, and 300 ng of PNA-$T_{10}$-LysNH$_2$ (SEQ ID NO:2) in 100 µl buffer (200 mM NaCl, 50 mM Na-acetate, pH 4.5, 1 mM $ZnSO_4$) were incubated at 37° C. At the times indicated, 50 U of $S_1$ nuclease was added to each of 7 samples and incubation was continued for 5 min at 20° C. The DNA was then precipitated by addition of 250 µl 2% K-acetate in ethanol and analyzed by electrophoresis in a 10% polyacrylamide sequencing gel. The amount of strand displacement complex was calculated from the intensity of the $S_1$-cleavage at the target sequence, as measured by densitometric scanning of autoradiographs. The results are illustrated in FIG. 6.

EXAMPLE 9

Stability of PNA-dsDNA Complexes

Figure 7:
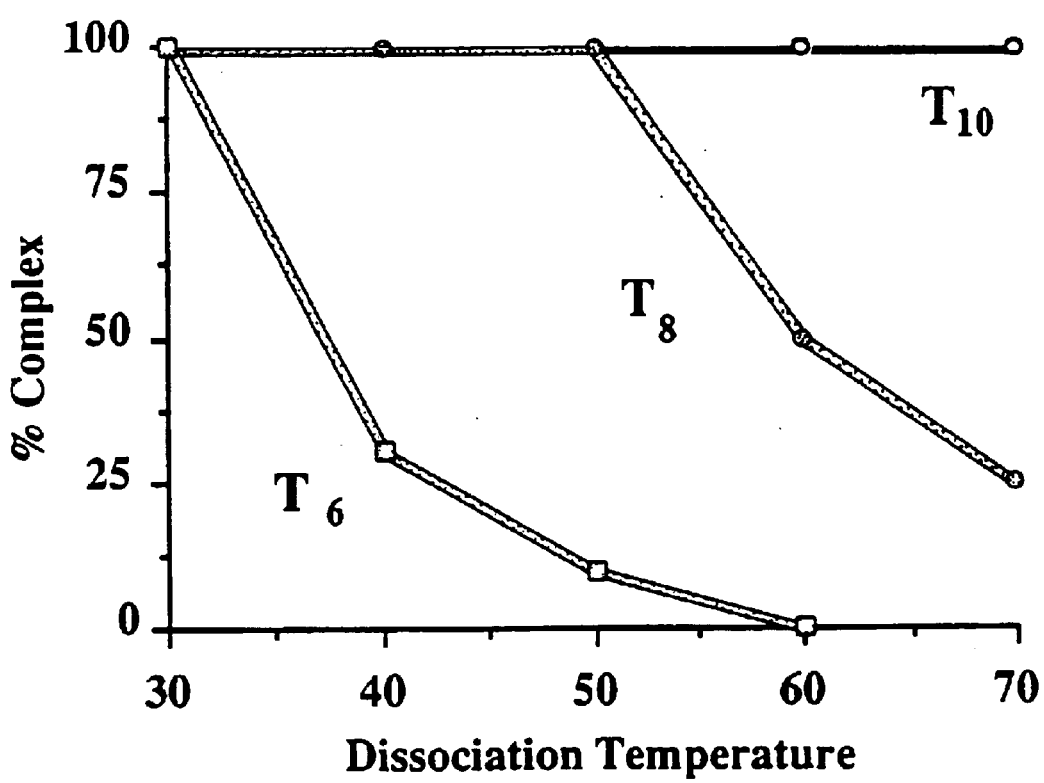
FIG. 7 shows a graph based on densitometric scanning of PAGE autoradiographs demonstrating the thermal stabilities of PNAs of varying lengths bound to an $A_{10}$ (SEQ ID NO:59)/$T_{10}$ (SEQ ID NO:2) double-stranded DNA target.

A mixture of 200 cps $^{32}$P-pTlO fragment, 0.5 µg calf thymus DNA and 300 ng of the desired PNA (either $T_{10}$-LysNH$_2$ (SEQ ID NO:2), $T_6$-LysNH$_2$ (SEQ ID NO:40) or $T_6$-LysNH$_2$ (SEQ ID NO:7)) was incubated in 100 µl 200 mM NaCl, 50 mM Na-acetate, pH 4.5, 1 mM $ZnSO_4$ for 60 min at 37° C. A 2 µg portion of oligonucleotide GATCCA$_{10}$G (SEQ ID NO:34) was added and each sample was heated for 10 min at the temperature indicated, cooled in ice for 10 min and warmed to 20° C. A 50 U portion of $S_1$ nuclease was added and the samples treated and analyzed and the results quantified as is illustrated in FIG. 7.

EXAMPLE 10

Biological Stability of PNA

A mixture of PNA-$T_5$ (SEQ ID NO:41) (10 µg) and a control, "normal" peptide (10 µg) in 40 µl 50 mM Tris-HCl, pH 7.4 was treated with varying amounts of peptidase from porcine intestinal mucosa or protease from *Streptomyces caespitosus* for 10 min at 37° C. The amount of PNA and peptide was determined by HPLC analysis (reversed phase C-18 column: 0–60% acetonitrile, 0.1% trifluoroacetic acid).

At peptidase/protease concentrations where complete degradation of the peptide was observed (no HPLC peak) the PNA was still intact.

EXAMPLE 11

Inhibition of Gene Expression

A preferred assay to test the ability of peptide nucleic acids to inhibit expression of the E2 mRNA of papillomavirus is based on the well-documented transactivation properties of E2. Spalholtz, et al., *J. Virol.,* 1987, 61, 2129–2137. A reporter plasmid (E2RECAT) was constructed to contain the E2 responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 has been tested by transfection of this plasmid into C127 cells transformed by BPV-1, uninfected C127 cells and C127 cells cotransfected with E2RECAT and an E2 expression vector.

A. Inhibition of BPV-1 E2 Expression

BPV-1 transformed C127 cells are plated in 12 well plates. Twenty four hours prior to transfection with E2RE1, cells are pretreated by addition of antisense PNAs to the growth medium at final concentrations of 5, 15 and 30 mL.

The next day cells are transfected with 10 μg of E2RE1CAT by calcium phosphate precipitation. Ton micrograms of E2RE1CAT and 10 μg of carrier DNA (PUC 19) are mixed with 62 μl of 2 M $CaCl_2$ in a final volume of 250 μl of $H_2O$, followed by addition of 250 μl of 2×HBSP (1.5 mM $Na_2PO_2$. 10 mM KCl, 280 mM NaCl, 12 mM glucose and 50 mM HEPES, pH 7.0) and incubated at room temperature for 30 minutes. One hundred microliters of this solution is added to each test well and allowed to incubate for 4 hours at 37° C. After incubation, cells are glycerol shocked for 1 minute at room temperature with 15% glycerol in 0.75 am $Na_2PO_3$, 5 mH KCl, 140 mM NaCl, 6 mM glucose and 25 mM HEPES, pH 7.0. After shocking, cells are washed 2 times with serum free DMEM and fed with DMEM containing 10% fetal bovine serum and antisense oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 μl of 250 mM Tris-HCl, pH 8.0 and disrupted by freeze-thawing 3 times. Twenty four microliters of cell extract is used for each assay. For each assay the following are mixed together in an 1.5 ml Eppendorf tube and incubated at 37° C. for one hour: 25 μl of cell extract, 5 μl of 4 mM acetyl coenzyme A, 18 μl $H_2O$ and 1 μl $^{14}C$-chloramphenicol, 40–60 mCi/mM. After incubation, chloramphenicol (acetylated and nonacetylated forms) is extracted with ethyl acetate and evaporated to dryness. Samples are resuspended in 25 μl of ethyl acetate, spotted onto a TLC plate and chromatographed in chloroform-:methanol (19:1). Chromatographs are analyzed by autoradiography. Spots corresponding to acetylated and nonacetylated $^{14}C$-chloramphenicol are excised from the TLC plate and counted by liquid scintillation for quantitation of CAT activity. Peptide nucleic acids that depress CAT activity in a dose dependent fashion are considered positives.

B. Inhibition of HPV E2 Expression

The assay for inhibition of human papillomavirus (HPV) E2 by peptide nucleic acids is essentially the same as that for BPV-1 E2. For HPV assays appropriate HPVs are co-transfected into either CV-1 or A431 cells with PSV2NEO using the calcium phosphate method described above. Cells which take up DNA are selected for by culturing in media containing the antibiotic G418. G418-resistant cells are then analyzed for HPV DNA and RNA. Cells expressing E2 are used as target cells for antisense studies. For each PNA, cells are pretreated as above, transfected with E2RE1CAT, and analyzed for CAT activity as above. Peptide nucleic acids are considered to have a positive effect if they can depress CAT activity in a dose dependent fashion.

EXAMPLE 12
Triplexing of PNA to Nucleic Acids—Probing Protocols

Probing was effected in 100μ buffer (S1: 100 mM NaCl, 1 mM $ZnSO_4$, 50 mM NaAc, pH 4.5; $KMnO_4$/dimethyl sulphate (DMS): 10 mM Na-cacodylate, 1 mM EDTA, pH 7.0 or as other wise noted) containing about 200 cps $^{32}P$-labeled DNA fragment, 0.5 μg calf thymus DNA and the desired amount of PNA. Following a preincubation for 60 min at 37° C., the probing reagent was added and the incubation was continued at room temperature. The reactions were terminated by the addition of a stop-buffer. The DNA was precipitated by addition of 200 μL. 2% KAc in 96% EtOH and was analyzed by electrophoresis in 10% polyacrylamide sequencing gels. Radioactive DNA bands were visualized by autoradiography using amplifying screens and Agfa curix RPA X-ray films exposed at −70° C. Probing conditions were: S1: 0.5 U/μl, 5 min. stopped with 3 μl 1 M EDTA; $KMnO_4$: 1 mM, 15 sec. stopped with 50 μl 1M 6-mercaptoethanol, 1.5 M NaAc, pH 7.0; DMS: 1% DMS, 15 sec., stopped as for $KMnO_4$ probing. Samples probed with DMS or $KMnO_4$ were treated with piperidine (0.5 M, 90° C., 20 min.) prior to gel analysis.

EXAMPLE 13
Enzymatic and Chemical Probing of the binding of PNA $T_2CT_2CT_4$-LysNH$_2$ to pT9C2A8G2

Figure 10:
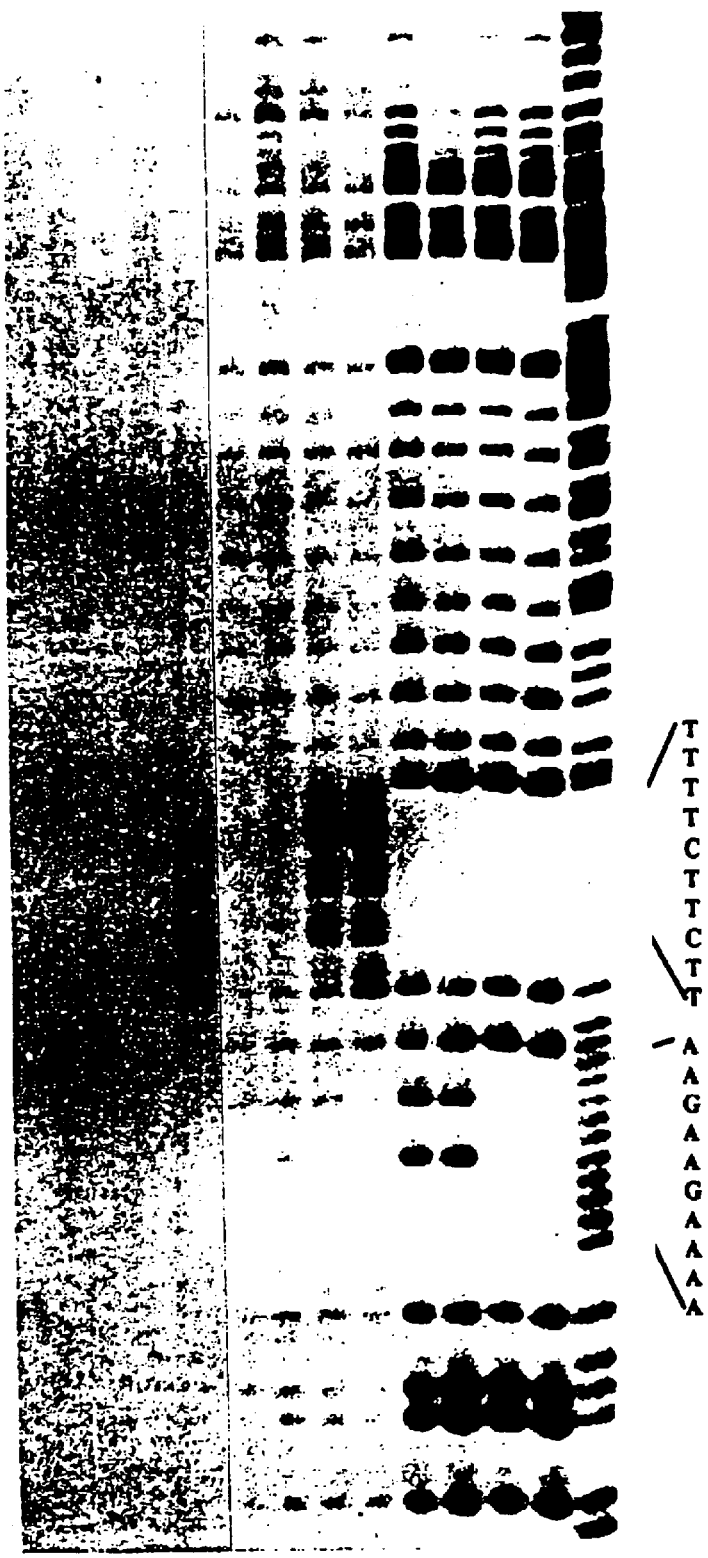
FIG. 10 shows a footprinting experiment of the binding of PNA to a dimeric target comprising sequences TTTTCT-TCTT (SEQ. ID. NO:64) and AAGAAGAAAA (SEQ. ID. NO:5)

For this example the 264 bp EcorI/PvuII fragment of pT8C2A8G2 that was 3'-$^{32}P$-end-labeled at the EcorI site was used. Probing was effected as per the protocols of Example 16. The results are shown in FIG. 10. Lane 1 is a control in S1 buffer without $S_1$ nuclease and without PNA. Lanes 2–5: $S_1$ probing, lanes 6–9: $KMnO_4$ probing and lanes 10–13: DMS probing. The following concentrations of PNA were used: 0 μM (lanes 2, 6 & 10), 0.25 μM (lanes 3, 7 & 11), 2.5 μM (lanes 4, 8 & 12) or 25 μM (lanes 5, 9 & 13). Lanes S are A+G sequence markers.

The plasmid pT8C2A8G2 contains two targets for PNA $T_2CT_2CT_4$ (SEQ ID NO:1) in opposite orientation. Therefore both $KMnO_4$ (thymines of the pyrimidine strand) and DMS (guanines of the purine strand) probing was done on the same DNA fragment. Probing with single strand specific nuclease, $S_1$, verified that upon binding of PNA, the pyrimidine strand but not the purine strand of the PNA targets, became susceptible to attack by $S_1$ (FIG. 10, lanes 2–5). Interestingly, however, in the absence of PNA $S_1$ attacks the purine strand (lane 2). This is undoubtedly due to the formation of an intramolecular triple helix (H-DNA), a well characterized feature of such polypurine/pyrimidine mirror repeats. It is also observed that in the presence of PHA, the Sa sensitivity extends into the linker between the two PNA targets. This can be explained if both PNA targets are occupied, thereby forming a combined loop where the DNA region between the targets is single-stranded. This type of binding further illustrates that PNA can be used for directed double strand DNA cleavage by $S_1$.

Figure 13A:
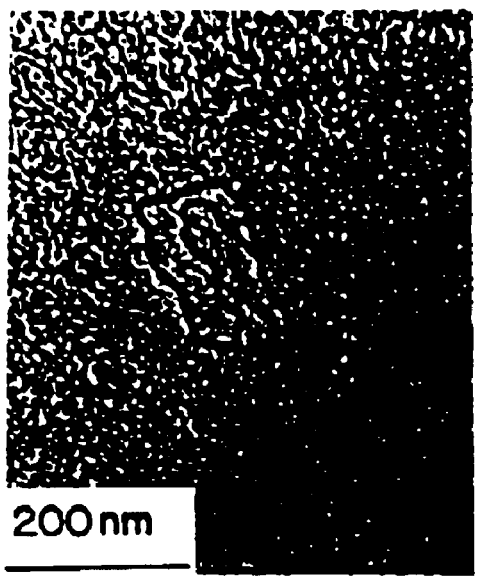
FIG. 13 is an electron micrograph of a PNA double strand DNA complex.
Figure 13B:
Figure 13C:
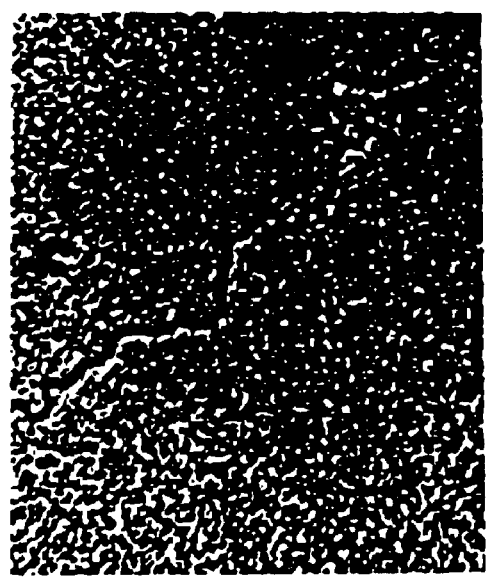

The $KMnO_4$ probing of the PNA-dsDNA complex reveals that all thymines of the target are oxidized by $KMnO_4$ (FIG. 13, lanes 8–9). Concomitantly (in terms of PNA concentration) with the occurrence of $KMnO_4$ susceptibility, virtually full protection against reaction with DMS is observed at the two guanines of the opposite PNA target (see FIG. 10, lanes 12–13). These results show that displacement of the pyrimidine strand of the DNA target is accompanied by protection of the major groove upon binding of PNA supporting the model in which two PNA strands are participating in the PNA-DNA complex forming PNA DNA-DNA triplex.

Figure 11:
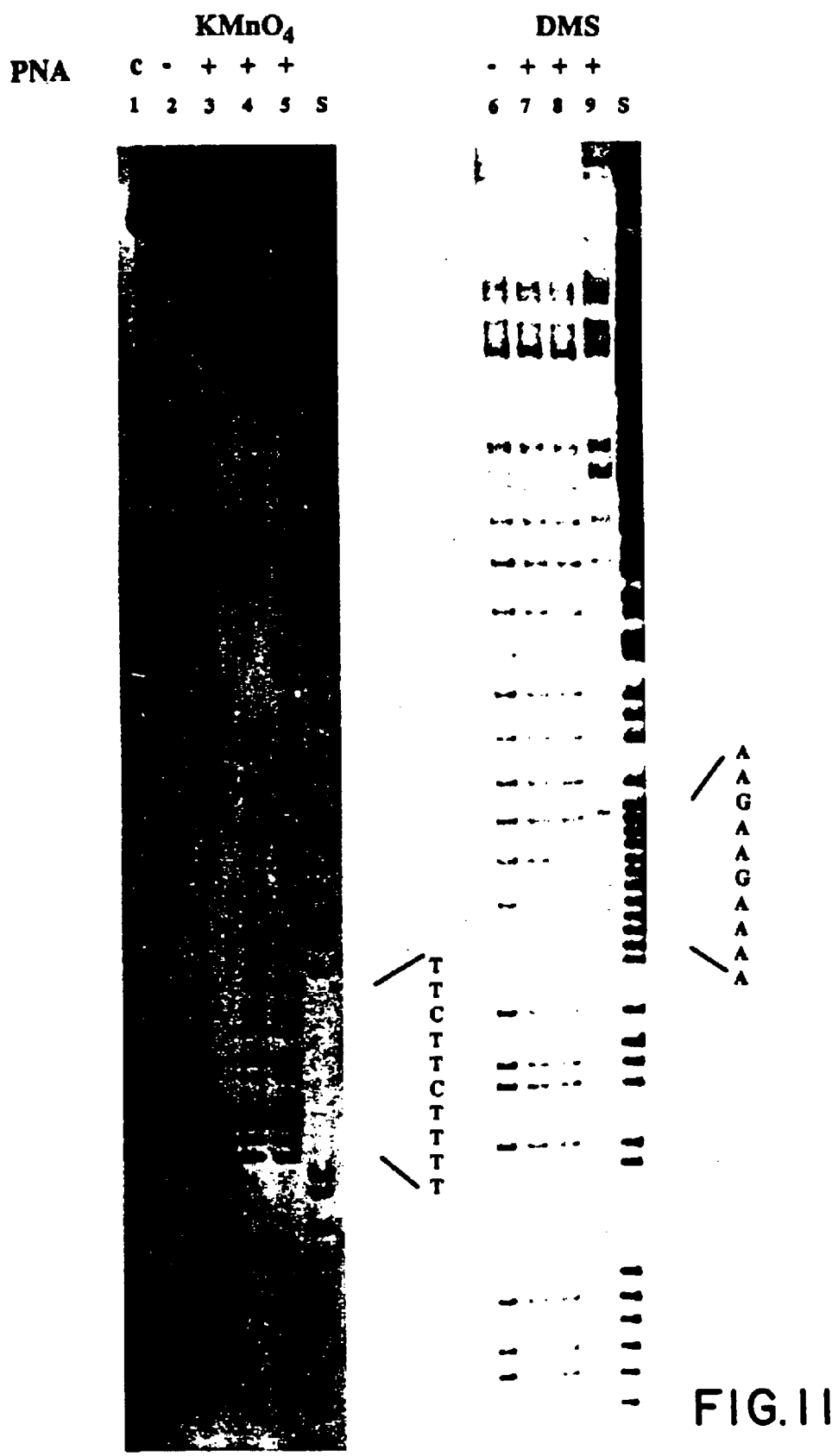
FIG. 11 shows a footprinting experiment of PNA binding to a monomeric target comprising sequences TTCTTCT (SEQ. ID. NO:66) and AAGAAGAAAA (SEQ. ID. NO: 5)

EXAMPLE 14
Chemical Probing of the Binding of PDA $T_2CT_2CT_4$-LysNH$_2$ to pA8G2 For this example, the 248 bp EcoRI/PvuII fragment of pA8G2 was used that was $^{32}P$-end-labeled (5'-labeling, lanes 1–5) or (3'-labeling, lanes 6–9)) at the EcoRI site. Probing was effected as per the protocols of Example 12. The results are shown in FIG. 11 wherein lane 1 is a control in S1 buffer without $S_1$ nuclease and without PNA. Lanes 2–5: $KMnO_4$ probing and lanes 6–9: DMS probing. The following concentrations of PNA were used: 0 μM (lanes 2 & 6), 0.25 μM (lanes 3 & 7), 2.5 μM (lanes 4 & 8) or 25 μM (lanes 5 & 9). Lanes S are A+G sequence markers.

Figure 14:
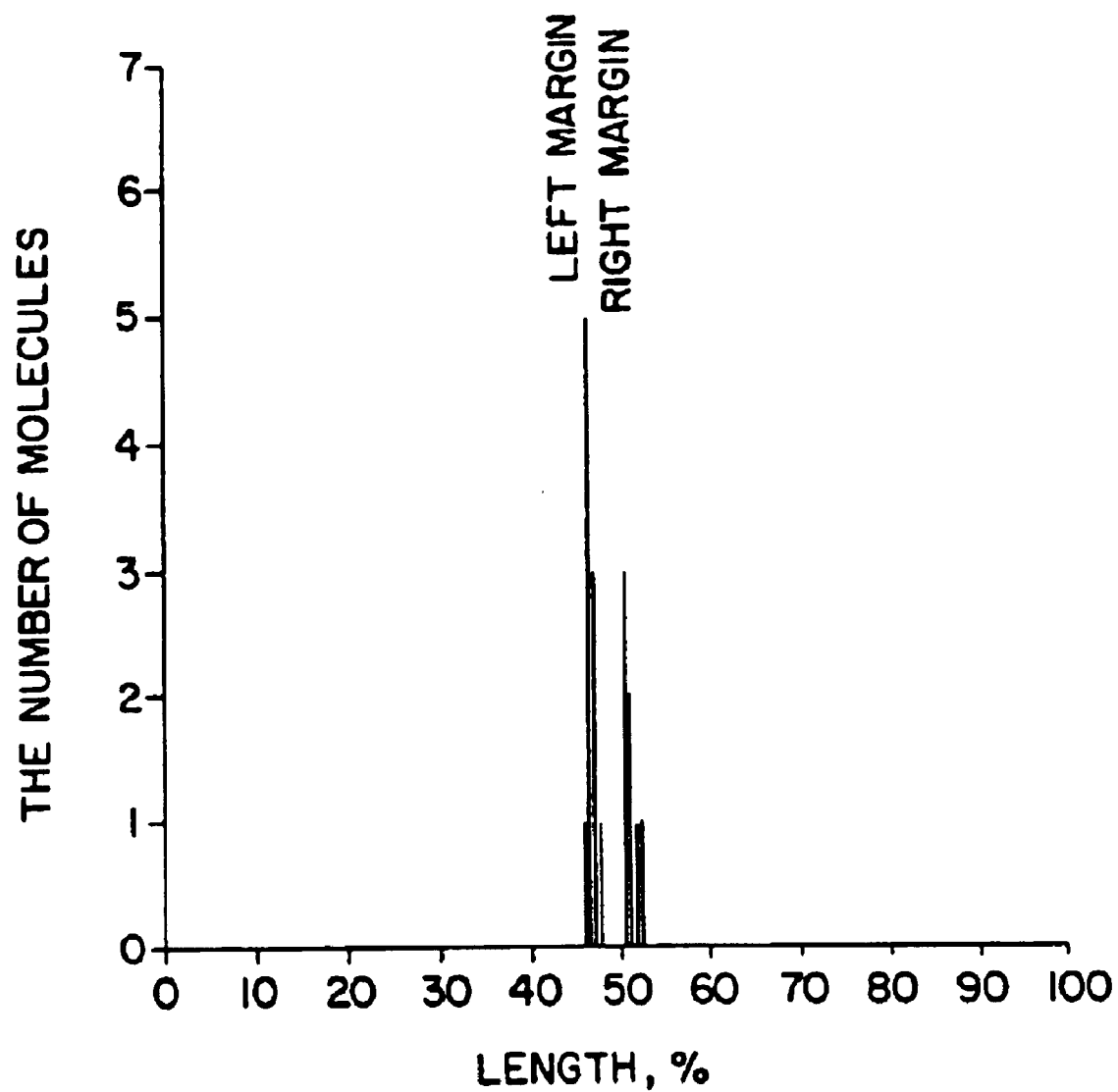
FIG. 14 is a histogram representation of the results obtained in the experiments of FIG. 13.

In this example, in order to assure that the results were not an artifact of the dimeric target, we performed a similar experiment to that of Example 13 except a plasmid (pA8G2) having only a single PNA target was used. As is seen in FIG. 14, virtually identical results to those with the dimeric target of Example 13 were obtained with $KMnO_4$ and DMS probing of the single target.

EXAMPLE 15
Effect of pH End Ionic Strength of the Binding of PHA $T_2CT_2CT_4$-LysNH$_2$ to pT8C2A8G2

Figure 12:
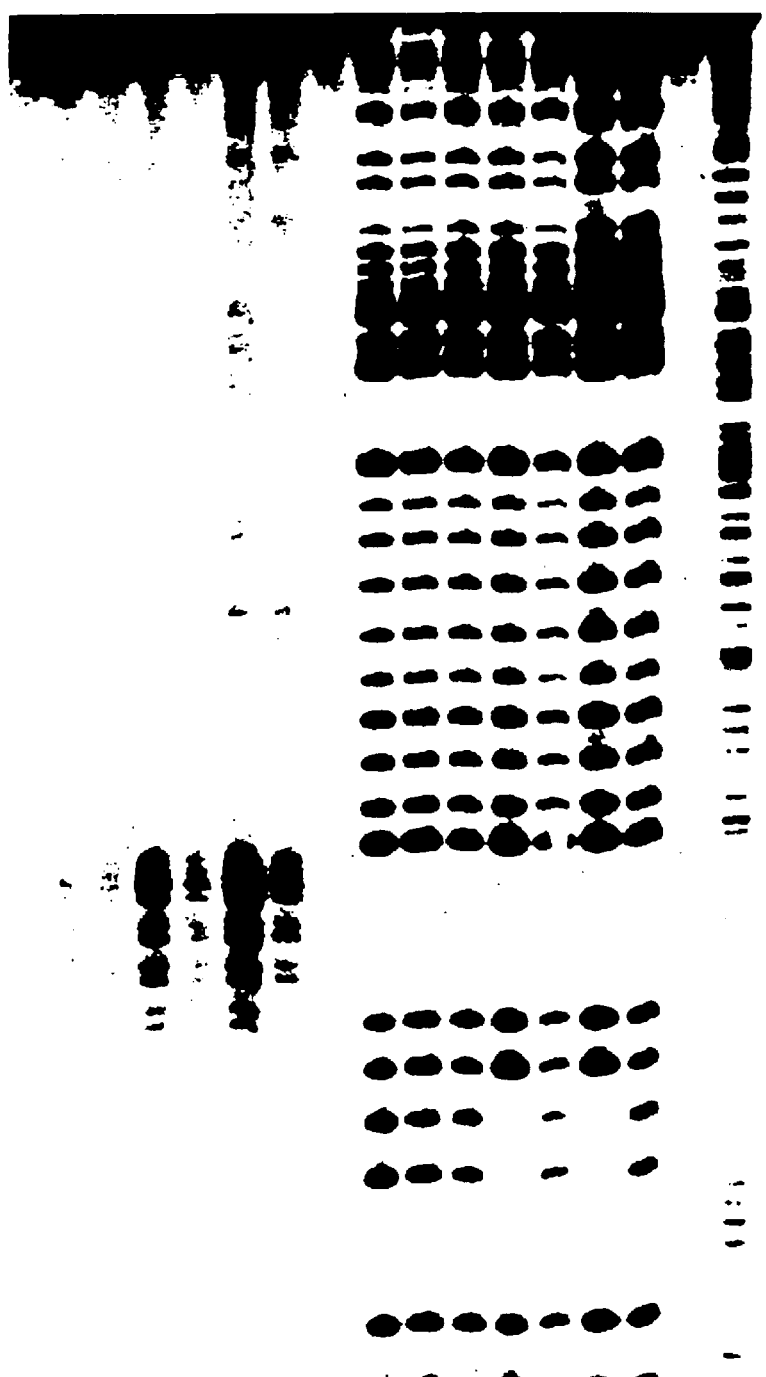
FIG. 12 is a footprinting experiment showing the effect of pH and salt on the binding of a thymine/cytosine containing PNA to double stranded DNA comprising sequences TTTTCTTCTT (SEQ. ID. NO: 64) and AAGAAGAAAA (SEQ. ID. NO:5)

For this example the 264 bp EcorI/PvuII fragment of pT8C2A8G2 was used that was 3'-$^{32}$P-end-labeled at the EcorI sit. Probing was effected as per the protocols of Example 12. The results are shown in FIG. 12 where in lanes 1 & 9 are controls without PNA. Lanes 1–7 are $KMnO_4$ probing while lanes 9–15 are DMS probing. The samples of lanes 2–7 & 9–15 contained 5 μM PNA. The samples of lanes 3, 5, 7, 11, 13 & 15 contained 100 mM NaCl in the 10 mM Na phosphate, 1 mM EDTA buffer. The pH of the buffer was 7.5 (lanes 2, 3 & 10, 11); 6.5 (lanes 4, 5 & 12, 13) or 5.5 (lanes 6,7 & 14, 15). Lanes are A+G sequence markers.

This example shows that the Hoogsteen hydrogen bonding of cytosine to guanine requires protonation of N3 of cytosine and consequently interactions involving $C^+$-G Hoogsteen base pairing are very sensitive to the acidity of the medium. This has been studied extensively by others with DNA triple helices, and can also be seen with $(PNA)_2$/DNA triplexes using oligonucleotides.

The results presented in FIG. 12 further show that the strand displacement binding of PNA $T_2CT_2CT_4$ (SEQ ID NO:1) to the target of pT8C2A8G2 is also sensitive to pH. Very little binding is observed at pH 7.5 (lanes 2 & 10) compared to pH 6.5 (lanes 4 & 12) and 5.5 (lanes 6 & 14). Full consistency is also seen between the $KMnO_4$ and DMS probing results showing clear correlation between strand displacement and Hoogsteen type binding of the PNA. We have previously shown that medium ionic strength (50–100 mM Na$^+$) inhibits strand displacement binding of PNA to double-stranded DNA. The results presented in FIG. 15 (lanes 3, 5, 7) are fully consistent with this. There is no reason from physio-chemical considerations that binding of PNA to DNA as a conventional PNA DNA-DNA triple helix should be strongly salt dependent. Therefore, such complexes could be envisaged under salt conditions that disfavor strand displacement. However, we see no evidence that this be the case since no DMS footprint is observed under "high-salt" conditions (FIG. 12, lanes 11, 13 & 15).

From Examples 13, 14 and 15 as well as other of the Examples of this specification, we conclude that sequence specific binding of PNA to double-stranded DNA involves PNA DNA—DNA triplex s employing conventional Hoogsteen and Watson-Crick base pair hydrogen bonding for recognition.

EXAMPLE 16
Electron Microscopy

A pA98 plasmid containing an $A_{98}/T_{98}$ (SEQ ID NO:42) insert in the PstI site of the polylinker of a pUC 19 plasmid was used. 0.1 μg of the pA98 plasmid linearized by the Cfr1OI I restriction enzyme was incubated with 0.15 μg of PNA H-$T_{10}$-LysNH$_2$ (SEQ ID NO:2) at 37 °C. for 3 hours in 10 μL of the TE buffer (10 mM of Tris-HCl, 1 mM of Na$_3$EDTA, pH 8.0). The complex was diluted with buffer containing 10 mM of Tris-HCl, 10 mM of NaCl, pH 7.5 to the final DNA concentration of 0.2–0.5 μg/mL and absorbed to the surface of glow discharged in tripropylamine carbon grid for 2 minutes as described in Duochet, J., *Ultrastruct. Res.*, 1971 35, 147–167. The grid was stained in 0.1–0.5 % water solution of uranyl acetate for 10–15 sec and dried. The sample was shadowed with Pt/C (95/5) and studied in a Philips 400 electron microscope at accelerating voltage of 40 kV. The length of the DNA molecules were measured and a histogram was plotted as described by A. V. Kurakin in Micron Microscopica Acta, 22,213–221 (1991). The length of unwound region was measured by its thicker strand, for which the number of base pairs per unit length was assumed to be the same as for the DNA duplex. For analysis by use of a histogram, the molecules were oriented in such a manner that the left boundary of the loop was closer to the end of the molecule.

The electron microscopy of the PNA-DNA complex was carried out an the $A_{98}/T_{98}$ (SEQ ID NQ:42) target contained within the supercoiled plasmid, pA98, linearized with the Cfr10I restriction enzyme, and challenged with a PNA H-$T_{10}$-LysNH$_2$ (SEQ ID NO:2). Full occupancy of the target results in a strand displacement loop of 90–100 bases was detected as is shown in FIG. 13. This histogram plot is illustrated in FIG. 14. As is seen in FIG. 13, the DNA molecules carry an open region in the form of "an eye". In all cases one of the two strands in the open region was thicker than the other on and has the same thickness as the normal DNA duplex. The thicker strand corresponds to the A-strand covered by PNA, while the thinner strand corresponds to the displaced T-strand.

The positions of two branch points of the loops were 47.1% and 51.2%, which within the error of EM-measurements (0.5%), coincides with the ends of the A98/T98 (SEQ ID NO:42) insert (47.5% and 51.0%). The average size of the loop was 4.1%, i.e., 114 bp, which also agrees well with the length of the insert( the standard error is 17 bp). In control experiments carried out without added PNA, the eye-like structures were not observed.

EXAMPLE 17
Unwinding of Closed Circular DNA with PNA

Relaxed circular DNA was prepared by treating ordinary supercoiled plasmid DNA with an extract containing DNA topoisomerase I, as described by V. I. Lyamichev, et. al., J. Biomolec. Struct. Dynamics, 3, 327–338 (1985). DNA-PNA complexes were obtained by incubation of 1–2 μg of DNA in 5–20 μL TE with 0.4 optical units./mL of PNA for 4 hours at 20–22° C. This corresponded to about 10 times molar excess of PNA to its potential binding sites. Agarose (1.5%) gel electrophoresis was performed in the TAE buffer containing 1 μg/mL of chloroquine at 10° C. for 15 hours at 1.5 V/cm. Tw—dimensional gel electrophoresis was preformed in the first direction (from top to bottom) in the TAE buffer and in the second direction (from left to right) in the same buffer with addition of 1 μg/mL of chloroquine.

Figure 15:
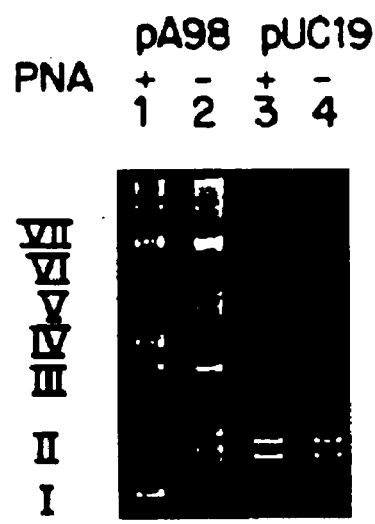
FIG. 15 is a one dimensional gel electrophoresis experiment showing the DNA unwinding upon PNA binding.
Figure 16:
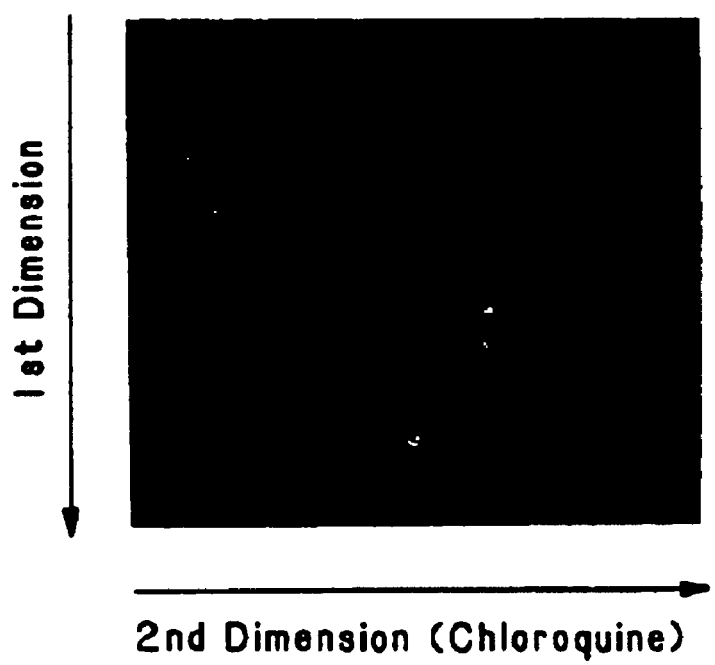
FIG. 16 is a two dimensional gel electrophoresis experiment showing the DNA unwinding upon PNA binding.
Figure 17A:
FIG. 17A shows the salt dependent binding of PNA in a gel electrophoresis experiment.
Figure 17B:
FIG. 17B shows the salt resistance of the PNA-DNA complex in a gel electrophoresis experiment.
Figure 20:
FIG. 20 is an autoradiogram showing the concentration dependence of transcription inhibition by PNA $T_{10}$ (SEQ ID NO: 2)

In this example, the efficiency of PNA T10 incorporating into the DNA duplex and displacing the DNA T-strand in solution was shown by unwinding of closed circular DNA by PNA. The pA98 plasaid (Example 16) was prepared in the form of relaxed circles (rcDNA). It was expected that complexing with PHA would unwind about 10 turns of the DNA duplex. Because of topological constraints (the two strands in rcDNA were closed and therefore topologically linked), this unwinding would make the rcDNA molecules behave as if they were positively supercoiled by 10 superturns. This, would manifest itself in an increase of electrophoretic mobility of the complex as compared with control rcDNA preincubated in the same buffer without PNA. This increase in electrophoretic mobility is shown in FIG. 15 that shows that after incubation with PNA in the low-salt TE buffer for 4 hours at 20° C., virtually all rcDNA molecules significantly increased their mobility and moved as if they were highly supercoiled. Two-dimensional gel electrophoresis gels, FIG. 16, shows that these molecules behave actually as positively supercoiled ones. This technique is used to resolve individual topoisomers. Using a sample with a wide distribution of topoisomers as reference, it is clearly seen FIG. 16 that on the average 8–10 turns of the double helix are released upon binding of PNA. These results indicate that in the TE buffer PNA occupied all available binding sites on the DNA duplex efficiently displacing the DNA T-strand in the A98/T98 (SEQ ID NO:42) insert. When NaCl is added to the incubation buffer, the degree of conversion of rcDNA into rapidly moving species dramatically decreased within a narrow range between 20 and 40 mM of NaCl as seen in FIG. 17, panel A. This emphasizes a strong sensitivity of the PNA incorporation to the salt concentration. However, after being formed at low salt, the complex showed remarkable stability and tolerated increasing salt concentrations up to at least 500 mM of NaCl (FIG. 20, panel B, lane 4). The complex could be dissociated by alkali treatment (FIG. 20, panel B, lane 5).

EXAMPLE 18
Inhibition of RNA Polymerase $T_3$ Transcription Elongation by PNA

Figure 18:
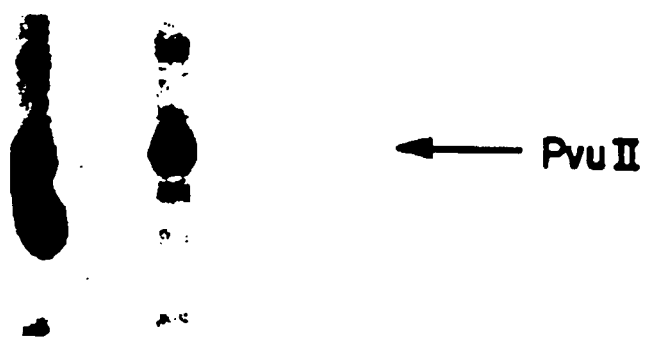
FIG. 18 is an autoradiogram showing sequence selective transcription inhibition by PNA.
Figure 18:
Figure 18:

The complex, between PNA $T_{10}$-LysNH$_2$ (SEQ ID NO:2) (1 or 10 um) and pAIOKS (pBluescriptKS$^+$ in which the d(A$_{10}$) target is cloned into the BamHl site, analogous to pTlO) (100 ng) cleaved with restriction enzyme PyuII, XbaI, or BamHl, was formed by incubation in 14 $\mu$L 10 m Tris-HCl, 1 mM EDTA, (pH 7.4) buffer for 60 min. at 37° C. Subsequently 4 $\mu$L 5× concentrated polymerase buffer (0.2 M Tris-HCl, pH 8.0, 125 mM NaCl, 40 mM MgCl$_2$, 10 mM spermidine) was added together with 15 U $T_3$ RNA polymerase and ATP (10 mM), CTP (10 mM), GTP (10 mM), UTP (1 mM) and $^{32}$P-UTP (0.1 $\mu$Ci), and the incubation was continued for 10 min. Following ethanol precipitation, the RNA was analyzed by electrophoresis in sequencing gels and the radiolabeled bands were visualized by autoradiography using intensifying screens. The results are shown in FIG. 18: Lane 1: pTIOKS was cut with PyuH and no PNA was present. Lane 2: pTIOKS was cut with BamHl, and no PNA was present. Lane 3: pTIOKS was cut with XbaI, no PNA. Lane 4: as in lane 1 but in the presence of PNA (1 uM). Lane 5: as lane 3+PNA (1 uM). Lane 6: as lane 1+PNA (10 uM). Lane 7: as lane 3+PNA (10 uM).

As is seen in FIG. 18, In the absence of PNA the expected run-off transcript is observed (lanes 1, 2 & 3). When the preformed complex between PNA $T_{10}$-LysNH$_2$ (SEQ ID NO:2) and the template was used, a transcript which corresponds in length to transcription arrest at the encounter of the PNA, i.e., on nucleotide longer than the run-off at the BamH1 site (lane 3), is produced (lanes 4–7). This shows that transcription elongation by RNA polymerase $T_3$ is effectively blocked by PNA bound to the template strand. If PNA was bound to the non-template strand, no transcript corresponding to blockage by the PNA was observed. Similar results were also obtained using RNA polymerase $T_7$ (data not shown). In this experiment the PNA/DNA complexes were formed in low salt buffer prior to addition of the buffer required for enzyme action since binding of PNA to dsDNA is inhibited by elevated (>50 mM Na$^+$) salt concentrations. Once formed, the complexes are exceedingly stable to these conditions.

EXAMPLE 19
Inhibition of Taq DNA Polymerase Primer Extension by PNA

Figure 19:
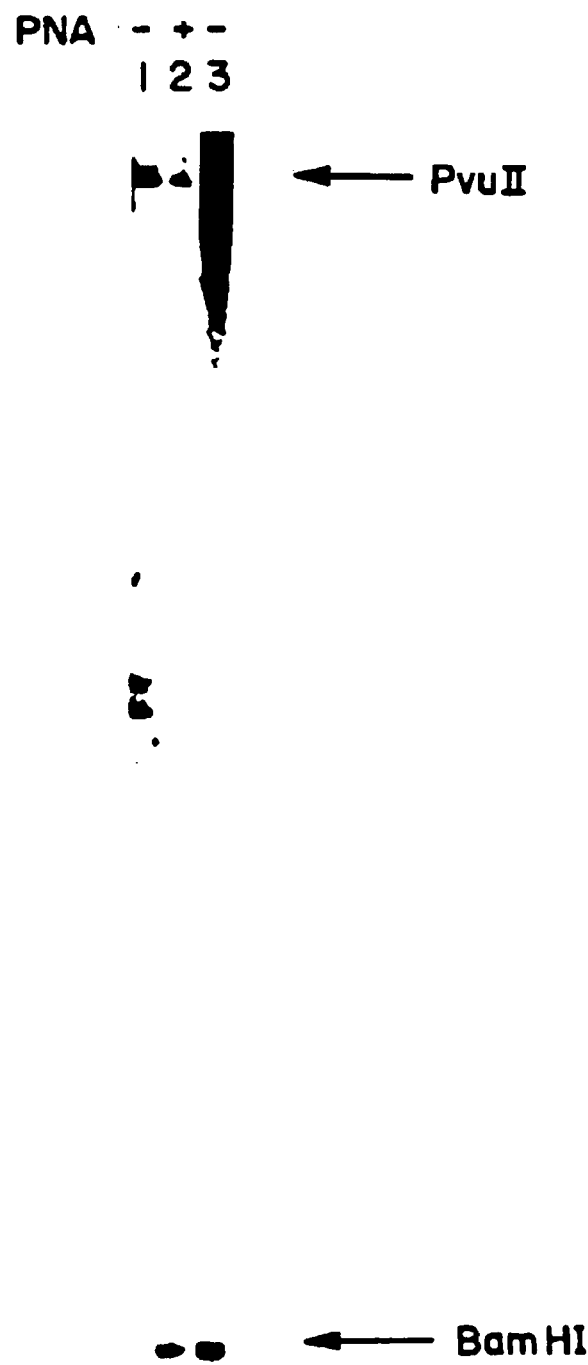
FIG. 19 is an autoradiogram showing sequence specific inhibition of Taq DNA polymerase by PNA.

A mixture of 100 500 ng Pvull cleaved plasmid pAIOKS, 0.1 ug M13 reverse primer and 1 ug of PNA $T_{10}$-LysNH$_2$ (SEQ ID NO:2) in 10 ul buffer (10 ml Tris-HCl, pH 8.3, 50 mM KCl, 1.5 mM MgCl$_2$, 0.1 mg/ml gelatine) was incubated for 5 min at 90° C. and then for 60 min at 37° C. Subsequently, 1 U of Taq polymerase, 1 ul dCTP (100 uM), dGTP (100 uM), dTTP (100 uM) and $^{32}$ P-dATP (1 uCi) were added and the incubation continued for 5 min at 20° C. Following the addition of 2 ul dATP, dCTP, dGTP, dTTP (1 mM each), the sample was incubated for 15 min at 60° C. The DNA was precipitated with ethanol and the samples treated as described for Example 18. The results are shown in FIG. 19: Lane 1: pTIOKS was cut with PvuII and no PNA was present. Lane 2: same as lane one with PNA present. Lane 3: no PNA and PTIOKS was cut with BamHl.

As is shown in this example, in a primer extension experiment using a pre-formed complex between PNA $T_{10}$-LysNH$_2$ (SEQ ID NO:2), a single-stranded target, and a primer down-stream from the target sequence, a product corresponding in length to blockage at the PNA was produced by tag DNA polymerase (FIG. 19, lane 2). No product was detected in the absence of PNA (lane 3). Similar results were obtained using the large fragment (Klenow fragment) of *E. Coli* DNA polymerase (data not shown). Thus demonstrates elongation by DNA polymerases is blocked by PNA.

EXAMPLE 20
Inhibition of Transcription by PNA

The PNA oligomers $T_{10}$-LysNH$_2$ (SEQ ID NO:2), $T_5CT_4$-LysNH$_2$ (SEQ ID NO:6) and $T_2CT_2CT_4$-LysNH$_2$ (SEQ ID NO:1) were synthesized as described in Example 1. Plasmids containing the target sequences were obtained by cloning or the appropriate oligonucleotides into the vector pBluescripKS$^+$. To obtain pT10KS and pA10KS, 16-mers 5'-TCGACT$_4$CT$_5$G (SEQ ID NO:36) and 5'-GATCCA$_{10}$G (SEQ ID NO:34) were cloned into the BamH1 site, and clones containing the insert in either orientation were isolated. pT9CA9GKS was obtained by cloning 5'-TCGACT$_4$CT$_5$G (SEQ ID NO:36) and 5'-TCGACA$_5$GA$_4$G (SEQ ID NO:37) into the SalI site and pT8C2KS and pA8G2KS were obtained by cloning 5'-GT$_4$CT$_2$CT$_2$CTGCA (SEQ ID NO:39) AND 5'-GA$_2$GA$_2$GA$_4$CTGCA (SEQ ID NO:38) into the PstI site. *E. coli* JM103 was used as host in all cases, and transformations and isolation of clones were done by standard techniques. Plasmids were purified by buoyant density centrifugation in CsCl gradients and characterized by dideoxy sequencing.

Inhibition of RNA Polymerase Transcription Longation by PNA

The complex between the desired PNA and the desired DNA (100 ng) cleaved with the desired restriction enzyme was formed by incubation in 14 $\mu$L 10 mM Tris-HCl, 1 mM EDTA, (pH 7.4) buffer for 60 min at 37° C. Subsequently 4 $\mu$L 5× concentrated polymerase buffer (0.2 M Tris-HCl, pH 8.0, 125 mM NaCl, 40 mM MgCl$_2$ 10 mM spermidine) was added together with 15 U of RNA polymerase and ATP (10 $\mu$M), CTP (10 mM), UTP (1 mM) and $^{32}$P-UTP (0.1 $\mu$Ci). The incubation was continued for 10 min. Following ethanol precipitation, the RNA was analyzed by electrophoresis in polyacrylamide sequencing gels, and radialabeled RNA bands were visualized by autoradiography (using Agfa Curix RPI X-ray films and intensifying screens). Quantitation was performed by densitometric scanning using a Molecular Dynamics laser scanner and the ImageQuant™ software.

FIG. 20 illustrates certain concentration dependence between complexes of pA10KS cleaved with XbaI and the following concentrations of PNA $T_{10}$-LsyNH$_2$ (SEQ ID NO:2): 0, 0.2, 0.35, 0.7, 1, 1.4, 1.75, 2.1, 2.8, 3.5, 4.3 or 5 $\mu$M (lanes 1–12). The complexes were formed by incubation in TE buffer for 60 min. at 37° C. The buffer was adjusted to transcription conditions and following the addition of NTPs, $^{32}$P-UTP and T$_3$ RNA polymerase, transcription was allowed to proceed for 5 min. at 37° C. The transcripts were analyzed by electrophoresis in 10% polyacrylamide/7M urea gels and visualized by autoradiography.

Figure 21:
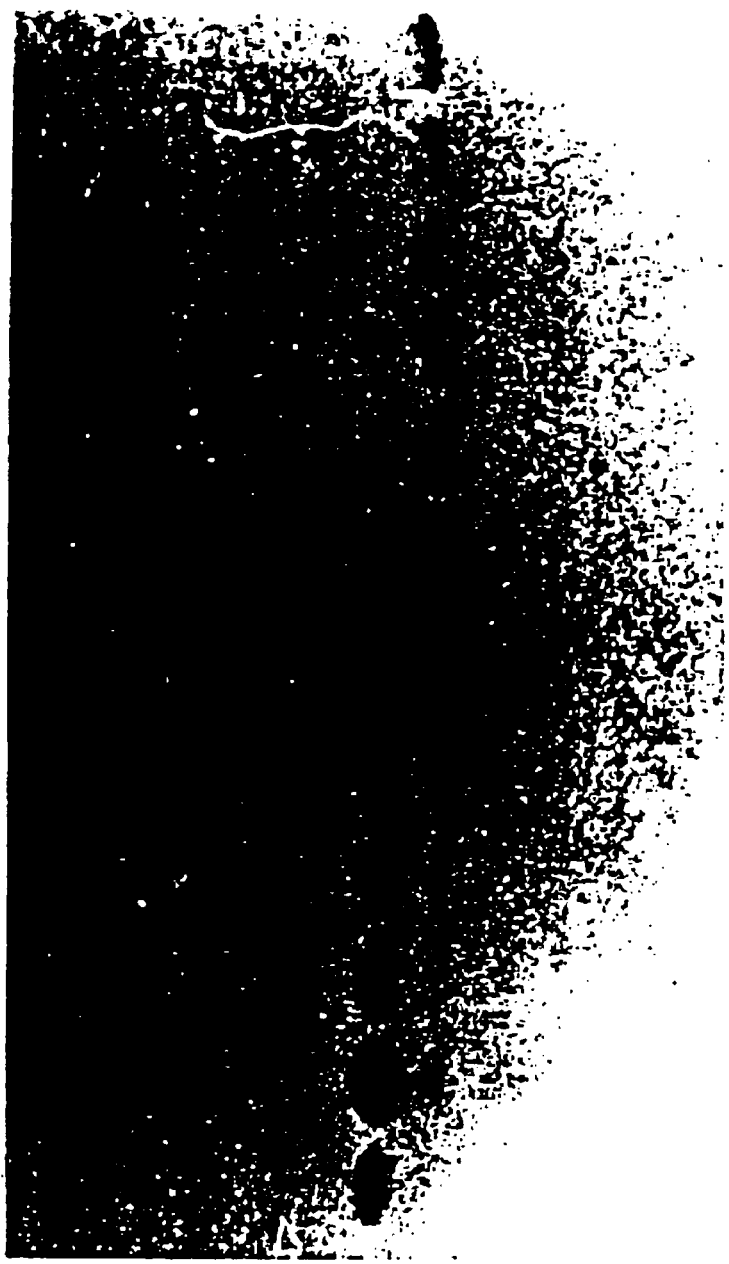
FIG. 21 is a FIG. 20 but using PNA $T_4CT_2CT_2$.

The results shown in FIG. 21 are similar to those of FIG. 20 except that the plasmid pA8H2KS was cleaved with BamH1 and PNA T$_2$CT$_2$CT$_4$-LysNH$_2$ (SEQ ID NO:1) at the following concentrations: 0, 0.6, 1.2, 2.4, 3.6, 4.8, 6, 7.2, 9.6, 14.4 or 16.7 μM (lanes 1–12).

Figure 22:
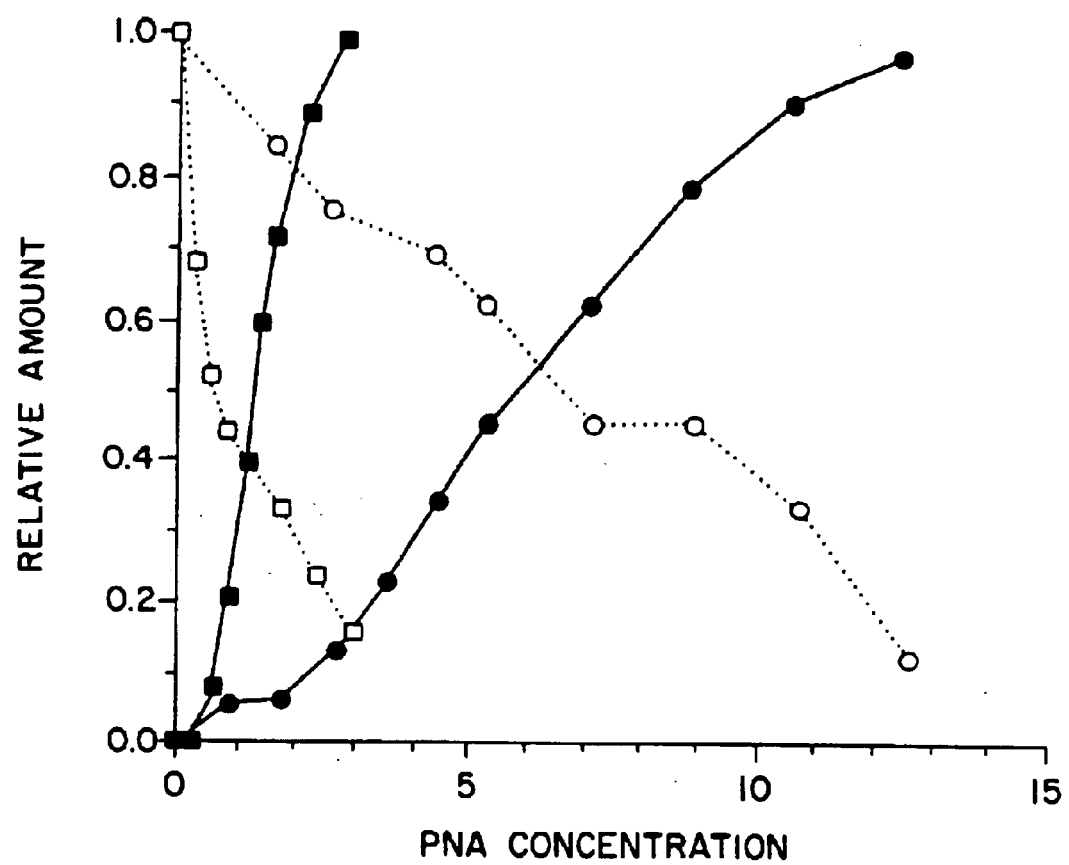
FIG. 22 is a quantitative representation of the results of FIGS. 20 & 21.

FIG. 22 illustrates a quantitative representation of the results shown in FIGS. 20 and 21. In this figure the following symbols, respectively, are utilized, squares: pA10KS× XbaI and PNA T$_{10}$-LysNH$_2$ (SEQ ID NO:2); circles: PA8GKS×BamH1 and PNA T$_2$CT$_2$CT$_4$-LysNH$_2$ (SEQ ID NO:1). closed squares: relative amount of the truncated transcript; closed circles: total amount of transcript.

This examples illustrates that the phage T$_3$ and T$_7$RNA polymerases can be used as a model system for very efficient and robust transcription. In this example, a template was constructed by cloning the appropriate PNA targets into the polylinker of the BluescriptKS$^+$ plasmid. The target was clone into the BamH1 site in both orientations, thus allowing for four transcription experiments to be performed using either the constructs and either the T$_3$- or the T$_7$-promoter. The results presented in FIGS. 20, 21 and 22 show the dose dependent inhibition of the transcription of pA10KS (FIG. 20) or pA8G2KS (FIG. 21) by PNA T$_{10}$-LysNH$_2$ (SEQ ID NO:2) or T$_2$CT$_2$CT$_4$-LysNH$_2$ (SEQ ID NO:1) using T$_3$ RNA polymerase. It is observed that as the concentration is raised the amount of full length transcript is decreased and the amount of truncated product is increased suggesting that sequence specific transcription arrest is taking place. However, the total amount of transcript also decreases indicating that general inhibition of transcription also occurs.

EXAMPLE 21

Figure 23:
FIG. 23 is an autoradiogram showing the results of transcription arrest using various PNA and RNA polymerases.

Sequence Specificity of the Transcription Elongation Arrest by PRA T$_{10}$-LysNH$_2$ and PNA T$_2$CT$_2$CT$_4$-LysNH$_2$ using T$_3$ or T$_7$ RNA Polymerase Samples identical to those used for Example 20 were analyzed by electrophoresis in a polyacrylamide sequencing gel. The results are shown in FIG. 23 where, Lanes 1–4: pA10KS/T$_3$ RNA polymerase; lanes 5–8: pT10KS/T$_7$ RNA polymerase; lanes 9–12: pA8G2KS/T$_3$ RNA polymerase lanes 13–16: pT8C2KST$_7$ RNA polymerase. The plasmid used in the samples of lanes 1–3 was cleaved with XbaI, that in lanes 6–8 with Pst1, that in lanes 9–11 with BamH1 and that in lanes 14–16 with HindIII. Lanes 1, 8, 9 & 16 are controls without PNA. Lanes 4, 5, 12 & 13 are controls cleaved proximal to the PNA target site i.e., with BamH1 (lanes 4 & 5) or Pst1 (lanes 12 & 13). Samples of lanes 2, 3, 6 & 7 were preincubated with PNA T$_{10}$-LysNH$_2$ (SEQ ID NO:2), and those of lanes 10, 11, 14 & 15 were preincubated with PNA T$_2$CT$_2$CT$_4$-LysNH$_2$ (SEQ ID NO:1).

In this example, in order to determine the position of transcription arrest, RNA transcripts were analyzed on high resolution sequencing gels. The results show that a specific RNA transcript is produced by T$_3$-RNA polymerase in the presence of PNA-T$_{10}$ (SEQ ID NO:2) that is one nucleotide longer than the run-off transcript produced using a template (BamH1 cleaved) ending one nucleotide in front of the PNA target (FIG. 23, lanes 2–4). Thus transcription proceeds to, but does not include, the first nucleotide involved in hydrogen bonding with the PNA. The results obtained with T$_7$-RNA polymeras are similar to those with T$_3$-RNA polymerase (FIG. 23, lanes 5–8). Interestingly, however, in this case the transcript is less homogeneous in length than the transcript obtained with the T$_3$-polymerase, and the lengths of the transcripts indicate that the polymerase is able to transcribe into the PNA target. These results show that this polymerase is able to some extent to displace the bound PNA during transcription, although the polymerase-PNA encounter may sometimes result in chain termination. Using mixed A/G PNA targets gave the results shown in FIG. 23, lanes 9–16. It is noteworthy that transcription arrest with an A$_4$GA$_5$ (SEQ ID NO:43) target and a T$_4$CT$_5$-LysNH$_2$ (SEQ ID NO:8) PNA occurs one to two nucleotides inside the target, while transcription arrest with an A$_4$GA$_2$GA$_2$ (SEQ ID NO:44) target and a T$_4$CT$_2$CT$_2$-LysNH$_2$ (SEQ ID NO:9) PNA is much less efficient (as compared to the results of Example 22) and occurs at the end of the target (FIG. 23, lanes 10, 11, 14 & 15).

EXAMPLE 22

Transcription Arrest in pT9CA9GKS Plasmid

Figure 24:
FIG. 24 is a continuation of FIG. 23.

In FIG. 24 the effect of PNA T$_{10}$-LysNH$_2$ (SEQ ID NO:2) (lanes 1, 2, 4 & 5) on T$_7$ RNA polymerase transcription of pT10KS (lanes 1–3) and pA10KS (lanes 4 & 5), and of PNA T$_5$CT4- LysNH$_2$ (SEQ ID NO:6) (lanes 6, 7, 10 & 11) on T$_3$ or T$_7$ RNA polymerase transcription of pT9CA9GKS (lanes 6–11) are shown. The plasmid of the samples in lanes 1, 2, 4–7, 10 & 11 were cut with PvuII while BamH1 was used for the sample of lane 3, and SalI was used for the samples of lanes 8 & 9. The PNA concentration was 5 μM.

As is shown in this example, experiments using the pT9CA9GKS plasmid and T$_3$ or T$_7$ RNA polymerase showed (FIG. 26, lanes 5–11) that transcription arrest at this PNA target occurred 2–3 bases inside the target. Employing a gel-retardation assay, it was ascertained that the complexes between PNAs T$_{10}$-LysNH$_2$ (SEQ ID NO:2), T$_4$CT$_5$-LysNH$_2$ (SEQ ID NO:8) or T$_4$CT$_2$CT$_2$-LysNH$_2$ (SEQ ID NO:9) with their complimentary dsDNA targets are stable for at least 15 min when transferred from the TE-buffer to the transcription assay-buffer, thus eliminating the possibility that the PNA was dissociating spontaneously during transcription. These results indicate that an increase in the G-content of the target, and thus in the C-content of the PNA decreases the efficiency of transcriptional arrest due to read-through. In all cases it is also observed that PHAs at higher concentrations result in an unspecific inhibition of transcription by T$_3$ or T$_7$ RNA polymerase. We cannot say if this effect is due to an inhibitory effect of the PNA directly at the polymerase, or if it is caused by binding of the PNA to other sites on the DNA template, e.g., the promoter.

EXAMPLE 23

Figures 25A, 25B, 25C:
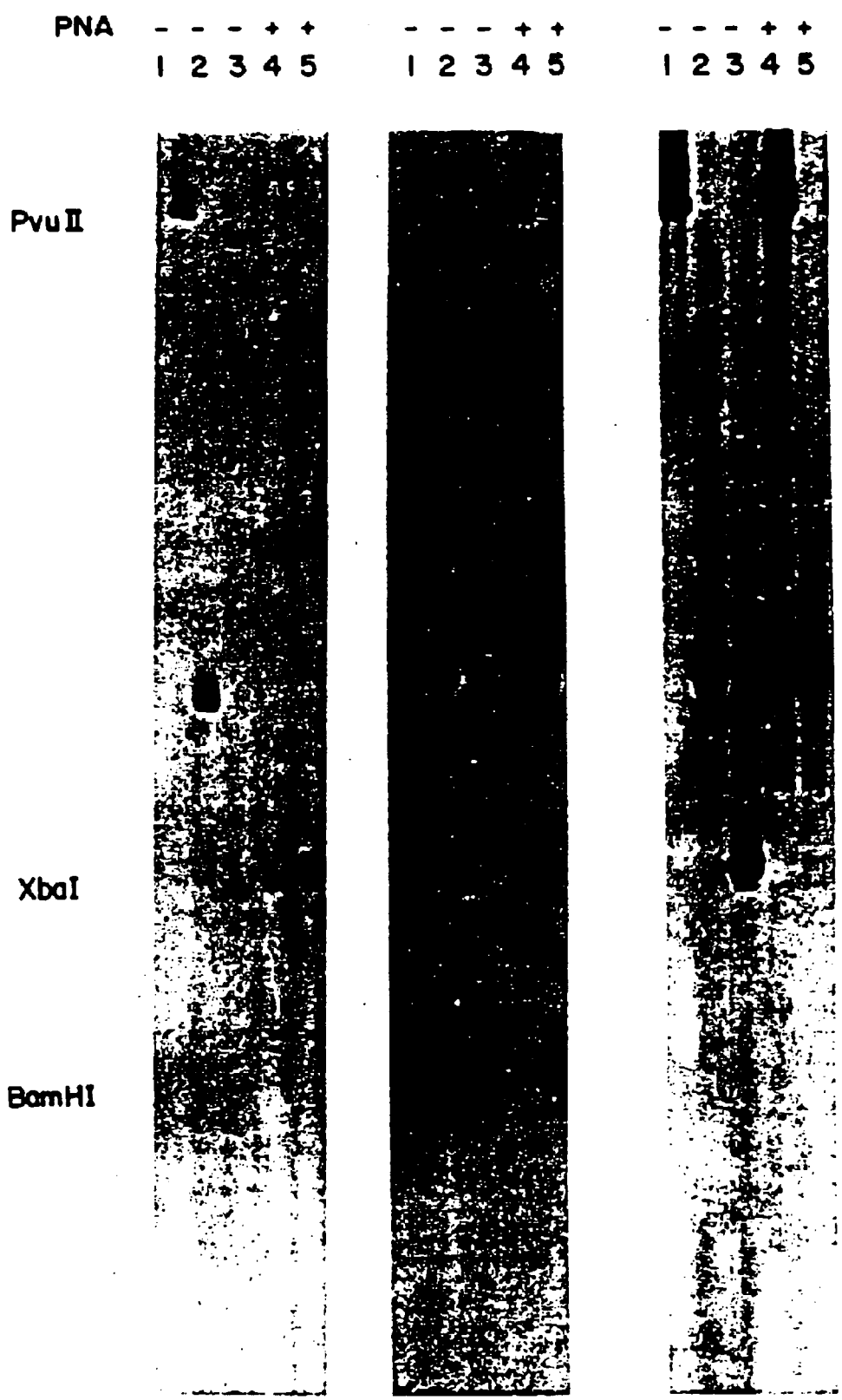
FIG. 25 is an autoradiogram showing the specific effect on transcription of PNA bound to the template versus the non-template strand.

Sequence Specificity of the Transcription Elongation Arrest by PNA T$_{10}$-LysNH$_2$ In this example, template versus non-template binding of the PNa was examined. The experiments were performed essentially as described for Example 21. The results are shown in FIG. 25 using plasmid pA10KS (a & c) or pT10KS (b) cleaved with PvuII (lanes 1 & 4), XbaI (lanes 2 & 5) or BamH1 (lane 3). PNA T$_{10}$-LysNH$_2$ (SEQ ID NO:2) was present at 3.3 μM in the samples of lanes 4 & 5. Panel c is a longer exposure of panel a.

As is shown in FIG. 25, if the PNA is bound to the non-template strand transcription is virtually not arrested (FIG. 25, FIG. 24: lanes 1–5). A very weak band corresponding to arrest at the end of the PNA target can be detected upon longer exposure of the autoradiogram (FIG. 25, panel c, lanes 4,5). These findings are similar to results reported with DNA templates site specifically modified with covalent psoralen adducts.

EXAMPLE 24

Sequence Specificity of the Transcription Elongation Arrest by PNA $T_6$, $T_7$ or $T_{10}$-LysNH$_2$ using pA10KS/T$_3$ RNA Polymerase In this example transcription arrest with PNAs shorter than 10 mers was examined. For the results shown in FIG. 26, the plasmid was cleaved with XbaI in all cases and preincubated with PNA $T_6$-LysNH$_2$ (SEQ ID NO:7) (µM, lane 2), $T_7$-LysNH$_2$ (SEQ ID NO:45) (µM, lane 3) or $T_{10}$-LysNH$_2$ (SEQ ID NO:2) (µM, lane 4). Lane 1 is a control without PNA.

Figure 26:
FIG. 26 is an autoradiogram showing transcription arrest by short ($T_6$&$T_8$) PNAs.
Figure 26:

The results seen in FIG. 26 show that an 8-mer and even a 6-mer PNA, although less efficiently, are able to arrest transcription by $T_3$-RNA polymerase. The results also show that the arrest is occurring with the PNA bound at the far end of the target indicating that the PNA is binding to the 10-mer target in a floating mode and that the RNA polymeras is "pushing" the PNA.

EXAMPLE 25

Transcription Initiation from PNA-DNA Displacement Loops

Figure 27:
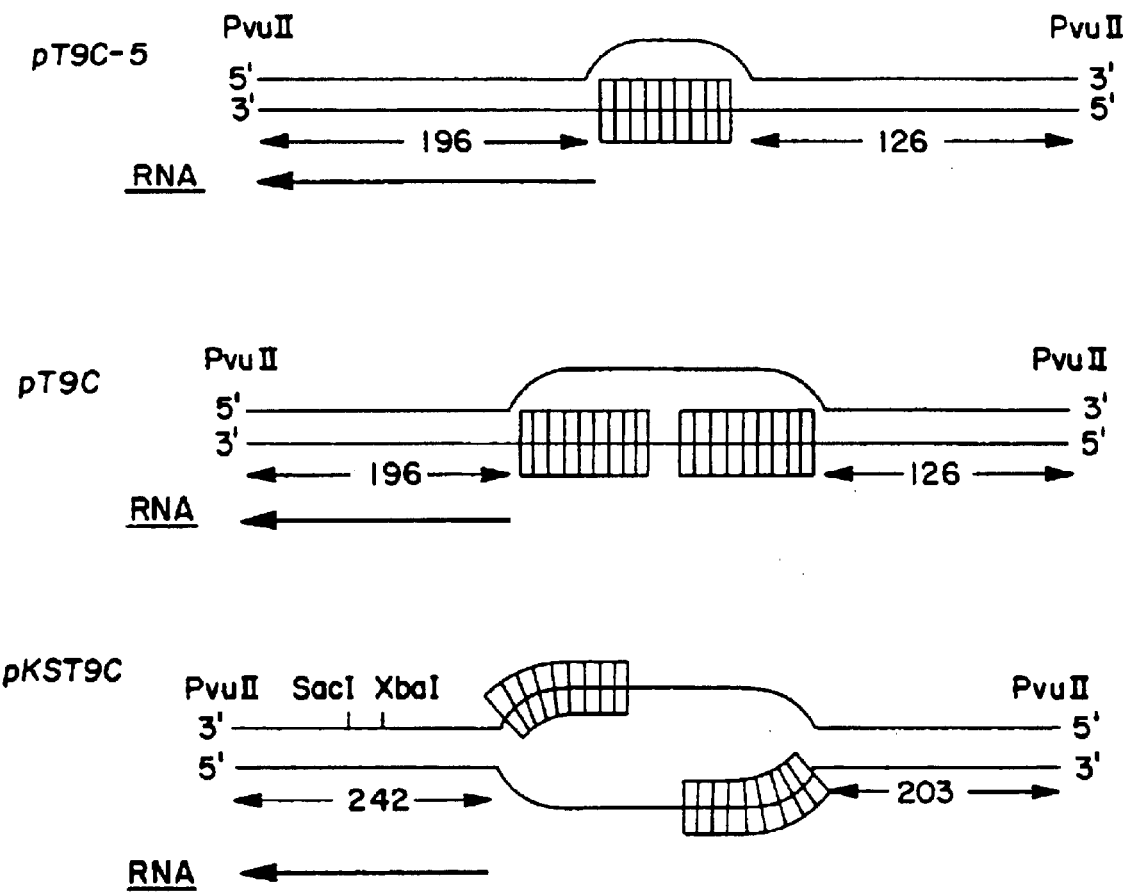
FIG. 27 is a schematic drawing of PNA-DNA transcription initiation complexes.

Peptide nucleic acid (PNA) form (PNA)$_2$/DNA, DNA triplex-D-loop structure upon binding to complimentary double-stranded DNA as shown schematically in FIG. 27. If two adjacent PNA sites are present in cis or in trans (wherein cis is where two PNA bind adjacent to each other on the same strand and trans is where the two PNA bind on opposite strands), structures of the type shown in FIG. 27 b,c are formed. In this example, since these structures resemble transcription elongation loops we tested if *E. coli* RNA polymerase is able to recognize and bind to such PNA/DNA loops.

Figure 28:
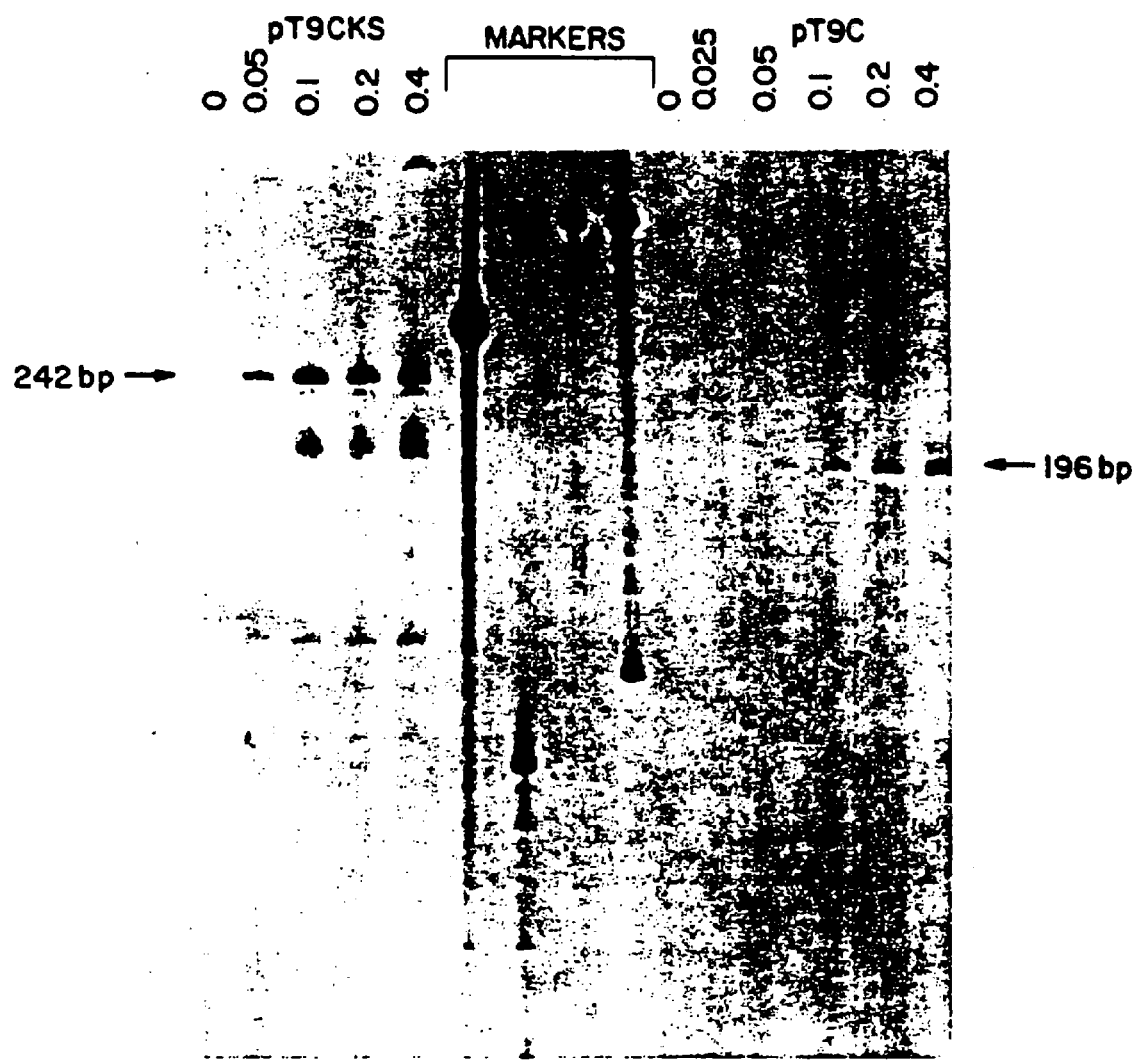
FIG. 28 is an autoradiogram showing transcription initiation by PNA.

The three plasmids pT9C, pT9CT9C (pUC$_{19}$ derivatives) and pT9CA9GKS (Bluescript derivative) were used for this in vitro transcription experiments. Restriction fragments were isolated by digestion with PvuII and on polyacrylamide gels resulting in the fragments shown in FIG. 28. In addition, the isolated PvuII fragment from pKST9C was restricted with XbaI or SacI before PNA hybridization to obtain a shorter transcript from the 'PNA-promoter'. PNA-DNA complexes were formed by combining 0.3, µ PNA (50 OD) with DNA fragments in 10 mM Tris-HCl pH 8.0 and 0.1 mM EDTA in a total volume of 25 µL for 1 hour at 37° C. The transcription were initiated by addition of 50–100 mm *E. coli* RNA Polymerase holoenzyme, T3 and T7. The reaction mix contained a final concentration of: 40 mM Tris-HCl pH 8.0, 120 mM KCl, 5 mM MgCl$_2$, 0.1 mM DTT and 1 mM of ATP, CTP, GTP and 0,1, mM of UTP and $^{32}$P UTP. The complete mixture of 30 ul were incubated at 37° for 20 minutes followed by ethanol precipitation. The RNA transcripts were analyzed on 8% denaturing polyacrylamide gels, and visualized by autoradiography. The RNAse H experiment was done by hybridization of a complimentary oligonucleotide to the MRNA to synthesize a double-stranded target for RNAse H.

EXAMPLE 26

Cis Competition between the PNA Promoter and lacUV5

A PvuII fragment including a single or a triple PNA binding site together with the lac UV5 promoter was isolated. The DNA was incubated with increasing amounts of PNA for 1 hour. The transcriptions were performed as described in Example 25. As indicated by the gel-shifts shown in FIG. 29, a slower migrating complex between the target DNA and the RNA polymerase is formed only if a PNA binding to this target is formed is prebound to the DNA.

EXAMPLE 27

RNA Polymerase Footprinting

Figure 29:
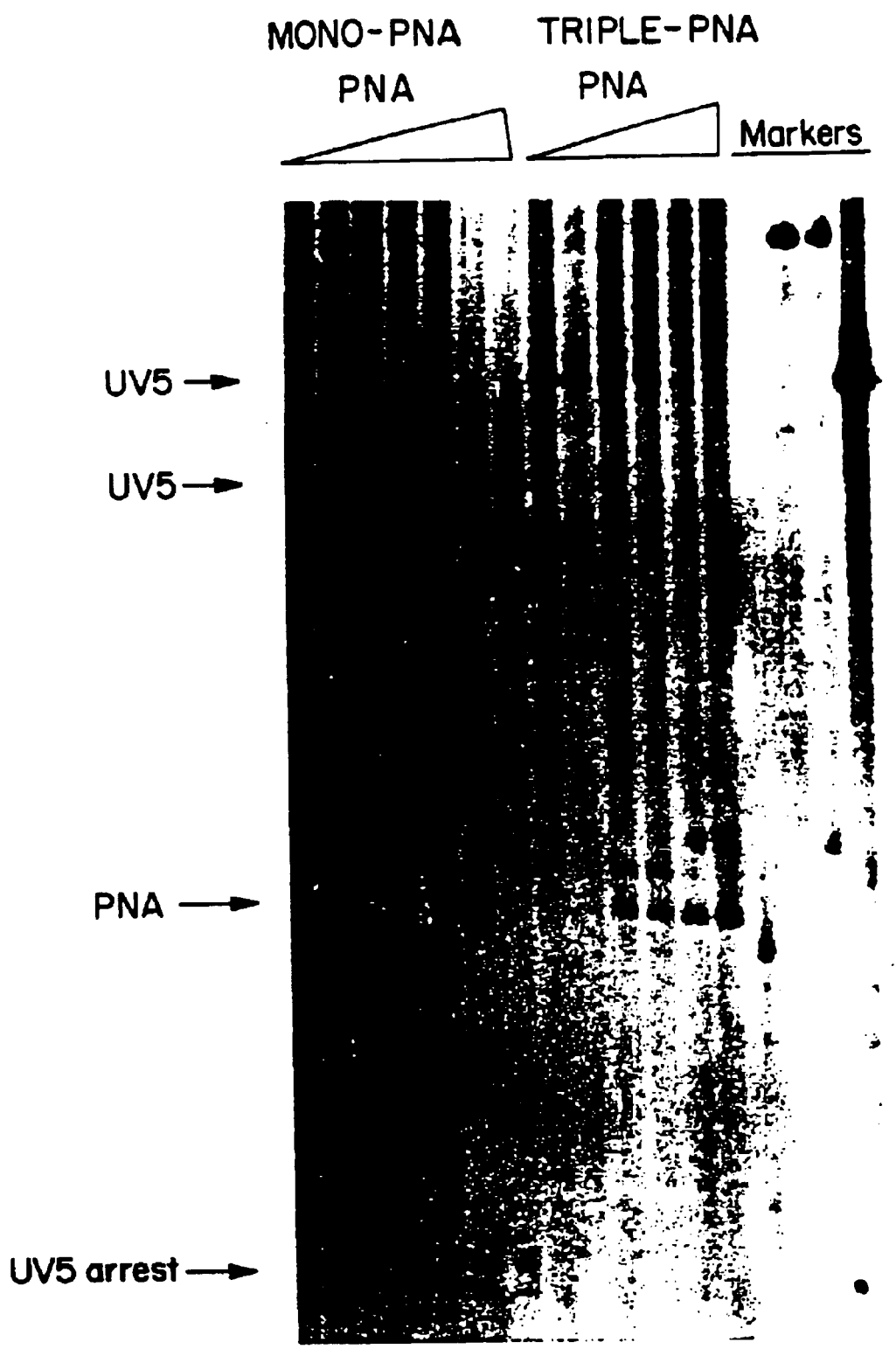
FIG. 29 is an autoradiogram showing the efficient competition of a "PNA promoter" versus the strong lacUV5 promoter.
Figure 30:
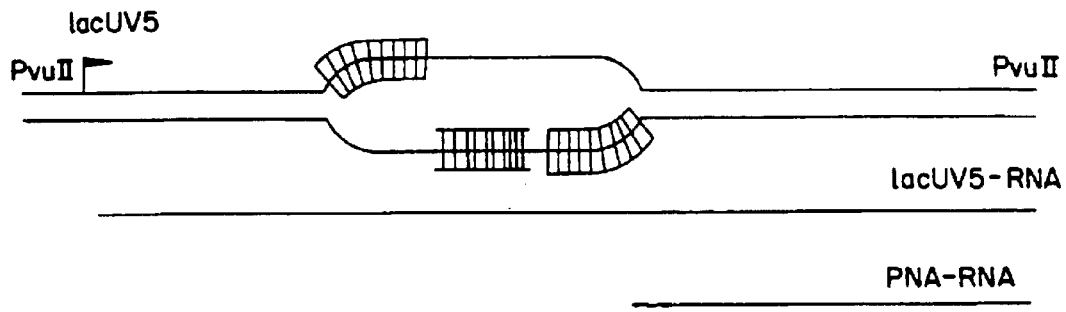
FIG. 30 illustrates schematic structures of PNA/DNA complexes and sequences of the PNA targets.

In this example DNase I footprinting experiments are undertaken to define where on the DNA fragment binding takes place. DNA fragments of the length shown in FIG. 30 are labeled in the 3' end with klen w polymeras and $^{32}$P-dXTP. The PNA-DNA complexes are formed as described in Example 26 above. The RNA Polymerase-PNA/DNA complexes are formed in a reaction buffer as described for Example 26 with the addition of 2 ug/ml calf Thymus DNA in a total volume of 100 ul. After 15 min. incubation at 37° C. the samples are digested with 0.03 µL DNAse (1 mg/ml) for 3 min followed by ethanol precipitation and analyzing by 8% denaturing PAGE. Expected results of this example are also shown in FIG. 29. In the presence of PNA but in the absence of RNA polymerase only a weak footprint corresponding to PNA binding to the target is observed. However, upon addition of *E. coli* RNA polymerase a clear footprint is observed.

EXAMPLE 28

Gel-Shift Assay

PNA-DNA complexes are formed as for the footprint experiment in Example 27. After 15 min at 37° C. incubation the samples are analyzed on 5% PAGE. The gel-shift and DNaseI footprinting results should demonstrate that *E. coli* RNA polymerase binds to a PNA/dsDNA strand displacement loop. The binding should differ distinctly from that seen for RNA polymerase in the initiation and in the elongation complex. Binding in case of the PNA/DNA complex likely will be confined to the DNA loop and will not extend much into the surrounding double-stranded DNA.

Although the (PNA)$_2$/DNA,DNA triplex-D-loop structurally does resemble an RNA transcription elongation loop, it differs in one important aspect; the PNA does not contain a 3'-hydroxyl group to be used as an elongation substrate for RNA polymerase. Nevertheless, PNA dependent transcription is observed from a DNA molecule containing a PNA target. Furthermore, the length of the resulting transcript should corresponds to a run-off transcript initiated at the bound PNA, as exemplified in FIG. 27a. The transcription should be more efficient if a double PNA target is used giving rise to a loop of approximately 30 bases (FIG. 27b) in the cis configuration, and approximately 16 bases in the trans configuration (FIG. 27c). In the latter case, transcripts of two distinct sizes should be produced (FIG. 27c), which in length corresponds to initiation at both. PNA targets and proceeding in opposite directions (FIG. 27c).

Two experiments will be undertaken to estimate the strength of the PNA dependent transcription initiation. In one experiment, both the PNA target and the strong CAP independent UV5 promoter are present on the same DNA fragment. Upon titration with PNA the full run-off transcript from the UV5 promoter is inhibited, while a new transcript corresponding to transcription arrest at the PNA site appears. A very faint band of a length corresponding to transcription initiated at the PNA site is also observed. However, when a DNA fragment containing a triple PNA binding site is used, transcription from this "PNA-promoter" should be able to compete fully with the UV5 promoter. As the PNA concentration is increased, transcription from the UVS promoter decreases with concomitant increase in the amounts of two transcripts that correspond in length to the products expected for transcription in either from the "PNA-promoter". An analogous experiment should be performed in trans using a mixture of a UVS containing DNA fragment and either of the DNA fragments containing the single or the cis or trans double PNA targets. The results of these experiments should confirm that a single PNA decamer target is not able to compete with the UV5 promoter whereas both of the dimeric targets competes very efficiently. While we do not want to be bound by theory, the results should suggest that a single-stranded DNA loop is a major structural determinant for RNA polymerase upon transcription initiation and elongation.

EXAMPLE 29

Figure 31:
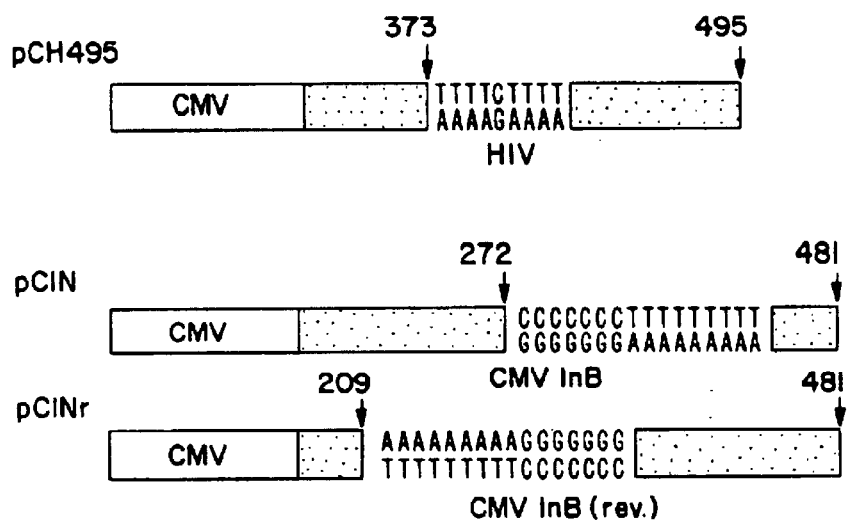
FIG. 31 is a plasmid map wherein pCH495 comprises a sequence TTTTCTTTT (SEQ. ID. NO: 86); pCIN comprises a sequence CCCCCCCTTTTTTTTT (SEQ. ID. NO:87); pCINr comprises a sequence AAAAAAAAAGGGGGGG (SEQ. ID. NO: 88); pIE72 comprises sequences CCCTTC-CTCC (SEQ. ID. NO:69) and TCTCTCTCTT (SEQ. ID. NO: 71)
Figure 31:
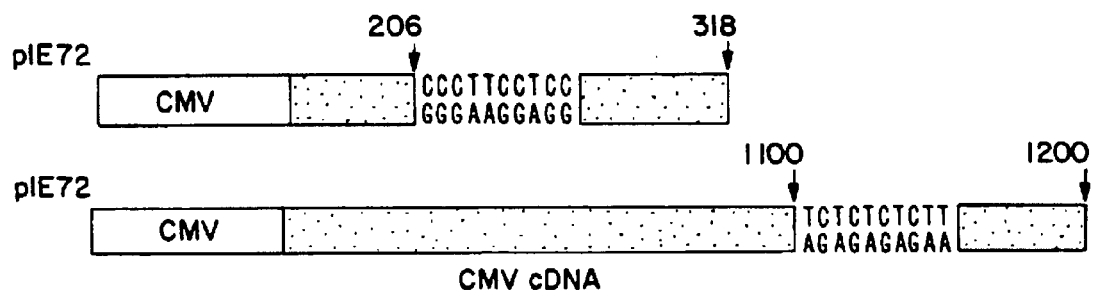

Bite Specific Termination of In Vitro Transcription in Eukaryotic Nuclear Extracts PNA TTTTCTTTT-NH$_2$ (SEQ ID NO:16), TTCCCTTCC-LysNH$_2$ (SEQ ID NO:12), CCCCCCTTTTTTTTT-NH$_2$ (SEQ ID NO:18), TTCTCTCTCT-NH$_2$ (SEQ ID NO:20) and CCTCCTTCCC-NH$_2$ (SEQ ID NO:19) were synthesized as described in Example 1. Phosphodiester oligonucleotides were synthesized using standard protocols as for example Vickers, T. et. al., Nucleic Acids Research, 1991, 19, 3359–3368. Plasmids were constructed with the CMV IE 1 promoter driving the transcription of viral DNA sequences. The plasmid pIE72 is a CMV IE cDNA clone which was constructed as described by Stenberg, M. et. al., J. Virol., 1993, 64, 1556–1565. pCH495 was constructed by ligating the 495 bp SalI/EcoRI fragment from the plasmid pBH10 (see Hahn, B., et. al., Nature, 1984, 312, 166–169) into the vector pUC-CKV, prepared by digestion with the same two enzymes. pCIN was constructed by ligating a 463 bp PvuII fragment from the plasmid pSVCC$_3$ (see Depeto, A. S. and Stenberg, R. M., J. Virol., 1989, 63, 1232–1238), a genomic CMV clone, into the vector pCEP-4 (Invitrogen) linearized at the PvuII site. pCINr was constructed in the same manner, however the insert is cloned in the opposite orientation. The plasmids are illustrated in FIG. 31. All plasmids were constructed with the CMV IE1 promoter (open box) driving the transcription of sequences containing homopurine sites for targeting with homopyrimidine PNA. pCH495 contains a 495 bp SalI/EcoRI fragment from pBH10 (3738 to 4233 of the HIV-1 genome). The plasmid pCIN contains a 463 bp PvuII fragment subcloned from the plasmid pSVCC3, a genomic CMV clone. pCINr contains the same fragment in the opposite orientation. pIE72 is a CMV IE1 cDNA clone. The filled boxes represent the transcribed region of each linearized plasmid. The expected transcript length is shown at the 3' end of each. The sequence of the PNA target site is also shown along with the position relative to the end of the transcript. In vitro transcription 100 ng/ul of linearized plasmid was pre-incubated with PNA at various concentrations in a volum of 10 ul for 3 hours at room temperature in KCl buffered with 10 mM HEPES, pH 6.8. For studies on pH dependence, KCl was buffered with 10 mM TrisOAc, pH 5.1 or 10 mM Tris-HCl, pH 7.9. KCl ranged in concentration from 0.5 to 100 µM. Following the pre-incubation, 2 ul of the PNA bound plasmid was transcribed in HeLa nuclear extracts (Promega) following the manufacturer's protocol. The transcribed RNA's were precipitated then separated by electrophoresis through 5% denaturing acrylamide gels., run 2 hours at 15W. Gels were then dried and exposed to film. Bands on the exposed film were quantitated using a Molecular Dynamics laser densitometer.

Figure 32:
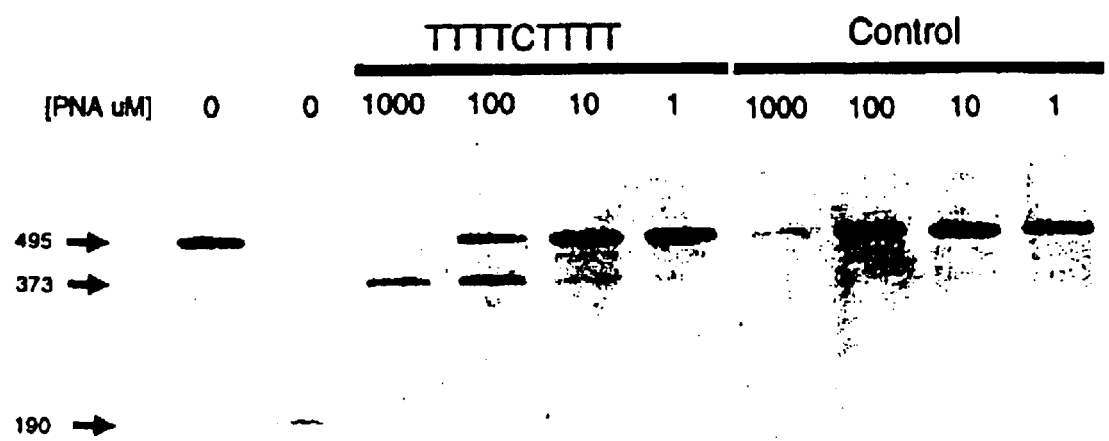
FIG. 32 shows a PAGE autoradiography illustrating site specific termination of in vitro transcription.

A PNA with the sequence TTTTCTTTT-NH$_2$ (SEQ ID NO:16) and a non homologous PNA control were pre-incubated with the 200 ng of EcoRI linerized plasmid pCH495 at the indicated concentrations for 3 hours at 22° C. in 10 ul of 10 mM KCl, pH 6.8 (potassium salt was used in all binding buffers because it is the most compatable with the transcription extract). Following the pre-incubation, the PNA bound plasmid was transcribed in HeLa cell nuclear lystates (Promega) containing $^{32}$P GTP. The transcribed RNA product was then electrophoresed on a 5% acrylamide gel with 50% w/v urea, which was then dried and exposed to film. The expected size of the full length run off transcript and the PNA truncated transcript are shown in FIG. 31. The concentration at which 50% of the transcript was truncated was determined to be approximately 80 uM by quantitating the bands from the exposed film using a Molecular Dynamics densitometer. Results are shown in FIG. 32. Linearization of the plasmid with EcoRI and PvuII provides transcription templates with expected run-off transcripts of 495 (lane 1) and 190 (lane 2) nucleotides respectively. In the presence of the complementary PNA, the EcoRI linearized plasmid yields two distinct transcripts, one corresponding to the run-off transcript and a second truncated transcript with a molecular weight consistent with the 373 nucleotide product expected if truncation occurred at the PNA binding site. The relative proportion of the truncated nucleotide product increases with increasing concentration of PNA in the pre-incubation. When a DNA oligonucleotide of the same sequence (5'-TICTTTT-3') (SEQ ID NO-16) was used in place of the PNA no truncated product was observed (data not shown). The experiment was repeated for the other PNA target sites shown in FIG. 31. These results are shown in Table I and are given as IVT$_{50}$; the PNA concentration at which 50% of the transcript is specifically truncated. All pre-incubations were carried in 10 mM KCl at pH 5.1, 6.8, or 7.9. In all cases, the amount of transcript, both full length and truncated, decreases with increasing PNA concentration, suggesting a non-specific inhibition of transcription by PNA. This effect seems to be become more pronounced as the percentage of cytosine residues in the PNA increases. For example, at a PNA concentration of 1 mM, the total yield of transcript is reduced approximately 63 percent in the presence of PNA TTTTCTTTT-NH$_2$ (SEQ ID NO:16), 84 percent in the presence of TTCTCTCTCT-NH$_2$ (SEQ ID NO:20) and completely in the presence of CCCCCCTTTTTTTTT-NH$_2$ (SEQ ID NO:18) (compare the 1 mM lanes in FIG. 32 and FIG. 33. Direct addition of PNA to transcription extracts did not result in the production of any truncated product (data not shown).

TABLE I

Summary of In Vitro Transcription Activity for PNA Oligomers.

TABLE I

Summary of in vitro transcription activity for PNA oligomers.

| PNA | plasmid | pH 5.1 | pH 6.8 | pH 7.9 |
| --- | --- | --- | --- | --- |
| TTTTCTTTT-NH$_2$ (SEQ ID NO:16) | pCH495 | 58 uM | 76 uM | >500 uM |
| TTCTCTCTCT-NH$_2$ (SEQ ID NO:20) | pIE72 | 29 uM | 103 uM | >1 mM |
| CCCCCCTTTTTTTTT-NH$_2$ (SEQ ID NO:18) | pCIN, pCINr | 30 uM | 124 uM | >1 mM |
| CCTCCTTCCC-NH$_2$ (SEQ ID NO:19) | pIE72 | >1 mM | none | none |

EXAMPLE 30

Effect of Target Site Orientation on PNA Mediated Termination of In vitro Transcription.

Figure 33:
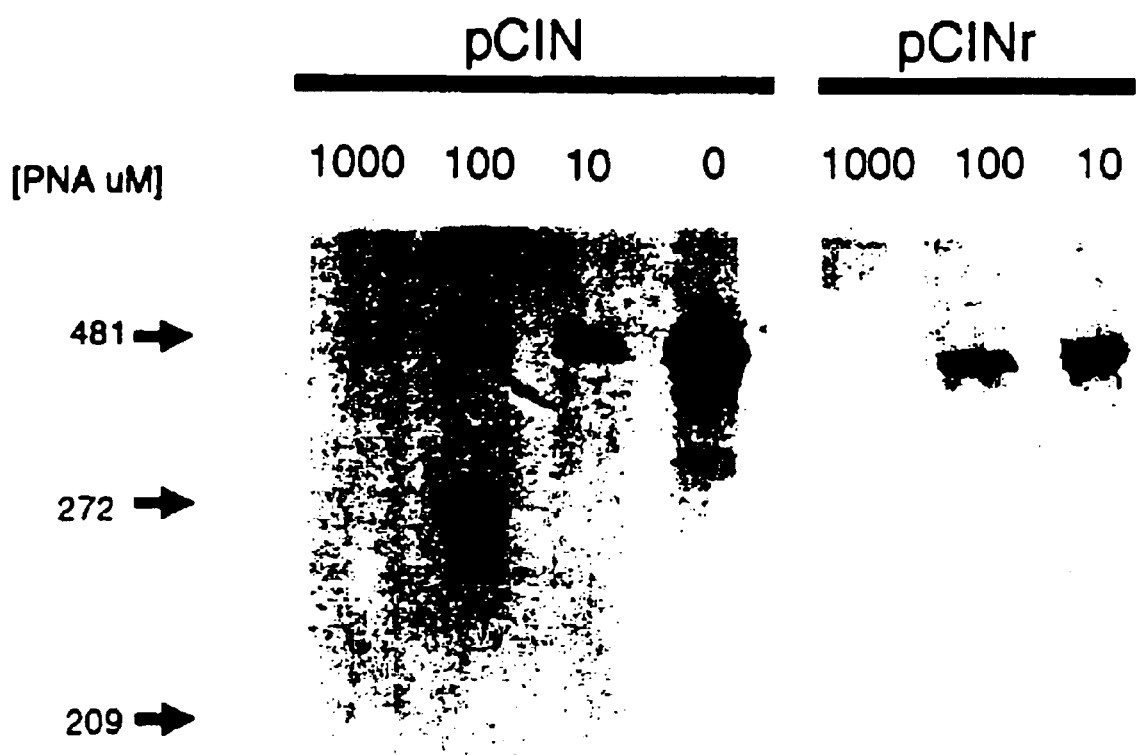
FIG. 33 shows a PAGE autoradiography the effect of target site orientation on PNA mediated termination of in vitro transcription.

Plasmids pCIN and pCINr were linearized with HindIII, then pre-incubated with PNA of the sequence CCCCCCTTTTTTTTT-NH$_2$ (SEQ ID NO:18) at the concentrations shown in FIG. 33 under the conditions described for Example 29. Following the IVT a truncated product was clearly observed for pCIN, where the PNA is bound to the template strand. However, for pCINr, where the PNA is bound to the non-transcribed strand, only a slight amount of truncated product of the expected size is observed. The plasmids pCIN and PCINr contain a CMV gene fragment cloned in opposite orientations under the transcriptional control of of the CMV promoter. pCIN contains the binding site for the PNA CCCCCCCTTTTTTTTT-NH$_2$ (SEQ ID NO:18) on the template strand, while pCINr contains the same target site on the non-transcribed strand. The PNA was tested for the ability to effect In vitro transcription as per Example 29. The results are shown in FIG. 33. Both plasmids show non-specific inhibition of in vitro transcription at the highest concentration of PNA tested (1 mM). However, when the PNA concentration is decreased to 100 uM, approximately one half of the RNA produced corresponds to the size expected for the PNA truncated product (209 nucleotides) with the pCIN template. In contrast, pCINr shows only a faint truncated product of the correct size at the same concentration.

EXAMPLE 31
Effect of Ionic Strength and pH on PNA Mediated Termination of Transcription.

Figure 34:
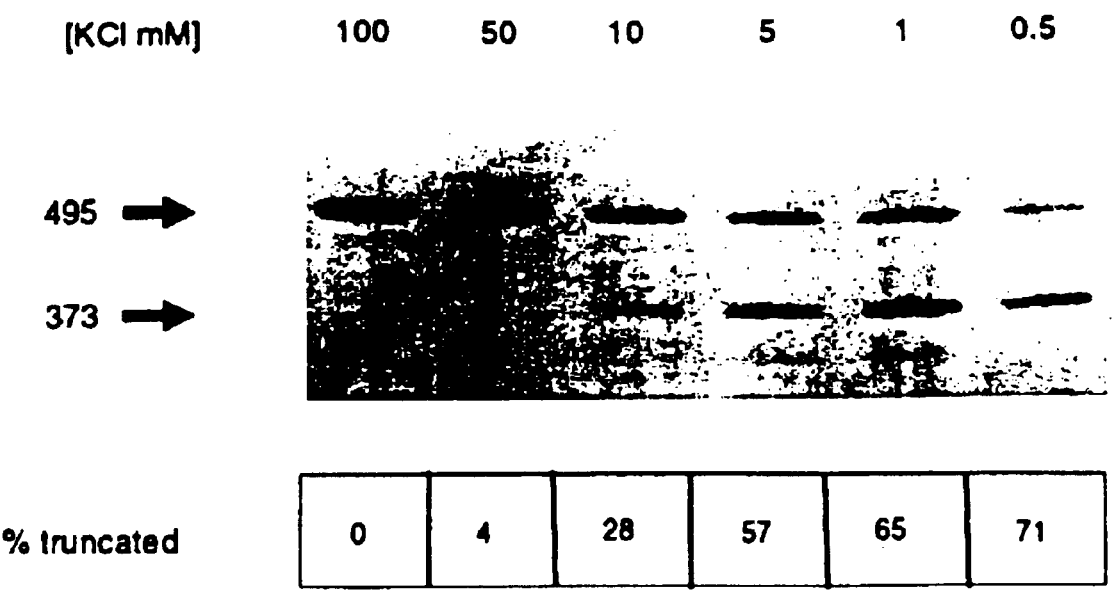
FIG. 34 shows a PAGE autoradiography illustrating the effect of salt concentration on PNA activity.

25 uM PNA TTTTCTTTT-NH$_2$ (SEQ ID NO:16) was pre-incubated three hours with pCH495 at pH 6.8 in 0.5 to 100 mM KCl buffer. Following the pre-incubation the linearized plasmid was transcribed as detailed in Example 29. The results are shown in FIG. 34 with the percent PNA truncated product indicated at the bottom of each lane. The proportion of the truncated product relative to full length transcript is increased as the salt concentration is decreased.

Figure 35:
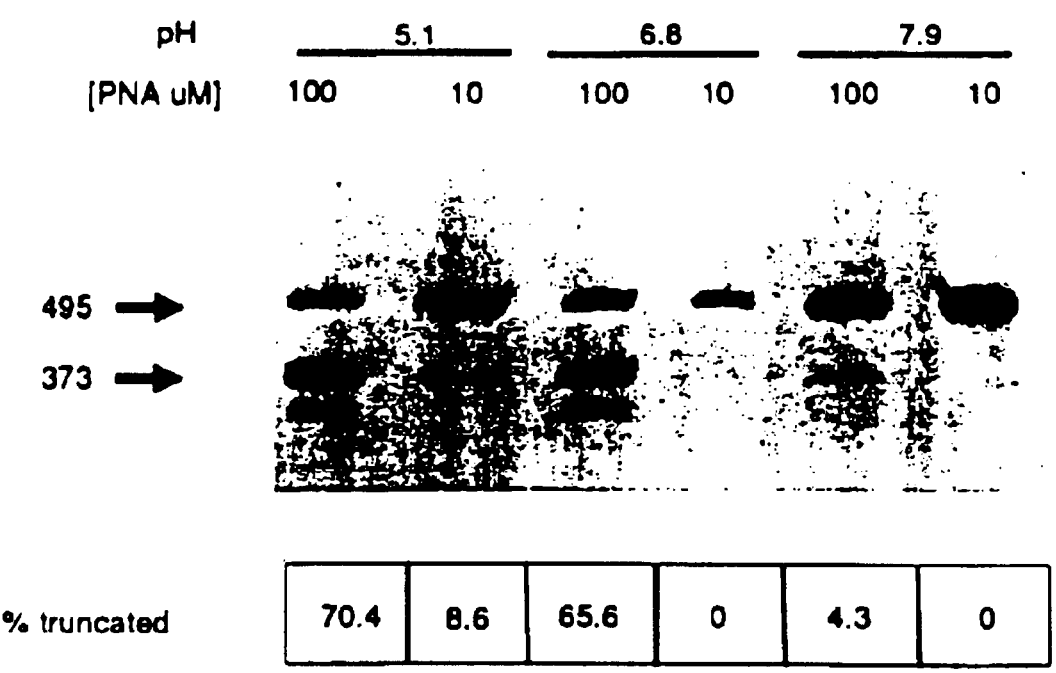
FIG. 35 shows a PAGE autoradiography illustrating the effect of pH on PNA activity.

The same PNA and plasmid template were used to determine the effects of pH on the ability of PNA to effect transcription. PNA at a concentration of 10 or 100 uM, was pre-incubated (as described in Example 29) with the template in 10 mM KCl buffer at pH 5.1, 6.8, or 7.9 then transcribed in HeLa cell extracts. The resultant transcription products are shown in FIG. 35 with the percent truncated product shown below each lane. At the highest pH tested, 7.9, little specifically truncated product is observed even at a PNA concentration of 100 uM. A slight decrease in pH to 6.8 results in a dramatic increase in the amount of truncated message produced at the 100 uM PNA concentration, although no truncated message is observed at a PNA concentration of 10 uM. However, when the pH is decreased to 5.1, a small amount of the truncated product is observed even at the lower PNA concentration and is increased at the higher PNA concentration.

The experiments were also performed with the other PNA's. The IVT$_{50}$ for each is listed in Table I, above. The effect of pH on PNA binding seems to become more enhanced as the percentage of cytosine residues in the PNA oligomer increases, probably due to enhanced binding upon cytosine protonation. At pH 5.1, one PNA, CCTCCTTCCC-NH$_2$ (SEQ ID NO:19), showed only a small amount of truncated product at the highest concentration tested. At higher pH no truncated product was observed at all. Higher PRA concentrations were not tested since they resulted in complete non-specific inhibition of transcription. This non-specific effect was generally more pronounced in the oligomers with larger cytosine/thymidine ratios.

The ability of PNA to inhibit transcription in vitro supports it use as an antigens therapeutic agent. In using PNA as an antigens agent both pH and ionic barriers would be considered. The effects of pH are mitigated by targeting adenosine rich regions, avoiding dG/dC duplexes. Alternatively, modified residues, such as methyl cytosine could facilitate binding. In this example inhibition of in vitro transcription was most efficient at ionic strengths less than those typically found in cells. Therefore, it is possible that PNA will strand invade under physiological conditions if given sufficient time to overcome kinetic barriers. Further to enhance the rate of strand invasion metabolically active regions of the genome would be targeted.

EXAMPLE 32
In Vitro Binding of PNA to Target.

The target for in vitro binding of duplex DNA was prepared by annealing two 50 base DNA oligonucleotides in which the binding site for PNA TITTCTTTT-NH$_2$ (SEQ ID NO: 16) is centered (5'-AAACAGGGCA GGAAACAGCA TATTTTCTT TAAAATTAGC AGGAAGATGG-3'(SEQ ID NO:46) and 5'-CCATCTTCC TGCTAATTTT AAAA-GAAAAT ATGCTGTTTC CTGCCCTGTTT-3' (SEQ ID NO:77)). The target was $^{32}$P end labeled, then incubated at roughly 500 nM with various concentrations of PNA in the buffers described above for 4 hours at room temperature. PNA bound duplex was seperated from free by electrophoresis on a 5% native acrylamide gel in TBE. The gel was then dried and exposed on a Molecular Dynamics Phospholmager. The K$_d$ is given as the PNA concentration at which one half of the labeled target is bound. Gel shifts of PNA against DNA oligonucleotide complement were carried out in the same buffers using an end labeled DNA oligonucleotide with the sequence 5-AAAAGAAAA-3'(SEQ ID NO:78), which was present in each hybridization mix at 1 nM. Bound DNA oligonucleotide was seperated from See by electrophoresis through a 12% native acrylamide gel in TBE.

Figure 36B:
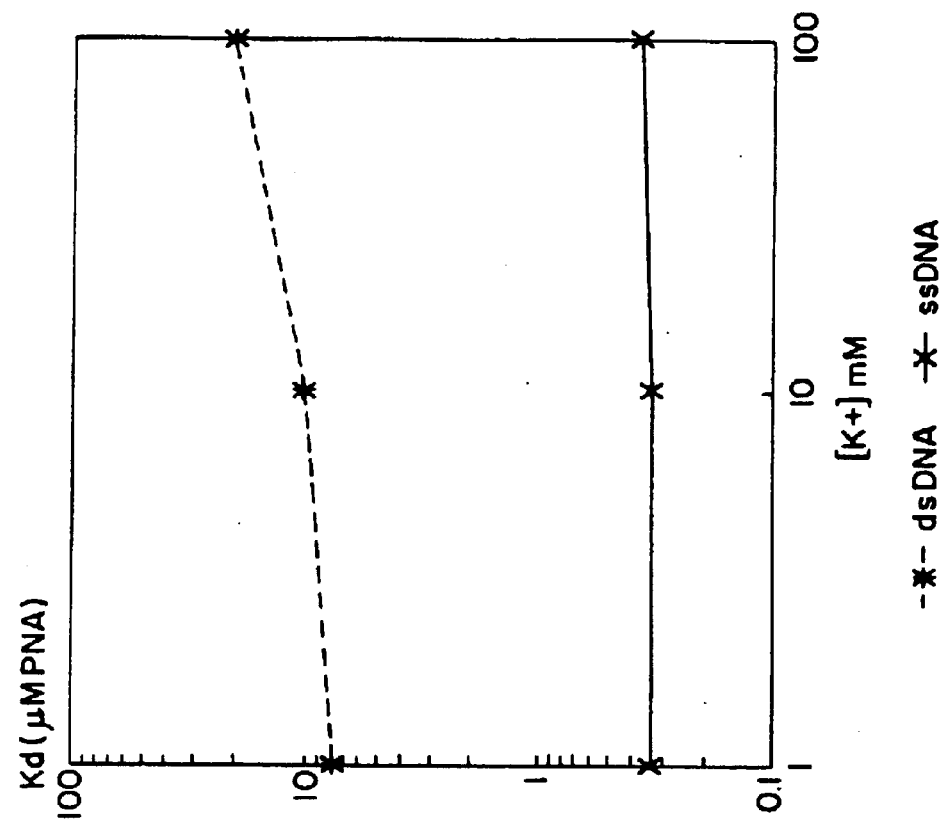
FIG. 36 are charts plotting $K_D$ vs ph and $K_D$ vs ionic strength on in vitro binding of PNA to complement.
Figure 36A:
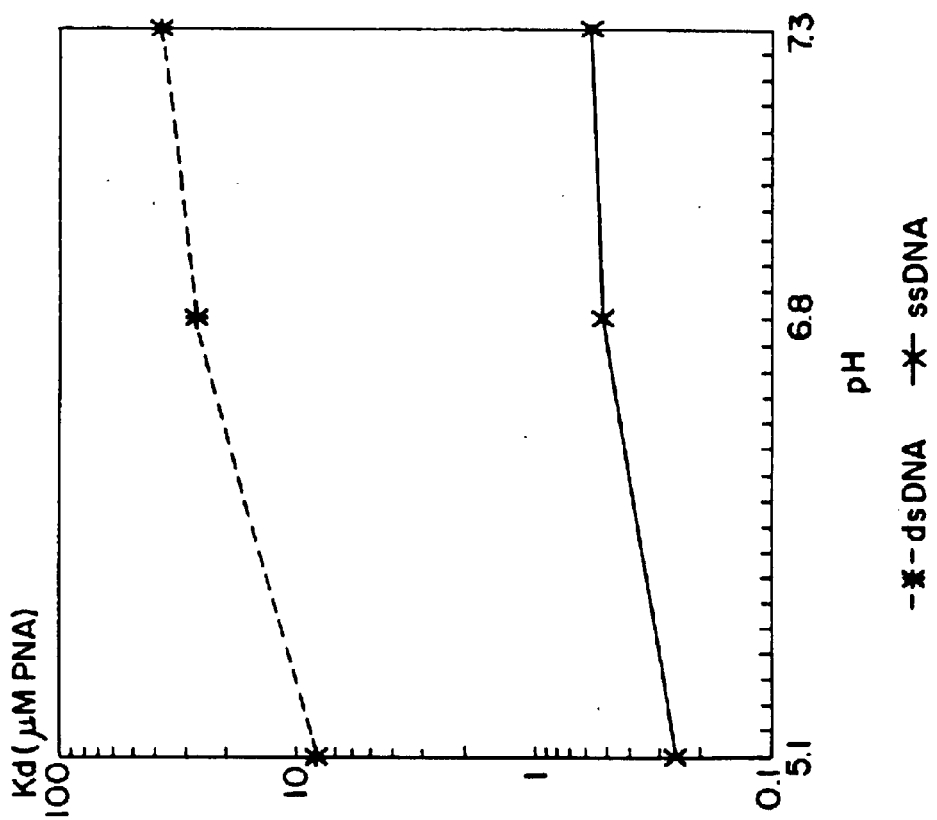

Following the above protocols, the in vitro binding of PNA to DNA was assessed by gel mobility shift assay. The 50 base pair duplex DNA target for the PNA TTTTCTTTT-NH$_2$ (SEQ ID NO:16) was prepared with the binding site for PNA TTTTCTTTT-NH$_2$ (SEQ ID NO:16) centered in the fragment. The DNA complement (5'-AAAAGAAAA-3') (SEQ ID NO:78) was synthesized and end labeled. PNA was incubated with the either the single strand complement or duplex DNA target in 20 mM KCl buffer at pH 5.1, 6.8, or 7.9. PNA bound DNA was then seperated from free on a native acrylamide gel. FIG. 36a shows that PNA binding to both the single stranded and duplex target is effected by the pH of the binding buffer. Binding affinity (K$_d$, the PNA concentration at which one half of the target is shifted in mobility) to both single stranded and duplex DNA complement was determined by the gel shift assay. As the pH is decreased affinity increases. PNA affinity for the single stranded target is much greater than for the duplex target, presumably due to the stability of the DNA duplex in 20 MhM KCl. Other experiments to determine the binding affinity of other PNA oligomers showed that the effect of pH on binding was more pronounced with cytosine rich PNA's (data not shown).

Binding of PNA to target was also utilized to study the effects of salt concentration on PNA binding by incubating PNA TTTTCTTTT-NH$_2$ (SEQ ID NO:16) with it's single stranded or duplex target in buffers containing 1, 10, or 100 mM KCl at pH 6.8. The results are shown in FIG. 36b. While the salt concentration does have a large effect on the ability of PNA to bind duplex DNA, there is little salt effect on the binding to single stranded complement. Similar results were obtained when PNA TTCCCTTCC-LysNH$_2$ (SEQ ID NO:12) was tested (data not shown).

EXAMPLE 33
PNA-DNA Base Pair Recognition

To test if PNA containing all four natural nucleobases is a true DNA mimic in terms of base pair specific hybridization to complementary oligonucleotides a pentadecamer PNA was designed to contain an almost equal number of pyrimidines and purines yet having no more than two purines or pyrimidines juxtaposed. It contains an equal number of thymines and cytosines and a single guanine. Furthermore, the sequence of the pentadecamer is non-selfcomplementary and contains a GTCA sequence at the center. By measuring the thermal stability of complexes between the PNA pentadecamer and the Watson-Crick complementary oligonucleotide, as well as 12 other oligonucleotides each having a single base mismatch at one of the four center PNA nucleobases, information about PNA-DNA base pair recognition was obtained. Finally, the PNA was designed with no pyrimidine stretches so as to strongly disfavor—if not prohibit—triplex formation.

The thermal stability measured as the melting temperature, $T_m$, of complexes between the pentadecamer, H-TGTACGTCACAACTA-NH$_2$ (SEQ ID NO:10) and the complementary deoxyoligonucleotide 3'-ACATGCAGTGTTGAT (SEQ ID NO:47) (termed anti-parallel orientation: amino terminal of the PNA complementary to the 3'-end of the oligonucleotide) was 69.5° C. (see Table II), whereas the $T_m$ of the corresponding PNA-DNA complex in parallel orientation was 56.1° C. The $T_m$ for the PNA-RNA complexes was 72.3 and 51.2° C., respectively (see Table II). The orientation preference was further settled by using two decamer PNAs, and hybridizing these to complementary oligonucleotides in both orientations. The anti-parallel orientation was preferred in all cases (see Table II). Furthermore, it is noteworthy that virtually identical $T_m$s were obtained regardless of which strand is the PNA and which is the DNA (see Table II, 2nd & 3rd row). The results also show that the presence of a terminal lysine amide (add to certain PNAs to reduce aggregation of oligo thymine PNA) does not influence the preferred orientation of the PNA relative to the DNA.

Figure 37:
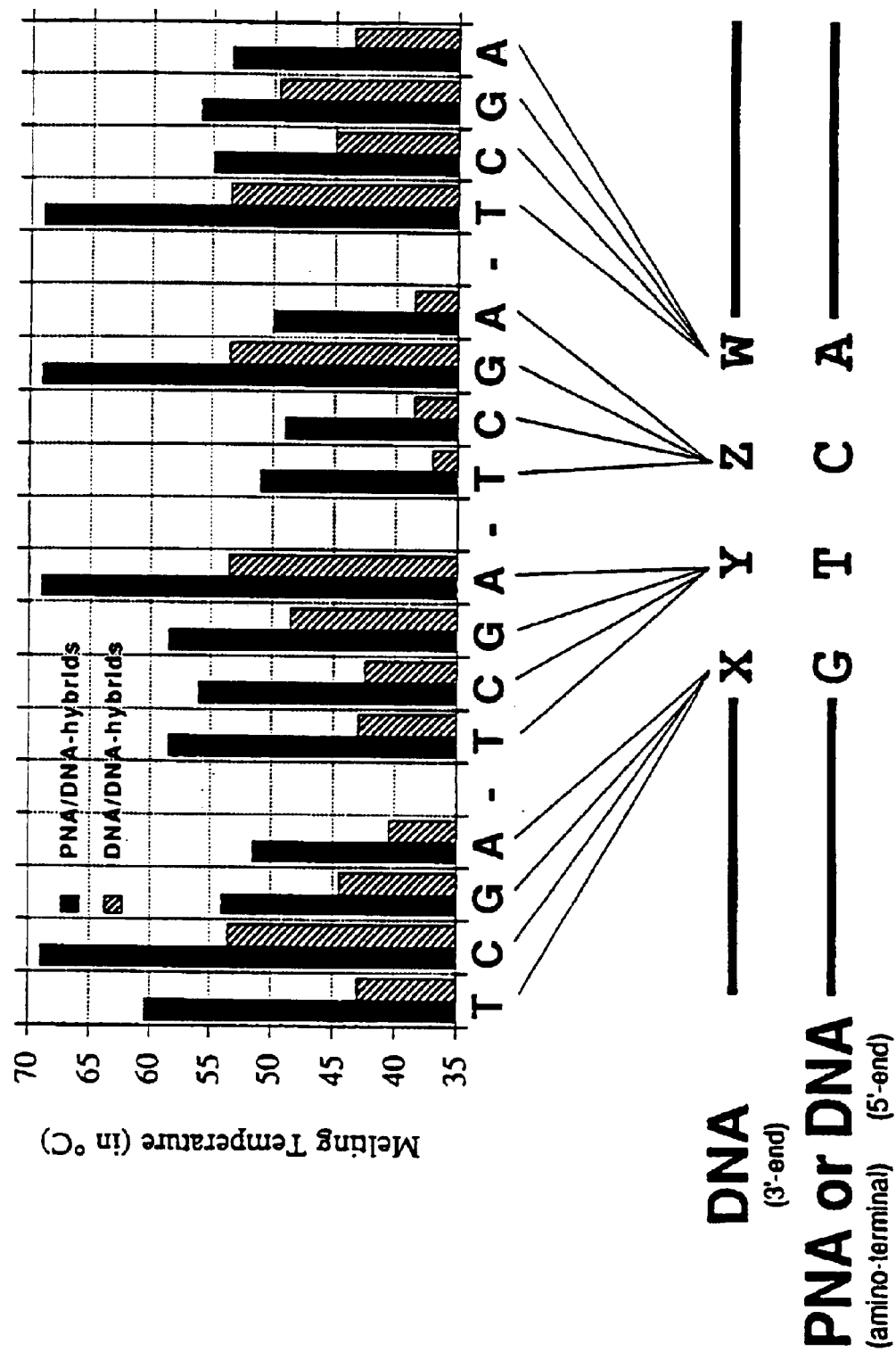
FIG. 37 is a chart illustrating melting temperature for hybrid duplex binding.

When a Watson-Crick base pair mismatch was introduced in the oligonucleotide at any position facing the four middle PNA nucleobases (GTCA) in the pentadecamer a large increase in $T_m$ (8–20° C., FIG. 37, was observed, thereby providing compelling evidence that PNA-DNA recognition takes place by Watson-Crick base pairing, i.e., A-T and G-C base pairing. Qualitatively similar results were obtained using oligonucleotides in the parallel orientation. Shown in FIG. 37 are the effect of base pair mismatches on the thermal stability of PNA/DNA complexes. Thermal stability of complexes between PNA, H-TGTACGTCACAACTA-NH$_2$ (SEQ ID NO:10) and the thirteen oligonucleotides 3'-d (ACATGXYZVGTTGAT), in which X,Y,Z,V=C,A,G,T for the case where the PNA and DNA sequences are complementary are shown. In each of the twelve other oligonucleotides, three of the bases (X,Y,Z,V) were complementary while the fourth was one of the three non-complementary nucleobases. For example, when (X=T,Y=G,Z=A) then V=A or C or G etc. Thus each of the twelve oligonucleotides contains one of the twelve possible base pair mismatches relative to the PNA pentadecamer. The $T_m$ of these complexes are displayed as solid bars in FIG. 37. For comparison, the results of similar experiments performed with DNA/DNA duplexes are displayed (hatched bars). Hybridizations were performed in 10 mM Na-phosphate, pH 7.0, 150 mM NaCl, 1 mM MgCl$_2$.

Figure 38:
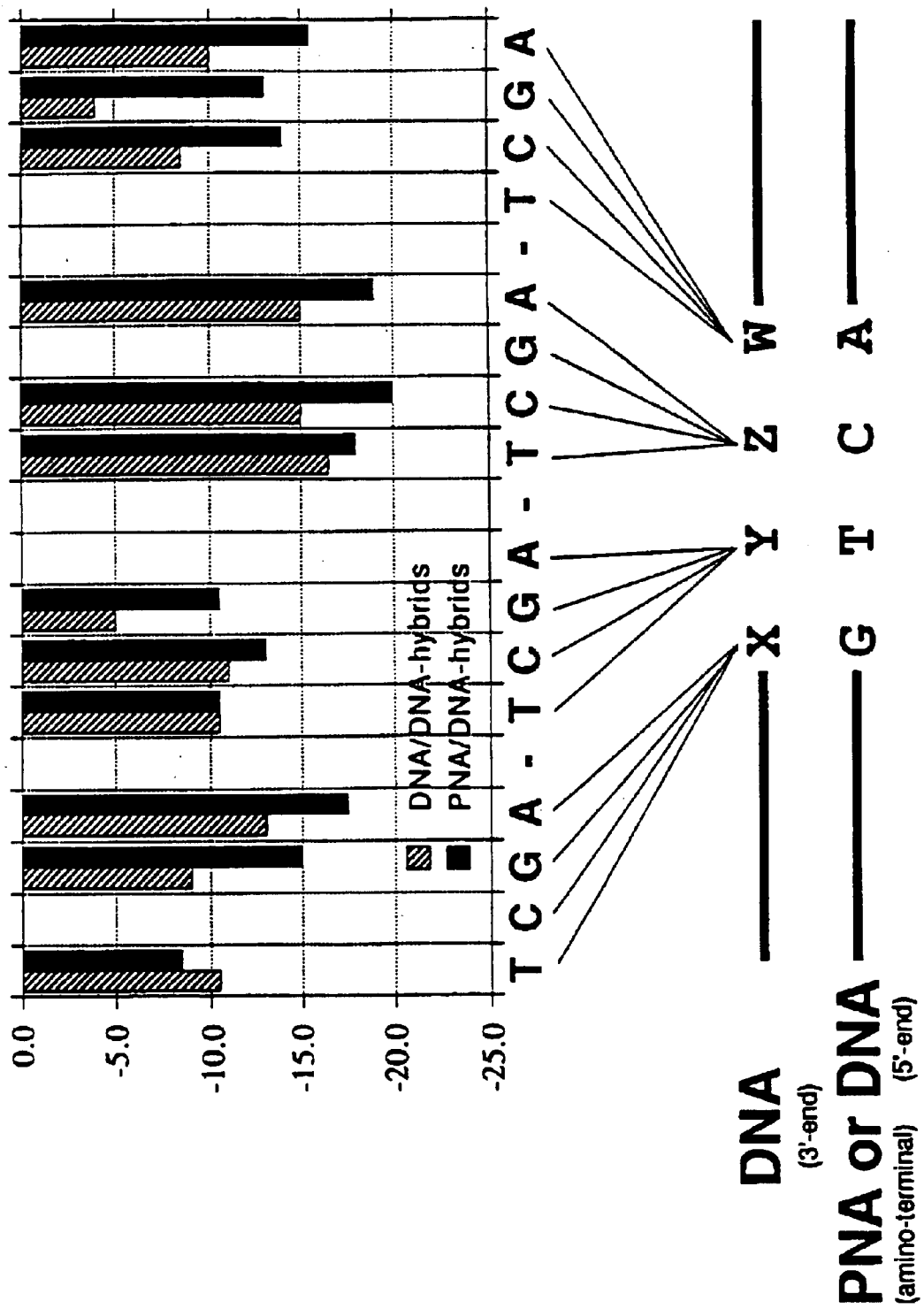
FIG. 38 is a chart illustrating melting temperature for hybrid duplex binding.

For comparison we also measured the thermal stabilities of the corresponding DNA/DNA duplexes as shown in FIG. 38. $\Delta T_m$ values for mismatches are shown in FIG. 38. Hybridizations were as for FIG. 37.

It is noteworthy that for virtually all base pair mismatched, the decrease in stability is greater for the PNA/DNA complex than for the DNA/DNA complex (see FIG. 38), thereby indicating that the sequence discrimination is, if anything, more efficient for PNA recognizing DNA than for DNA recognizing DNA.

Figure 39:
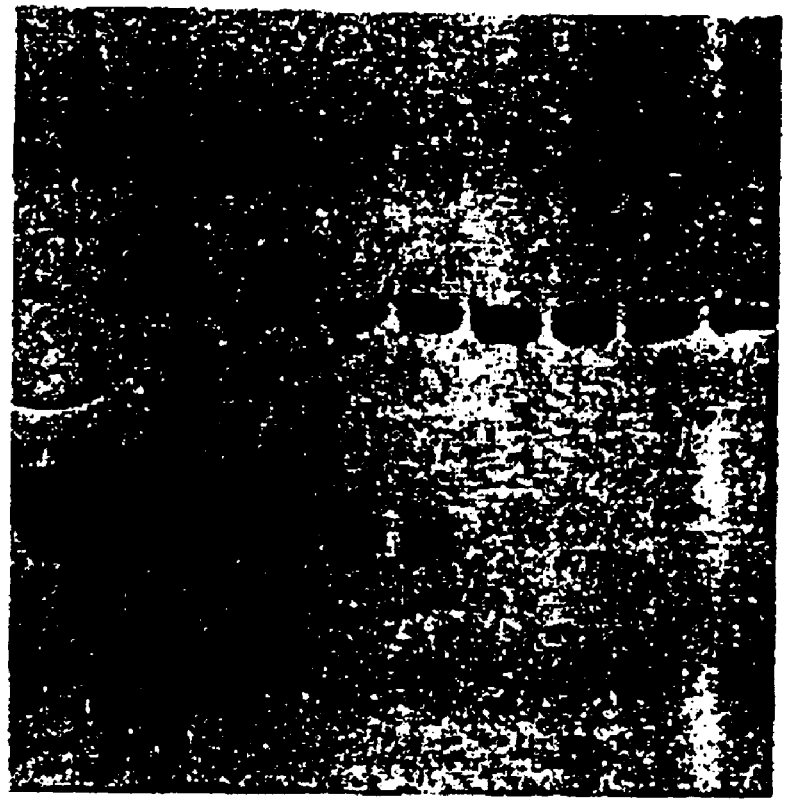
FIG. 39 shows a PAGE autoradiography illustrating titration by gel-shift binding of PNA to a end labeled oligonucleotide.

The unambiguous evidence for Watson-Crick base pairing suggest that these PNA/DNA complex 5 are duplex s rather than the (PNA)$_2$/DNA triplexes previously observed with homo-pyrimidine PNA. This conclusion was confirmed by titration experiments using $^{32}$P-labeled oligonucleotides in a gel retardation assay. Complete complex formation was observed at a 1:1 stoichiometry of [PRA] to [DNA] as shown in FIG. 39. Similar results were obtained using circular dichroism for the detection of complex formation (data not shown). In this example titration was by gel-shift

TABLE II

Melting temperatures $T_m$ (° C.) for PNA/DNA, PNA/RNA, DNA/DNA and DNA/RNA complexes.[a]

| 1st strand sequence[b] | TGTACGTCACAACTA[c] (SEQ ID NO:10) | GTAGATCACT[d] (SEQ ID NO:79) | AGTCATCTAC[d] (SEQ ID NO:80) |
|---|---|---|---|
| DNA:DNA | 53.3 | 33.5 | 33.5 |
| DNA:RNA | 50.6 | nd | nd |
| PNA:DNA (parallel) | 56.1 | 38.0 | 38.0 |
| PNA:DNA (anti-parallel) | 69.5 | 51.0 | 49.0 |
| PNA:RNA (parallel) | 51.2 | nd | nd |
| PNA:RNA (anti-parallel) | 72.3 | nd | nd |

[a]Absorbance vs. temperature curves were measured at 260 nm in 100 mM NaCl, 10 mM Na-phosphate, 0.1 mM EDTA, pH 7. $T_M$, the temperature at which half of the molecules are hybridized was obtained by fitting triplicate melting curved at 4 μM of each strand to a modified two state model with linear sloping baseline.
[b]Written 5'-3' for oligonucleotides and N- to C- terminal for PNA.
[c]The PNA terminates in a carboxamide.
[d]The PNA terminates in a lysine amide.

of the binding of PNA H-TGTACGTCACAACTA-NH$_2$ (SEQ ID NO:10) to the 5'-endlabeled oligonucleotide 3'-d (ACATGCAGTGTTGAT) (SEQ ID NO:47). The oligonucleotide was labeled with $^{32}$P at the 5'-end using standard techniques[32]. The oligonucleotide (1 nmole, 10$^3$ cpm) was incubated with various amounts of PNA (0–5 nmole) in 10μ 10 mM Tris-HCl, 1 mM EDTA, pH 7.4 for 1 hour at 37° C. The samples were analyzed by electrophoresis in 20% polyacrylamide gels (TBE buffer=89 mM Tris-borate, pH 8.3, 1 mM EDTA) and the radiolabeled DNA visualized by autoradiography. Concentrations of oligonucleotides and PNA were measured photometrically. Similar results were obtained using the complementary oligonucledtide of reversed polarity (5'-d(ACATGCAGTGTTGAT) (SEQ ID NO:52).

EXAMPLE 34

Structure of the PNA/DNA Duplex

The $T_m$ data (Table II above) show that PNA, in contrast to DNA or RNA, may bind to complementary DNA or RNA in either orientation, although the antiparallel orientation is preferred. Since the PNA backbone is achiral, the orientation does not by itself impose any steric constraints on the winding of the helix, i.e., left or right handed helicity, and computer modelling also indicates that both binding orientations are possible.

Figure 40:
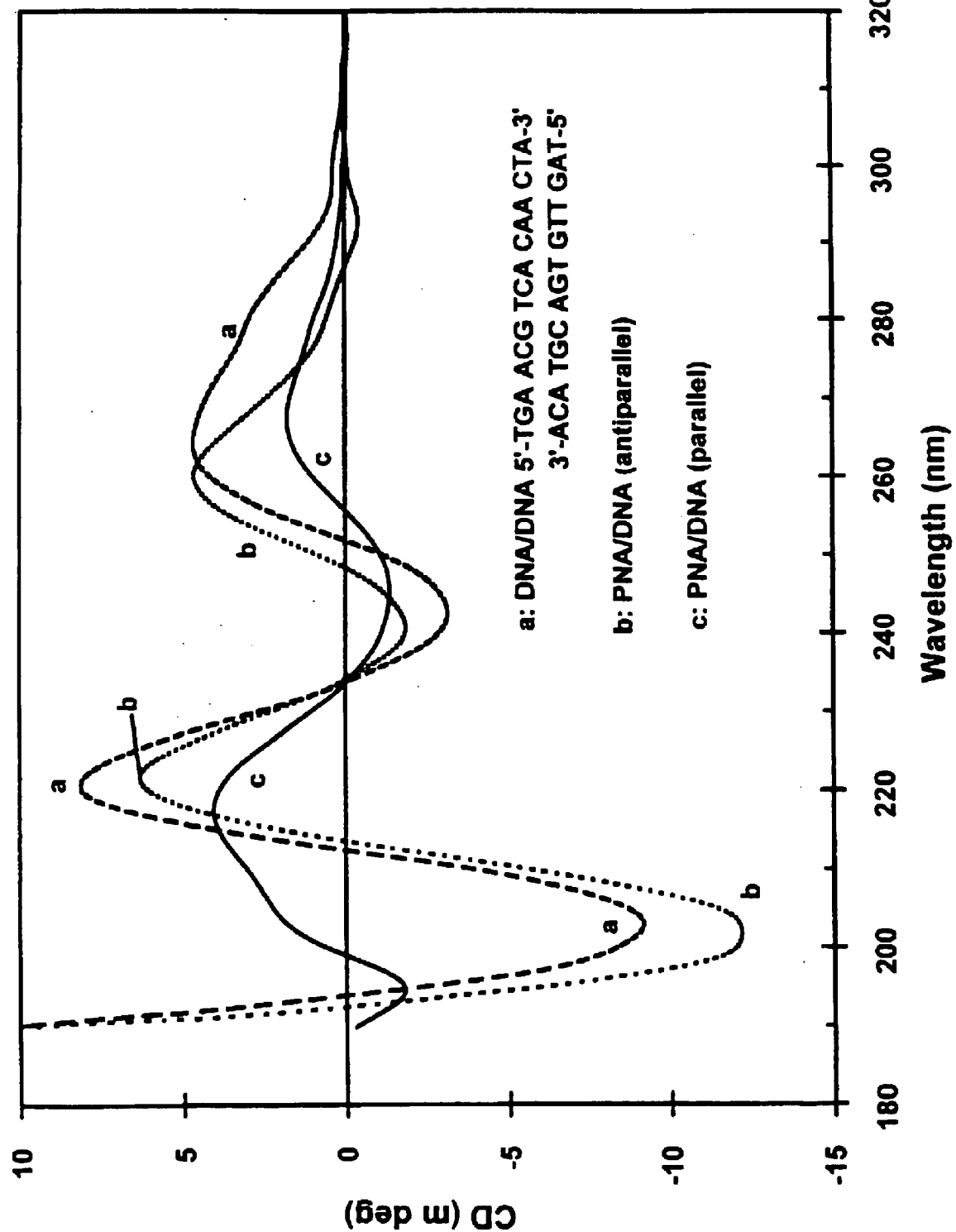
FIG. 40 is a circular dichroism spectra.
Figure 41:
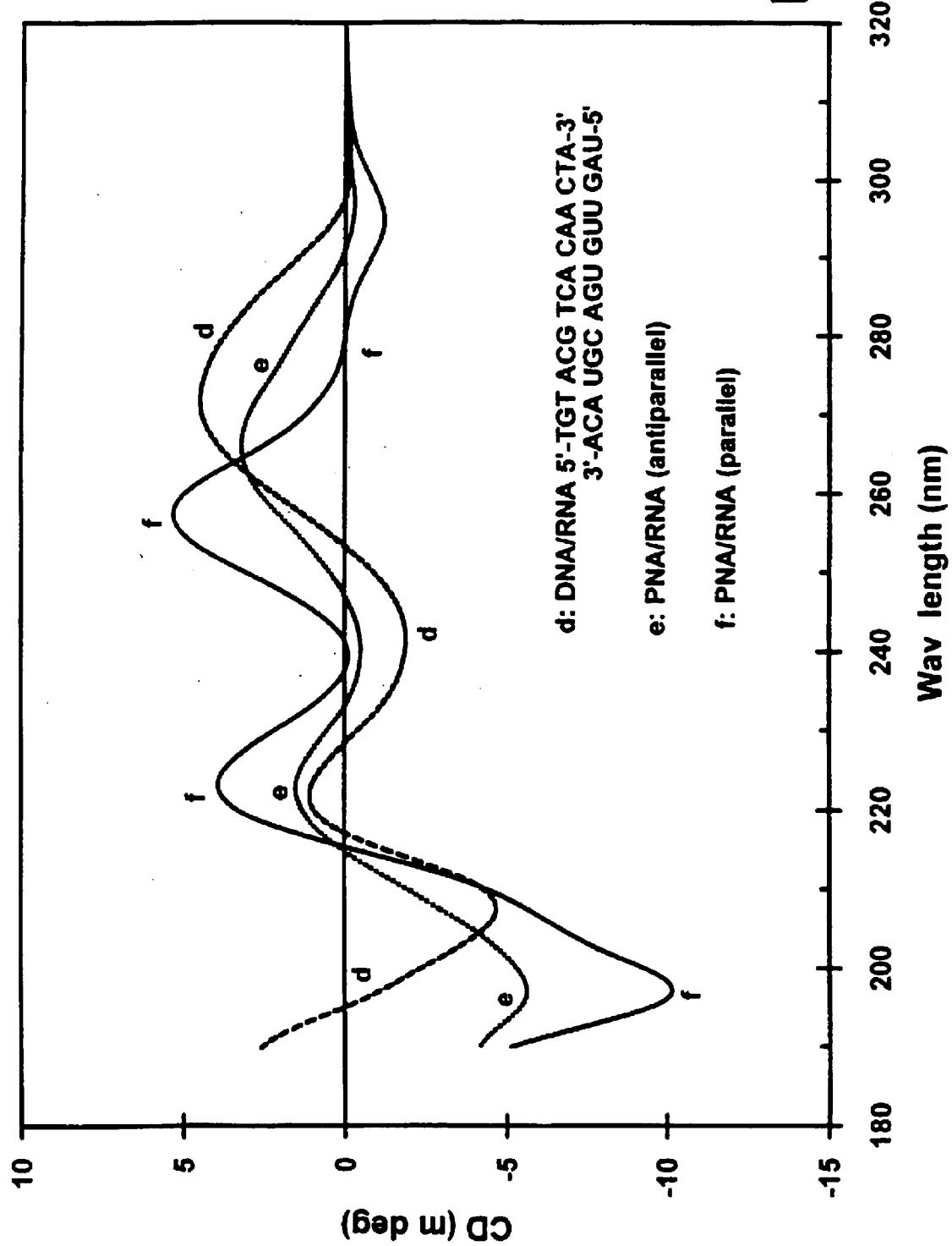
FIG. 41 is a further circular dichroism spectra wherein d: DNA/RNA 5'-TGT ACG TCA CAA CTA-3' (SEQ. ID. NO:75) and 3'-ACA UGC AGU GUU GAU-5' (SEQ. ID. NO: 89)
Figure 42:
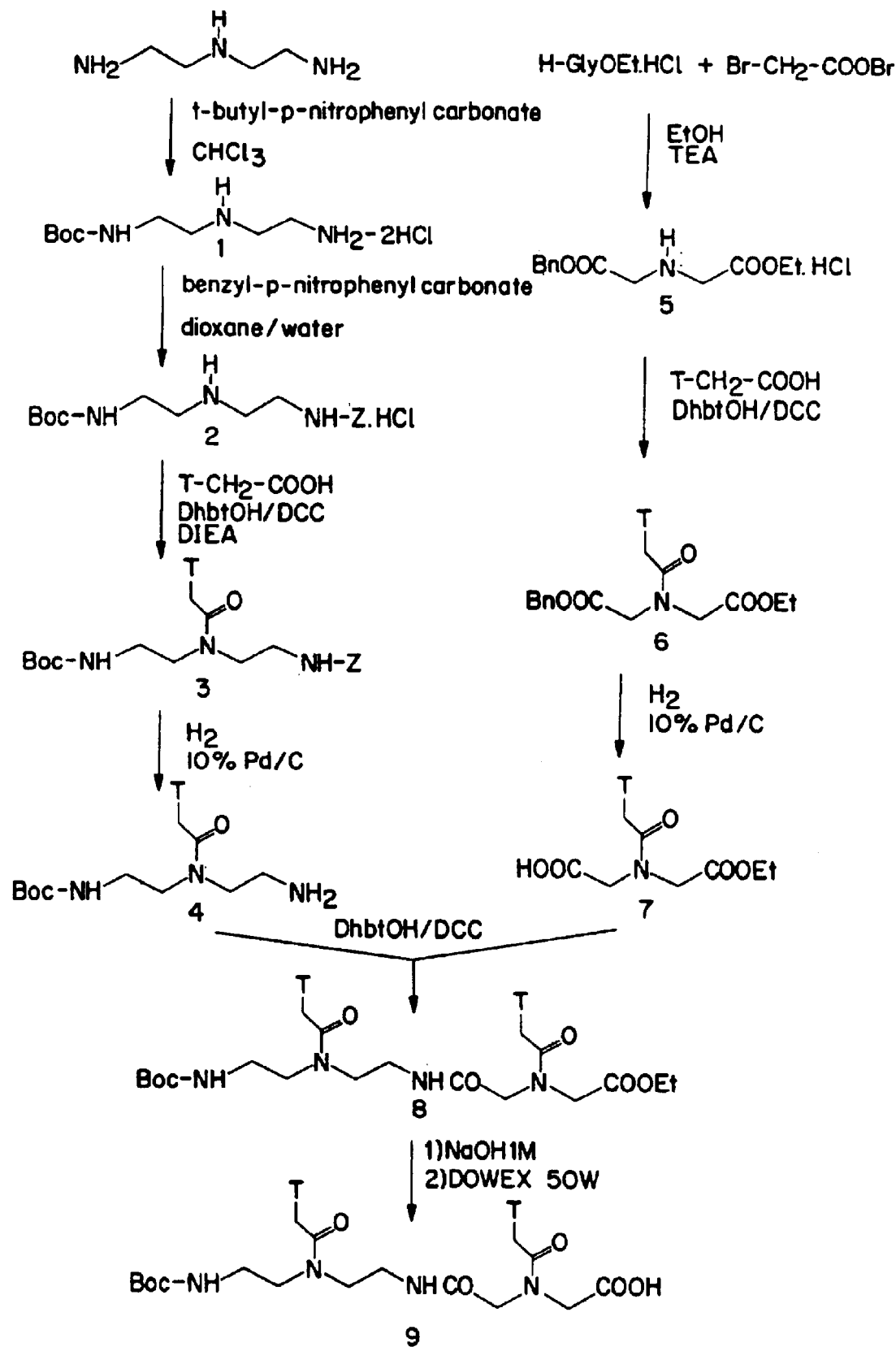
FIG. 42 is a chemical schematic.
Figure 43:
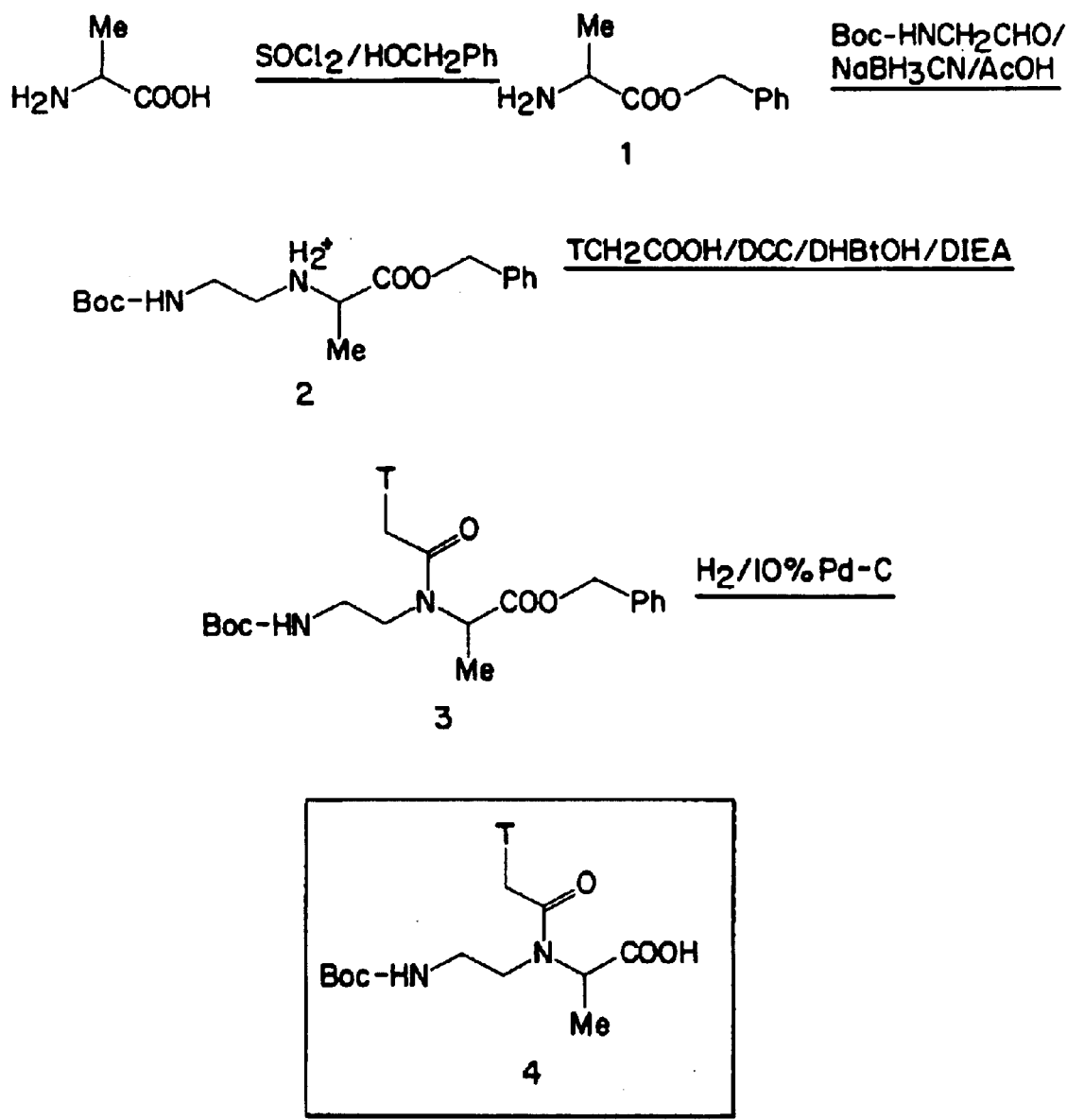
FIG. 43 is a further chemical schematic.

Information on secondary structure may be obtained from circular dichroism (CD) measurements since these are sensitive to the base pair geometry in the helix. FIG. 40 shows the CD spectra of the PNA/DNA, PNA/RNA, DNA/DNA and DNA/RNA duplexes. Shown in FIG. 40 is the circular dichroism spectra of PNA/DNA (a: antiparallel; b: parallel), PNA/RNA (c: antiparallel; d: parallel), DNA/DNA ( ) and DNA/RNA (f) complexes. The complexes were formed by mixing equal molar amounts of the two complements in distilled H$_2$O. Circular dichroism spectra were recorded on a Jasco 700 instrument at room temperature using an optical path of 1 mm. All measurements were averaged ten times and smoothed. All spectra are largely similar suggesting that PNA/DNA and PNA/RNA duplexes are right handed helices with a base pair geometry not drastically different from that found in a B- or an A-DNA helix. However, it is interesting that the CD-spectra, and thus the structure, of PNA/DNA (or PNA/RNA) duplexes are distinctly different when parallel and anti-parallel complexes are compared. The reference DNA/DNA duplex would be expected to adopt a B-like helix while the RNA/DNA duplex would be expected to adopt a more A-like helix, but the CD-spectra of neither of these short duplexes show typical B- or A-like features. Thus it is not possible to conclude from these results if the PNA/DNA or PNA/RNA helices are preferentially A- or B-like.

EXAMPLE 35

Thermodynamics of the PNA/DNA Duplex Formation

Thermodynamics parameters for hybridization can be extracted from thermal stability measurements when these are performed at varying concentrations of the complexes, or from the shape of the thermal denaturation curves. Both methods were used to determine ΔH°, ΔS° and ΔG° for formation of the PNA/RNA, DNA/RNA, PNA/DNA and DNA/DNA duplexes (Table III). It is remarkable that the decrease in entropy is almost identical for the formation of DNA/DNA and PNA/DNA duplexes and that both reactions are strongly enthalpy driven.

TABLE III

Thermodynamic parameters for the formation of PNA/DNA, PNA/RNA, DNA/RNA and DNA/DNA duplexes with the sequence TGTACGTCACAACTA present in the PNA strand strand[a].

|  | DNA:RNA | PNA:RNA | DNA:DNA | PNA:DNA |
|---|---|---|---|---|
| ΔH° (kcal/mol)[b] | −94.0 | −109.7 | −91.5 | −103.5 |
| ΔS° (eu)[b] | −264.9 | −291.4 | −253.9 | −276.4 |
| ΔG°$_3$[b] | −11.8 | −19.3 | −12.7 | −17.7 |
| T$_M$ (° C., 8 μM)[b] | 49.8 | 72.3 | 53.6 | 68.9 |
| ΔH° (kcal/mol)[c] | −128.9 | −128.5 | −105.3 | −106.6 |
| ΔS° (eu)[c] | −372.8 | −345.9 | −296.2 | −285.8 |
| ΔG°$_{37}$ (kcal/mol)[c] | −13.3 | −21.2 | −13.4 | −18.0 |
| T$_M$ (° C., 8 μM)[c] | 50.1 | 72.2 | 53.5 | 68.8 |
| ΔH° (kcal/mol)[d] | −111.5 | −119.1 | −98.4 | −105.0 |
| ΔS° (eu)[d] | −318.9 | −318.7 | −275.1 | −281.1 |
| ΔG°$_{37}$ (kcal/mol)[d] | −12.6 | −20.2 | −13.1 | −17.9 |
| T$_M$ (° C., 8 μM)[d] | 50.0 | 72.2 | 53.5 | 68.8 |

[a]Measured in 100 mM NaCl, 10 mM Na-phosphate, 0.1. mM EDTA, pH 7.0.
[b]Obtained by fitting melting curves to a modified two state model with linear sloping baselines.
[c]Obtained from linear plots of 1/T$_M$ versus log (concentration).
[d]Temperature independent parameters calculated as the average of the two methods described above.

The finding that ΔH° and ΔS° are similar for the formation of PNA/DNA and DNA/DNA duplexes, combined with the finding that the PNA/DNA and RNA/DNA duplex structures have similar stacking according to the CD results, indicates that single stranded PNA must have much the same degree of bas stacking as single stranded DNA, and thus appears to be highly structured. The kinetics of PNA/RNA duplex formation was also measured, and the results show that the rate of hybridization is at least as fast as that for 2'O-Me-RNA/RNA or DNA/DNA duplex formation (Table IV). Again fully consistent with the suggestion that the single stranded PNA is at least as prestructured for duplex formation as is DNA (or RNA).

TABLE IV

Equilibrium and rate constants for duplexes.

| Duplex | [Na+] | (M)T(° C.) | K$_D$[a] | k$_1$ (M$^{-1}$s$^{-1}$)[a,b] |
|---|---|---|---|---|
| PNA/RNA[c] | 0.1 | 37 | 5 × 10$^{-11}$ | 2 × 10$^6$ |
| 2'-O-Me/RNA[c] | 0.1 | 37 | 5 × 10$^{-11}$ | 2 × 10$^5$ |
| DNA/RNA[c] | 0.1 | 37 | 2 × 10$^{-9}$ | — |
| DNA/DNA[d] | 0.2 | 39 | — | 3 × 10$^5$ |

[a]The buffer was 100 mM NaCl, 10 mM phosphate, 1 mM EDTA, pH 7.0, and the dissociation constant was determined from gel-shift experiments using a $^{32}$P-labeled RNA. The rate was measured in experiments which were stopped by adding 50-fold excess of unlabeled RNA followed by rapid freezing.
[b]The rate constants were determined from plots of the pseudo-first order rate constant versus the reagent concentration, which in all cases were much higher than the concentration of the labeled RNA target.
[c]The sequence of the reagent was: N-(or 5')-TGTACGTCACAACTA-C-terminal(or 3')(SEQ ID NO:81), and the sequence of the RNA target: 5'-TAGTTGTGACGTACA-3(SEQ ID NO:82). 2'-O-Me is the 2'-O-methyl RNA derivative.
[d]Results taken from Tibanyenda et. al., Eur. J. Biochem. 1984, 139, 19. The sequence was: 5'-CAACTTGATATTAATA(SEQ ID NO:83).

The following chemical synthesis are shown in Schemes I and II.

Scheme I

EXAMPLE 36
MonoBoc-diethylenetriamine Dihydrochloride (1)

A solution of t-butyl-p-nitrophenyl carbonate (10 g; 0.0418 mole) in $CHCl_2$ (400 ml) was added to a solution of diethylenetriamin (45 ml; 0.0417 mol ) in $CHCl_3$ (250 ml)at 0° C. over a period of 3 h. The reaction mixture was stirred overnight at room temperature. The precipitate that appeared was filtered and washed in $CHCl_3$. The solvent was evaporated, first under reduced pressure with a water-aspirator, then with an oil-pump (0.05 mmHg; 50° C.). The residue was dissolved in a mixture ethylacetate (50 ml)/$H_2O$ (50 ml) and the solution was acidified to pH 4 with HCl 4N, extracted with ethylacetate (3×50 ml). The aqueous solution was adjusted to pH 9 with NaOH 2N and extracted with ethylacetate (3×50 ml). The aqueous phase was adjusted to pH 11.5 and extracted with ethylacetate (10×50 ml). The combined organic phases of the last extraction were evaporated under reduced pressure and the resulting oil was dissolved in water (50 ml) and acidified to pH 5. Evaporation of water yielded a slightly yellow solid, which was thoroughly washed with ether (yield: 6.41 g; 55%). $^1$H-NMR ($D_2O$): δ (ppm): 1.4 (s, 9H); 3.0 (t, 2H); 3.3 (s broad, 4H); 3.4 (t, 2H)

EXAMPLE 37
Boc-, Z-diethylenetriamine Hydrochloride (2)

To a solution of 1 (5.5 g; 19.9 mmoles) in dioxane (50 ml)/water (50 ml) adjusted at pH 11 was added a solution of benzylnitrophenyl carbonate (5.44 g; 19.9 moles) in dioxan (50 ml) at a 0° C. over a period of 1 h, while maintaining the pH at 11 with NaOH 2N The reaction mixture was then stirred at room temperature for 1.5 h. Subsequently, ethylacetate (100 ml) was added and the reaction mixture was cooled at 0° C. and acidified to pH 4 with HCl 4N. A precipitate appeared in the organic phase. The two phases were separated and the organic phase filtered. This (addition of ethylacetate, separating the two. phases and filtering the organic phase) was repeated 3 times to give 3.05 g of white solid. An additional 1.38 g was obtained by joining all the organic phases and adding ether (Yield: 4.427 g; 59%). $^1$H-NMR (DMSO d6): δ (ppm): 1.5 (s, 9H); 3.0 (m, 4H); 3.4 (m, 4H); 5.1 (s, 2H); 7.4 (s, 5H); 7.1 (m, 1H); 7.6 (m, 1H). MS FAB+: M+1: 338.2

EXAMPLE 38
Coupling of 2 with N-1-carboxymethylthymine

Compound 2 (4 g; 10.7 mmoles), N-1-carboxymethylthymine (1.97 g; 10.7 mmoles), DhbtOH (1.75 g; 10.7 mmoles) and DIEA (1.2 ml; 12 mmoles) were dissolved in a mixture of $CH_2Cl_2$ (50 ml)/DMF (50 ml). After cooling at 0° C., DCC (2.2 g; 10.7 mmoles) was added and the reaction mixture was stirred at 0° C. for ½ h and 2.5 h at room temperature. DCU was filtered and washed with $CH_2Cl_2$ (2×100 ml). The combined organic phases were washed with $NaHCO_3$ 1M (3×100 ml), $KHSO_4$, 1M (3×100 ml), $H_2O$ (2×100 ml), dried over $Na_2SO_4$, filtered and evaporated under reduced pressure. The resulting oil was crystallized in chloroform/ether to yield 4.04 g (75 %) of product. $^1$H-NMR ($CDCl_3$); δ (ppm); 1.4 (s, 9H); 1.9 (s, 3H); 3.4 (m, 8H); 4.4 (d, 2H); 5.1 (d, 2H); 5.5 (m, 1H); 5.9 (m, 1H); 6.9 (s, 1H); 7.4 (s, 5H); 9.0 (s, 1H). MSFAB+: M+1; 504.

EXAMPLE 39
Hydrogenolysis of 3 to 4

Compound 3 (4 g; 7.9 mmoles) was dissolved in MeOH (150 ml). At 0° C., 10% Pd/C (1.4 g) was added. The reaction mixture was hydrogenated at 0° C. for 1 h, filtered through Celite and the solvent removed under reduced pressure to give 3.0 g (100%) of 4. $^1$H-NMR ($CDCl_3$); δ (ppm); 1.4 (s, 9H); 1.9 (s, 3H); 3.0–3.8 (m); 4.6 (d, 2H); 6,9 (s, 1H); 7.3 (s, 5H); 9.0 (s, 1H). MSFAB+:M+1: 370.2

EXAMPLE 40
N-(borsyl acetato)-glycine Ethyl Ester Hydrochloride (5)

At room temperature, benzyl bromo acetate (5.7 ml; 36 mmoles) was added over a period of 10 min. to a solution of glycine ethyl ester hydrochloride (5 g; 36 mmoles) and triethylamine (10.43 ml; 0.072 moles) dissolved in absolute EtOH (100 ml). After 4 days at room temperature, the solvent was removed under reduced pressure. The residue was dissolved in ethylacetate (50 ml)/$H_2O$ (25 ml). After separation of the two phases, the organic phase was thoroughly washed with water (8×25 ml). After evaporation of the solvent, the resulting oil was dissolved in ether (20 ml)/water (30 ml) and acidified to pH 4.5. After separation of the two phases, the aqueous phase was concentrated and the resulting oil crystallized in cold ether to yield 4 g (39%) of the product. $^1$H-NMR ($CDCl_3$); δ (ppm); 1.3 (t, 3H); 4.1 (d, 4H); 4.4 (q, 2H); 5.3 (d, 2H); 5.5 (m, 1H); 7.4 (s, 5H). MS FAB+; M+1: 252.1

EXAMPLE 41
Coupling of 5 with N-1-carboxymethylthymine to give 6

Compound 5 (2.8 g; 9.7 mmoles), N-1-carboxymethylthymine (1.79 g; 9.7 moles), DhbtOH (1.6 g; 9.7 mmoles) and DIEA (1.7 ml; 10 mmoles) were dissolved in a mixture of $CH_2Cl_2$ (30 ml)/DMF (30 ml). After cooling at 0° C., DCC (2.0 g; 9.7 mmoles) was added and the reaction mixture was stirred at 0° C. for ½ h and 4 h at room temperature. The DCU was filtered and washed with $CH_2Cl_2$ (120 ml). The combined organic phases were washed with $NaHCO_3$ 1M (3×60 ml), $KHSO_4$ 1M (3×60 ml), $H_2O$ (2×60 ml), dried over $Na_2SO_4$, filtered and evaporated under reduced pressure. The resulting oil was crystallized in chloroform (60 ml)/petroleum ether (120 ml) to yield 3.235 g (80%) of 6. $^1$H-NMR (DMSO d6): δ (ppm): 1.3 (dt, 3H); 1.9 (t, 3H); 4.2 (m, 4H): 4.4 (d, 2H); 5.3 (d, 2H); 7.2 (s, 1H); 7.4 (s, 5H); 11.3 (s, 1H). MS FAB+: M+1: 418.1

EXAMPLE 42
Hydrogenolysis of 6 to 7

Compound 6 (4 g; 9.6 mmoles) was dissolved in MeOH (100 ml)/DMF (25 ml). At 0° C., 10% Pd/C (1.6 g) was added. The reaction mixture was hydrogenated at 0° C. for 1H, filtered through Celite and the solvent removed under reduced pressure to give 3.12 g (99%) of 7. $^1$H-NMR (DMSO d6): δ (ppm); 1.3 (dt, 3H); 1.9 (s, 3H); 4.0–4.5 (m): 4.9 (s, 2H); 7.2 (s, 1H); 11.3 (s, 1H). MS FAB+: M+1: 328.1

EXAMPLE 43
Coupling of 4 and 7 to give 8

Compound 4 (2.8 g; 7.6 mmoles), 7 (2.5 g; 7.6 mmoles), DhbtOH (1.24 g; 7.6 mmoles) were dissolved in a mixture of $CH_2Cl_2$ (50 ml)/DMF (50 ml). After cooling at 0° C., DCC (1.56 g; 7.6 mmoles) was added and the reaction mixture was stirred at 0° C. for ½ h and overnight at room temperature. The DCU was filtered and washed with $CH_2Cl_2$ (250 ml). The combined organic phases were washed with $NaHCO_3$ 1M (3×100 ml), KHSO, 1M (3×100 ml), $H_2O$ (2×100 ml), dried over $Na_2SO_4$, filtered and evaporated under reduce pressure. The resulting oil was crystallized in chloroform (30 ml)/petroleum ether (60 ml). This material was recrystallized in chloroform (30 ml)/petroleum ether (25 ml) to give 0.608 g (12%) of 8. mS FAB+: M+1: 418.1

EXAMPLE 44
Hydrolysis of 8 to give 9

Compound 8 (25 mg, 0.037 mmoles) was dissolved in absolute ethanol (5 ml). Then NaOH 1M (1 ml) was added. The reaction mixture was stirred for 35 min. at room temperature and after cooling, neutralized with Dowex 50W (ca. 1 g). After filtration and evaporation of the solvent, the acid 9 was obtained as a white solid, yield 18 mg (82%). Scheme II

EXAMPLE 45
Alanine Benzyl Ester (10)

Thionylchloride (9.8 ml, 135 mmol, 1.2 eqv) was added dropwise during 15 min. to benzyl alcohol (210 ml) stirred under nitrogen and cooled to −10° C. Alanine (10.0 g, 112 mmol, 1.0 eqv) was added in portions during 10 min. The reaction mixture was heated overnight at 60–70° C. The reaction mixture was evaporated in vacuo and the residue was dissolved in water (150 ml). The pH was adjusted to 1–2 by addition of 4N HCl (aq.) and the aqueous phase was extracted with dichloromethane (2×200 ml). The organic phase was washed with hydrochloric acid (pH 1, 1×50 ml). The aqueous phases were collected, alkalinized (to pH 9–10) by addition of 2N NaOH (aq.) and subsequently extracted with dichloromethane (2×200 ml and 1×100 ml—alkaline extract). The alkaline extract was dried ($Na_2SO_4$), filtered and evaporated under reduced pressure affording 13.39 g (67%) of the title compound as a colorless oil. The product was characterized as its hydrochloride: The product (0.50 g, 2.8 mmol) was dissolved in ether (5 ml) and HCl in ether (2 ml) was added. The precipitate was collected by filtration and washed with ether (2×5 ml) yielding 0.57 g (95%) of white crystalline alanine benzyl ester hydrochloride. $^1$H-NMR ($D_2O$/TMS): δ 1.48 (unresolved d, 3H, Me); 4.15 (unresolved q, 1H, CH); 5.20 (s, 2H, $CH_2$); 7.38 (br s, 5H, Ph). $^{13}$C-NMR ($D_2O$/TMS): δ 14.7 (Me); 48.4 (CH); 68.1 ($CH_2$); 128.1, 128.5, 134.3 (Ph); 170.1 (C=O). MS(FAB+) m/z (%): 180 (100, M-HCl+H). Anal. Calcd. for $C_{10}H_{14}$, $ClNO_2$: C, 55.69; H, 6.54; N, 6.49. Found: C, 55.60; H, 6.56; N, 6.40.

EXAMPLE 46
N-(2-Boc-aminoethyl) Alanine Benzyl Ester Hydrochloride (11)

Alanine benzyl ester (10, 8.82 g, 49 mmol, 1 eq) was dissolved in MeOH (100 ml) and glacial acetic acid (10.34 g, 172 mmol, 3.5 eq) was added. The mixture was stirred at 0° C. under nitrogen and sodium cyanoborohydride (10.82 g, 172 mmol, 3.5 eq) was added. Boc-aminbacetaldehyde (15.67 g, 98 mmol, 2 eq) in NEOH (200 ml) was added dropwise during 2 h. The reaction mixture was stirred at 0° C. for 35 min. and then at 4–5° C. overnight. Water (300 ml) was added to the reaction mixture and the pH was adjusted to 9 by addition of solid sodium carbonate. The saturated solution was filtered and subsequently extracted with ether (3×500 ml). The organic phase was washed with a 1:1 mixture of saturated aqueous solutions of sodium chloride and sodium bicarbonate (1×450 ml), dried ($Na_2SO_4$), filtered and evaporated under reduced pressure to give 22.60 g of crude N-(2-Boc-amino-ethyl)alanine benzyl ester as a slightly golden oil. The crude product was dissolved in dry ether (500 ml) and stirred at 0° C. HCl in ether (60 ml) was then added to the solution, and the resulting precipitate was collected by filtration and washed with cold dry ether (3×20 ml) affording 7.21 g (41%) of 11 as white crystals. A second crop of 2.12 g (12%) could be collected as a white semicrystalline material by keeping the mother liquor in the freezer overnight. This second crop was slightly less pure than the first crop. $^1$H-NMR ($D_2O$/TMS): δ 1.36 (s, 9H, Boc); 1.52 (d, J=7.2 Hz, 3H, Me); 3.16 (m, 2H, $NCH_2$); 3.35 (m, 2H, $NCH_2$); 4.17 (q, J=7.2 Hz, 1H, CH); 5.26 (s, 2H, $CH_2Ph$); 7.40 (s, 5H, Ph). $^{13}$C-NMR ($D_2O$/TMS): δ 13.5 (Me); 27.3 (Box); 36.4 (CH); 45.5 ($NCH_2$); 55.2 (NCH2); 68.4 ($CH_2Ph$); 128.3, 128.7, 128.8 (Ph). MS(FAB+) m/z (%): 323 (100, M-HCl+H) Anal. Calcd for $C_{17}H_{27}ClN^2O_4$: C, 56.90; H, 7.58; N, 7.81; Cl, 9.88. Found: C, 55.11; H, 7.52; N, 7.93; Cl, 10.45.

EXAMPLE 47
N-(2-Boc-aminoethyl)-N-(1-thyminylacetyl) alanine Benzyl Ester (12)

N-(2-Boc-aminoethyl)alanine benzyl ester hydrochloride (11, 3.00 g, 8.4 mmol, 1.0 eq) was dissolved in dry dichloromethane (50 ml) and stirred at 0° C. under nitrogen. DIEA (1.5 ml, 8.4 mmol, 1.0 eq), DHBtOH (1.50 g, 9.2 mmol, 1.1 eq) in dichloromethane (30 ml), 1-thyminylacetic acid (1.69 g, 9.2 mmol, 1.1 eq) in dichloromethane (30 ml) and DCC (2.07 g, 10.0 mmol, 1.2 eq) in dichloromethane (40 ml) were added in that order. The reaction mixture was stirred at 0° C. for 1 h and then at 4–5° C. overnight. The precipitated DCU was filtered off and washed with dichloromethane (3×15 ml). The filtrate was washed with saturated aqueous sodium bicarbonate (3×150 ml) diluted to five times its volume, saturated aqueous potassium hydrogen sulfate (2×150 ml) diluted to three times its volume, saturated aqueous sodium chloride (1×50 ml), dried ($Na_2SO_4$), filtered and finally evaporated under reduced pressure yielding 3.83 g of crude product as a pink glassy foam. The crud product was chromatograph d (silica, 0.063–0.200 mm) using M OH/dichloromethane as the eluent (3/97, v/v until the first fraction appeared then 5/95, v/v) affording 2.87 g (70%) of 12 a white glassy foam. 12 was isolated as mixture of two conformers due to restricted rotation around the amide bond. Consequently, some of the signals in the NMR spectra were split into a major and minor component. The values provided below are for the major component. $^1$H-NMR ($CDCl_3$/TMS): δ 1.44 (s, 9H, Boc); 1.52 (d, J=7.1 Hz, 3H, ala-Me); 3.31 (m, 2H, $NCH_2$); 3.44 (m, 1H, $NCH_2$); 3.55 (m, 1H, $NCH_2$); 4.34 (q, J=7.3 Hz, 1H, CH); 4.53 (s, 2H, acetyl-$CH_2$); 5.16 (s, 2H, $CH_1Ph$); 6.90 (s, 1H, thymine-H-6); 7.35 (m, 5H, Ph). $^{13}$C-NMR ($CDCl_3$/TMS): δ 12.2 (thymine-Me); 14.3 (ala-Me); 28.3 (Boc); 39.3 (CH); 46.0 (acetyl-$CH_2$); 48.0 ($NCH_2$); 55.6 ($NCH_2$); 67.2 ($CH_2Ph$); 79.8 (Boc); 110.5 (thymine-C-5); 128.0, 128.3, 128.5, 128.6, 135.1 (Ph); 140.8 (thymine-C-6); 150.9 (thymine-C-2); 155.8 (Boc-C=O); 164.1 (thymine-C-4); 166.8 (acetyl-$CH_2$); 171.3 (ester-C=O). MS(FAB+) m/z (%): 489 (64, M+H). Anal. Calcd for $C_{24}H_{32}N_4O_7$: C, 59.01; H, 6.60; N, 11.47. Found: C, 58.55; H. 6.65; N, 11.16.

EXAMPLE 48
N-(2-Boc-aminoethyl)-N-(1-thyminylacetyl)alanine (13)

N-(2-Boc-aminoethyl)-N-(1-thyminylacetyl)alanine benzyl ester (12, 2.02 g, 4.1 mmol, 1 eq) was dissolved in MeOH (100 ml) and stirred at 0° C. under nitrogen. 10% palladium on activated carbon (1.7 g) was added and the mixture was hydrogenated at atmospheric pressure and 0° C. for 1 h at which time hydrogen uptake had ceased (91 ml, 4.1 mmol, 1 eq had been consumed). The reaction mixture was filtered through c lit which was washed thoroughly with MeOH. The collected filtrates were evaporated giving 1.65 g (100%) of 13 as a white glassy foam. 13 was isolated as a mixture of two conformers due to restricted rotation around the amide bond. Consequently, some of the signals in the NMR spectra were split into a major and minor component. The values provided below are for the major component. $^1$H-NMR (DMSO-d$_6$/TMS): δ 1.42 (d, J=7.1 Hz, 3H, ala-Me); 1.46 (s, 9H, Boc); 3.26 (m, 2H, NCH$_2$); 3.42 (m, 2H, NCH$_2$); 4.39 (q, J=7.0 Hz, 1H, CH); 4.69 (s, 2H, acetyl-CH$_2$); 7.00 (s, 1H, thymine-H-6); 11.35 (s, 1H, COOH). $^{13}$C-NMR (DMSO-d$_6$/TMS): δ 12.0 (thymine-Me); 14.8 (ala-Me); 28.3 (Boc); 33.6 (CH); 45.7 (acetyl-CH$_2$); 48.0 (NCH$_2$); 54.8 (NCH$_2$); 78.1 (Boc); 108.1 (thymine-C-5); 142.2 (thymine-C-6); 151.0 (thymine-C-2); 155.8 (Boc-C=O); 164.4 (thymine-C-4); 166.9 (acetyl-CH$_2$); 172.6 (acid–C=O). MS(FAB—) m/z (%): 397 (100, M-H); 398 (21, M-H+1); 399 (5, M-H+2). Anal. Calcd for C$_{17}$H$_{25}$N$_4$O$_7$; C, 51.25; H, 6.58; N, 14.06.

EXAMPLE 49
Chimera Macromolecule Having Peptide Nucleic Acids Section Attaching to 3' Terminus of a 2'-Deoxy Phosphorothioate Oligonucleotide Section A first section of peptide nucleic acids is prepared as per PCT patent application PCT/EP/01219. The peptide nucleic acids are prepared from the C terminus towards the N terminus using monomers having protected amine groups. Following completion of the peptide region, the terminal amine blocking group is removed and the resulting amine reacted with a 3'-C-(formyl)-2',3'-dideoxy-5'-trityl nucleotide as prepared as per the procedure of Vasseur, at. al., *J. Am. Chem. Soc.* 1992, 114, 4006. The condensation of the amine with the aldehyde moiety of the C-formyl nucleoside is effected as per the conditions of the Vasseur, ibid., to yield an intermediate oxime linkage The oxime linkage is reduced under reductive alkylation conditions of Vassour, ibid., with HCHO/NaBH$_3$CN/AcOH to yield the nucleoside connected to the peptide nucleic acid via an methyl alkylated amine linkage. An internal 2'-deoxy phosphorothioate nucleotide region is then continued from this nucleoside as per standard automatated DNA synthetic protocols (see Oligonucleotide synthesis, a practice approach, M. J. Gait ed, IRL Press, 1984).

EXAMPLE 50
Chimera Macromolecule Having Peptide Nucleic Acids Section Attaching to 5' Terminus of a Phosphorothioate Oligonucleotide Section A phosphorothioate oligonucleotide is prepare in the standard manner on a solid support as per standard protocols (see Oligonucleotides and Analogues, A Practical Approach, F. Eckstein Ed., IRL Press, 1991. The dimethoxytrityl blocking group on that nucleotide is removed in the standard manner. Peptide synthesis for the peptide region is commenced by reaction of the carboxyl end of the first peptide nucleic acid of this region with the 5' hydroxy of the last nucleotide of the DNA region. Coupling is effected via DEA in pyridine to form an ester linkage between the peptide and the nucleoside. Peptide synthesis is then continued in the manner of patent application PCT/EP/01219 to complete the peptide nucleic acid region.

EXAMPLE 51
Double-stranded Duplex Structures That Include Chimera Stand and Triple-stranded Triplex Structures That Include Chimera Strand Duplex and triplex structures will be formed with the chimera strands of Examples 42 and 43 as per the protocols of other of the above examples. Duplex structures can include duplexes between a PNA-RNA or PNA-DNA strand and a RNA strand, a PNA-RNA or PNA-DNA strand and a DNA strand, a PNA-RNA or PNA-DNA strand and a PNA strand or a PNA-RNA or PNA-DNA strand and a further chimeric PNA-DNA or PNA-RNA strand. Triplex structures can include a PNA containing chimeric strands triplexing with dsDNA or with a double-stranded PNA construct. Further triplex structures can include two of the PNA containing chimera triplexing with a single DNA or RNA strand. Additional triplex structures can include a single PNA containing chimera plus a PNA triplexing with an additional PNA containing chimera, an additional PNA strand or a DNA or RNA strand.

EXAMPLE 52
Binding Between Single strand PNA Containing Chimera and Transcription Factor or Other Protein A PNA containing chimeric strand will be used to bind to or otherwise modulate single-stranded DNA, double-stranded DNA, RNA, a transcription factor or other protein. In use of a PNA containing chimera, part of the binding between the chimera and the transcription factor or other protein will be binding between the sugar-phosphate backbone of the DNA or RNA portion of the chimera and hydrogen bonding between the ligands, e.g., nucleobases, of the PNA portion of the chimera. Binding to the sugar-phosphate backbone includes binding to phosphodiester linkages, phosphorothioate linkages or other linkages that may be used as the backbone of the DNA or RNA. In other instances, bonding can include hydrophobic contacts between hydrophobic groups on the ligands, including nucleobases, of the PNA or the nucleobases of the nucleic acid portion of the chimera with like hydrophobic groups on proteins that are being bound. Such hydrophobic groups on the chimeric strand include the methyl groups on thymine nucleobases.

EXAMPLE 53
PHA Dimer (detT-idaT) Having "Reversed" Monomer

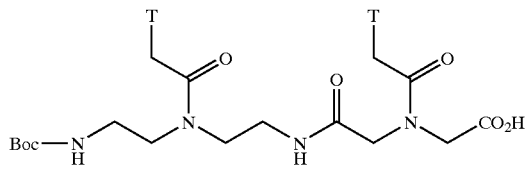

A. MonoBoc-diethylenetriamine dihydrochloride.

A solution of t-butyl-p-nitrophenyl carbonate (10 g; 0.0418 mole) in CHCl$_3$ (400 ml) was added to a solution of diethylenetriamine (45 ml; 0.417 mole) in CHCl$_3$ (250 ml) at 0° C. over a period of 3 h. Then, the reaction mixture was stirred overnight at room temperature.

The precipitate that appeared was filtered and washed with CHCl$_3$. The solvent was evaporated, first under reduced pressure with a water-aspirator, then with an oil-pump (0.05 mmHg; 50° C.).

The residue was dissolved in a mixture of ethyl acetate (50 ml) and H$_2$O (50 ml). The solution was acidified to pH 4 with 4W HCl and extracted with ethyl acetate (3×50 ml. The aqueous solution was adjusted to pH 9 with 2N NaOH and extracted with ethyl acetate (3×50 ml). Then, the aqueous phase was adjusted to pH 11.5 and extracted with ethyl acetate (10×50 ml). The combined organic phases of the last extraction were evaporated under reduced pressure and the resulting oil was dissolved in water (50 ml) and acidified to pH 5. Evaporation of water yielded a slightly yellow solid, which was thoroughly washed with ether (yield: 6.41 g; 55%).

$^1$H-NMR (D$_2$O): δ (ppm): 1.4 (s, 9H); 3.0 (t,2H); 3.3 (s broad, 4H); 3.4 (t, 2H)

B. Boc-, Z-diethylenetriamine hydrochloride.

To a solution containing the product of Example 53A (5.5 g: 19.9 mmoles) in dioxane (50 ml) / water (50 ml) adjusted at pH 11 was added a solution of benzyl-nitrophenyl carbonate (5.44 g; 19.9 mmoles) in dioxane (50 ml) at 0° C. over a period of 70 min, while maintaining the pH at 11 with 2N NaOH. The reaction mixture was then stirred at room temperature for 1.5 h.

Subsequently, ethyl ac tat (100 ml) was added and the reaction mixture was cooled at 0° C. and acidified to pH 4 with 4N HCl. A precipitate appeared in the organic phase. The two phases were separated and the organic phase filtered.

These operations (adding ethyl acetate, separating the two phases and filtering the organic phase) were repeated 3 times. A white solid (3.05 g) was collected this way. An additional 1.38 g was obtained by joining all the organic phases and adding ether. (Yield : 4.427 q; 59%) $^1$H-NMR (DMSO d6): δ (ppm): 1.5 (s, 9H); 3.0 (m, 4H); 3.4 (m, 4H); 5.1 (s, 2H); 7.4 (s, 5H); 7.1 (m,1H); 7.6 (m, 1H). MS FAB+: M+1: 338.2

C. Coupling with N-1-carboxymethylthymine.

The product of Example 53B (4 g; 10.7 mmoles), N-1-carboxymethylthymine (1.97 g; 10.7 mmoles). DhbtOH (1.75 g; 10.7 mmoles) and DIEA (1.9 ml; 11.2 mmoles) were dissolved in a mixture of CH$_2$Cl$_2$ (50 ml)/DMF (50 ml). After cooling at 0° C., DCC (2.2 g; 10.7 mmoles) was added and the reaction mixture was stirred at 0° C. for 0.5 h and 2.5 h at room temperature. Then, DCU was filtered and washed with CH$_2$Cl$_2$ (2×100 ml). The combined organic phases were washed with 1M NaHCO$_3$ (3×100 ml), 1M KHSO$_4$ (3×100 ml), H$_2$O (2×100 ml), dried over Na$_2$SO$_4$, filtered and evaporated under reduced pressure. The resulting oil was crystallized in chloroform/ether. (Yield: 4.04 g; 75%)

$^1$H-NMR (CDCl$_3$): δ (ppm): 1.4 (s,9H); 1.9 (s,3H); 3.4(m, 8H); 4.4 (d,2H); 5.1 (d,2H); 5.5 (m,1H)s 5.9 (m,1H); 6.9 (s,1H): 7.4 (s,5H); 9.0 (s,1H); MS FAB+: K+1: 504

D. Hydrogenolysis

The product of Example 53C (4 g; 7.9 mmoles) was dissolved in MeOH (150 ml). At 0° C., 10% Pd/C (1.4 g) was added. The reaction mixture was hydrogenated at 0° C. for 1 h, filtered through Celite and the solvent removed under reduced pressure to give 4. (Yield: 3,0 g; 100%)

$^1$H-NMR (CDCl$_3$): δ (ppm): 1.4 (s,9H); 1.9 (s,3H); 3.0–3.8(m); 4.6 (d,2H); 6.9 (s,1H); 7.3 (s,5H); 9.0 (s,1H). MS FAB+: M+1: 370.2

E. N-(benzyl acetate)-glycine ethyl ester hydrochloride.

At room temperature, benzyl bromoacetate (5.7 ml; 36 mmoles) was added over a period of 10 min to a solution of glycine ethyl ester hydrochloride (5 g; 36 mmoles) and triethylamine (10.43 ml; 0.072 moles) dissolved in absolute ethanol (100 ml). After 4 days at room temperature, the solvent was removed under reduced pressure. The residue was dissolved in ethyl acetate (50 ml)/H$_2$O (25 ml). After separation of the two phases, the organic phase was thoroughly washed with water (8.25 ml). After evaporation of the solvent, the resulting oil was dissolved in ether (20 ml)/water (30 ml) and acidified to pH 4.5. After separation of the two phases, the aqueous phase was concentrated and the resulting oil crystallized in cold ether. (Yield 4 g 39%);

$^1$H-NMR (CDCl$_3$): δ (ppm): 1.3 (t!3H); 4.1 (d,4H); 4.4 (q,2H); 5.3 (d,2H); 5.5 (m,1H); 7.4 (s,5H). MS FAB+: M+1: 252.1

E. Coupling N-1-carboxymethylthymine.

The product of Example 53D (2.8 g; 9.7 mmoles), N-1-carboxymethylthymine (1.79 g; 9.7 mmol s), DhbtOH (1.6 g; 9.7 mmol s) and DIEA (1.7 ml; 10 mmol s) were dissolved in a mixture of CH$_2$Cl$_2$ (30 ml)/DMF (30 ml). After cooling at 0° C., DCC (2.0 g; 9.7 moles) was added and the reaction mixture was stirred at 0° C. for 0.5 h and 4 h at room temperature. Then DCU was filtered and wash with CH$_2$Cl$_2$ (120 ml). The combined organic phases were washed with 1M NaHCO$_3$ (3×60 ml), 1M KHSO$_4$ (3×60 ml), H$_2$O (2×60 ml), dried over Na$_2$SO$_4$, filtered and evaporated under reduced pressure. The resulting oil was crystallized in chloroform (60 ml)/petroleum ether (120 ml). (Yield: 3.235 g; 80%)

$^1$H-NMR (DMSO d6): δ (ppm): 1.3 (dt,3H); 1.9 (s,3H); 4.2 (m,4H); 4.4 (d,2H); 5.3 (d,2H); 7.4 (s, 1H); 7.4 (s,5H); 11.3 (s,1H). MS FAB+: M+1: 418.1

F. Hydrogenolysis

The product of Example 53E (4 g; 9.6 mmoles) was dissolved in methanol (100 ml)/DMF (25 ml). At 0° C., 10% Pd/C (1.6 g) was added. The reaction mixture was hydrogenated at 0° C. for 1 h, filtered through Celite and the solvent removed under reduced pressure. (Yield=3.12 g; 99%)

$^1$H-NMR (DMSO d6): δ (ppm): 1.3 (dt,3H); 1.9 (s,3H); 4.0–4.5 (m); 4.9 (s,2H); 7.2 (s,1H); 11.3 (s,1H). MS FAB+: M+1: 328.1

G. Coupling

The products of Examples 53D (2.8g: 7.6 mmoles) and 53F (2.5 g; 7.6 mmoles), and DhbtOH (1.24 g; 7.6 mmoles) were dissolved in a mixture in a mixture of CH$_2$Cl$_2$ (50 ml)/DMF (50 ml). After cooling at 0° C., DCC (1.56 g; 7.6 mmoles) was added and the reaction mixture was stirred at 0° C. for 0.5 h and overnight at room temperature. Then, DCU was filtered land washed with CH2Cl$_2$ (250 ml). The combined organic phases were washed with 1M NaHCO$_3$ (3×100 ml), 1M KHSO$_4$ (3×100 ml), H$_2$O (2×100 ml), dried over Na$_2$SO$_4$, filtered and evaporated under reduced pressure. The resulting oil was crystallized in chloroform (30 ml)/petroleum ether (60 ml). This material was recrystallized in chloroform (30 ml)/petroleum ether (25 ml) to give a pure compound. (Yield: 0.60 g; 12%) MS FAB+: M+1: 418.1

H. Hydrolysis

The product of Example 53G (529 mg; 0.8 mmoles) was dissolved in absolute ethanol (100 ml). Then NaOH 1M (20 ml) was added. The reaction mixture was stirred for 30 min at room temperature and after cooling, neutralized with Dowex 50W (about 13 g). After filtration, washing with H$_2$O, ethanol and evaporation of the solvent, the residue was suspended in ether and filtered. The acid product was obtained as a white solid, pure in HPLC (Yield: 450 mg: 86%)

MS FAB+: 673 (M+Na$^+$); 617 (M Na$^+$-tBu); 595 (M+1-tBu); 573 (M Na$^+$-Boc); 551 (M+1-Boc) cl EXAMPLE 54 PNa Oligomer Having "Reversed" Monomer The dimer prepared in Example 53 was incorporated into PNA H-TT(detT-idaT)CCTCTC-LysNH$_2$ (SEQ ID NO:53) generally in accordance with Example 1. The melting temperatures, T$_m$, of complexes between this PNA and decamers 5'd(AAAAGGAGAG) (SEQ ID NO:54) and 5'd (GAGAGGAAAA) (SEQ ID NO:55) were 55° C. and 43.5° C., respectively, at pH 7. By comparison, the T$_m$ of complexes between PNA H-TTTCCTCTC-LysNH$_2$ (SEQ ID NO:56), prepared generally in accordance with Example 1, and these decamers was 58.5° C. and 40.5° C., respectively, at pH 7.

Those skilled in the art will appreciate that numerous changes and modifications may be made to the preferred embodiments of the invention and that such changes and

We claim:

1. A chimeric compound comprising a first strand section including DNA or RNA, and a second strand section including a sequence of ligands of the formula:

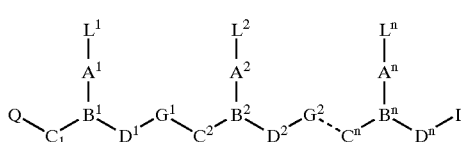

wherein:
   n is at least 2,
   each of $L^1$ and $L^n$ is independently selected from the group consisting of hydrogen, hydroxy, $(C_1-C_4)$, alkanoyl, naturally occurring nucleobases, non-naturally occurring nucleobases, aromatic moieties, DNA intercalators, nucleobase-binding groups, heterocyclic moieties, and reporter ligands; wherein at least one of $L^1$ and $L^n$ is a naturally occurring or non-naturally occurring nucleobase;
   each of $C^1$ and $C^n$ is $(CR^6R^7)$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where:
      each $R^3$ and $R^4$ is independently selected from the group consisting of hydrogen, $(C_1-C_4)$alkyl, hydroxy- or alkoxy- or alkylthio-substituted $(C_1-C_4)$ alkyl, hydroxy, alkoxy, alkylthio and amino; and
   $R^5$ is hydrogen, $(C_1-C_6)$alkyl, hydroxy-, alkoxy-, or alkylthio-substituted $(C_1-C_6)$alkyl, or $R^6$ $^{and\ R7}$ taken together complete an alicyclic or heterocyclic system;
   each of $D^1-D^n$ is $(CR^6R^7)_z$ where $R^6$ and $R^7$ are as defined above;
   each of y and z is zero or an integer from 1 to 10, the sum y+z being greater than 2 but not more than 10;
   each of $G^1-G^{n-1}$ is —$NR^3CO$—, —$NR^3CS$—, —$NR^3SO$— or —$NR^3SO_2$—, in either orientation, where $R^3$ is as defined above;
   each of $A^1-A^n$ and $B^1-B^n$ are selected such that:
      (a) A is a group of formula (IIa), (IIb), (IIc) or (IId), and B is N or $R^3N^+$; or (b) A is a group of formula (IId) and B is CH;

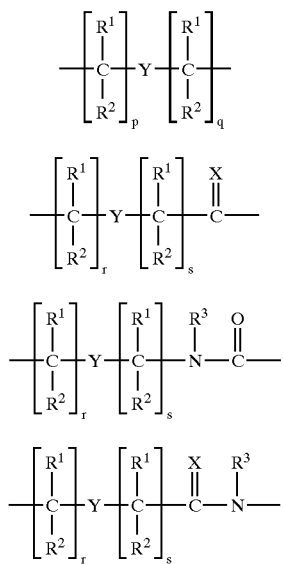

where:
X is O, S, Se, NR³, CH₂ or C(CH₃)₂;
Y is a single bond, O, S or NR⁴;
each of p and q is zero or an integer from 1 to 5, the sum p+q being not more than 10;
each of r and s is zero or an integer from 1 to 5, the sum r+s being not more than 10;
each of R¹ and R² is independently selected from the group consisting of hydrogen, (C₁–C₄)alkyl which may be hydroxy- or alkoxy- or alkylthio-substituted, hydroxy, alkoxy, alkylthio, amino and halogen; and
Q is —CO₂H, —CONR'R", —SO₃H or —SO₂NR'R" or an activated derivative of —CO₂H or —SO₃H; and
I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;
said first strand section and said second strand section being covalently bound.

2. The compound of claim 1 wherein said first strand section includes DNA.

3. A double-stranded chimeric complex, wherein: a first strand comprises a first strand section including DNA or RNA and a second strand section comprises a sequence of ligands, of the formula:

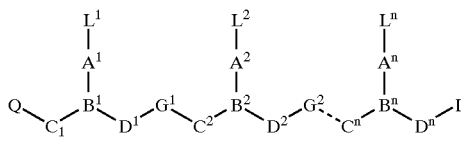

wherein:
n is at least 2,
each of L¹ and Lⁿ is independently selected from the group consisting of hydrogen, hydroxy, (C₁–C₄), alkanoyl, naturally occurring nucleobases, non-naturally occurring nucleobases, aromatic moieties, DNA intercalators, nucleobase-binding groups, heterocyclic moieties, and reporter ligands; wherein at least one of L¹ and Lⁿ is a naturally occurring or non-naturally occurring nucleobase;
each of C¹ and Cⁿ is (CR⁶R⁷) where R⁶ is hydrogen and R⁷ is selected from the group consisting of the side chains of naturally occurring alpha amino acids, or R⁶ and R⁷ are independently selected from the group consisting of hydrogen, (C₂–C₆)alkyl, aryl, aralkyl, heteroaryl, hydroxy, (C₁–C₆)alkoxy, (C₁–C₆)alkylthio, NR³R⁴ and SR⁵, where:
each R³ and R⁴ is independently selected from the group consisting of hydrogen, (C₁–C₄)alkyl, hydroxy- or alkoxy- or alkylthio-substituted (C₁–C₄) alkyl, hydroxy, alkoxy, alkylthio and amino; and
R⁵ is hydrogen, (C₁–C₆)alkyl, hydroxy-, alkoxy-, or alkylthio-substituted (C₁–C₆)alkyl, or R⁶ and R⁷ taken together complete an alicyclic or heterocyclic system;
each of D¹–Dⁿ is (CR⁶R⁷)₂ where R⁶ and R⁷ are as defined above;
each of y and z is zero or an integer from 1 to 10, the sum y+z being greater than 2 but not more than 10;
each of G¹–Gⁿ⁻¹ is —NR³CO—, —NR³CS—, —NR³SO— or —NR³SO₂—, in either orientation, where R³ is as defined above;
each of A¹–Aⁿ and B¹–Bⁿ are selected such that:
(a) A is a group of formula (IIa), (IIb), (IIc) or (IId), and B is N or R³N⁺; or
(b) A is a group of formula (IId) and B is CH;

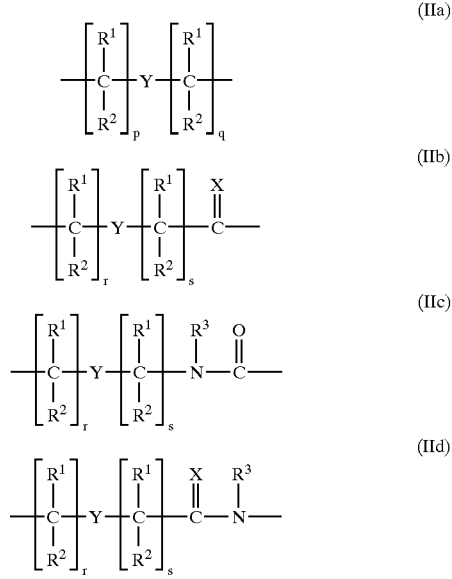

where:
X is O, S, Se, NR³, CH₂ or C(CH₃)₂;
Y is a single bond, O, S or NR⁴;
each of p and q is zero or an integer from 1 to 5, the sum p+q being not more than 10;
each of r and s is zero or an integer from 1 to 5, the sum r+s being not more than 10;
each of R¹ and R² is independently selected from the group consisting of hydrogen, (C₁–C₄)alkyl which may be hydroxy- or alkoxy- or alkylthio-substituted, hydroxy, alkoxy, alkylthio, amino and halogen; and Q is —CO₂H, —CONR'R", —SO₃H or —SO₂NR'R" or an activated derivative of —CO₂H or —SO₃H; and I is —NHR'"R"" or —NR'"C(O)R"", where R', R", R'" and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;

said first and said second strand sections being covalently bound;

a second strand comprises DNA, RNA, or a sequence of ligands covalently bound by amide, thioamide, sulfinamide, or sulfonamide linking moieties; and said first strand and said second strand interact with one another to form a duplex structure.

4. A process for inhibiting transcription of DNA comprising:

selecting DNA for which transcription is to be inhibited; and adding to a mixture containing said DNA and a transcription factor for said DNA a compound having a sequence of ligands that is complementary to a base sequence of said DNA, said compound having the formula:

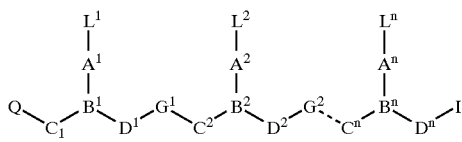

wherein:

n is at least 2, each of $L^1$ and $L^n$ is independently selected from the group consisting of hydrogen, hydroxy, ($C_1$-$C_4$), alkanoyl, naturally occurring nucleobases, non-naturally occurring nucleobases, aromatic moieties, DNA intercalators, nucleobase-binding groups, heterocyclic moieties, and reporter ligands; wherein at least one of $L^1$ and $L^n$ is a naturally occurring or non-naturally occurring nucleobase;

each of $C^1$ and $C^n$ is ($CR^6R^7$) where $R^6$ is hydrogen and $R^7$ is selected from the group consisting of the side chains of naturally occurring alpha amino acids, or $R^6$ and $R^7$ are independently selected from the group consisting of hydrogen, ($C_2$-$C_6$)alkyl, aryl, aralkyl, heteroaryl, hydroxy, ($C_1$-$C_6$)alkoxy, ($C_1$-$C_6$)alkylthio, $NR^3R^4$ and $SR^5$, where:

each $R^3$ and $R^4$ is independently selected from the group consisting of hydrogen, ($C_1$-$C_4$)alkyl, hydroxy- or alkoxy- or alkylthio-substituted ($C_1$-$C_4$) allyl, hydroxy, alkoxy, alkylthio and amino; and $R^5$ is hydrogen, ($C_1$-$C_6$)alkyl, hydroxy-, alkoxy-, or alkylthio-substituted ($C_1$-$C_6$)alkyl, or $R^6$ and $R^7$ taken together complete an alicyclic or heterocyclic system;

each of $D^1$–$D^n$ is ($CR^6R^7$)$_z$ where $R^6$ and $R^7$ are as defined above;

each of y and z is zero or an integer from 1 to 10, the sum y+z being greater than 2 but not more than 10;

each of $G^1$–$G^{n-1}$ is —NR³CO—, —NR³CS—, —NR³SO— or —NR³SO₂—, in either orientation, where R³ is as defined above;

each of $A^1$–$A^n$ and $B^1$–$B^n$ are selected such that:

(a) A is a group of formula (IIa), (IIb), (IIc) or (IId), and B is N or $R^3N^+$; or (b) A is a group of formula (IId) and B is CH;

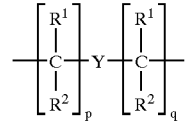

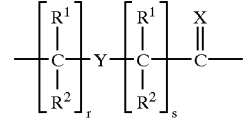

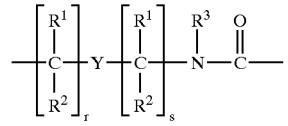

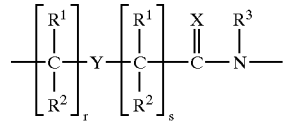

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each of $R^1$ and $R^2$ is independently selected from the group consisting of hydrogen, ($C_1$-$C_4$) alkyl which may be hydroxy- or alkoxy- or alkylthio-substituted, hydroxy, alkoxy, alkylthio, amino and halogen; and Q is —CO₂H, —CONR'R", —SO₃H or —SO₂NR'R" or an activated derivative of —CO₂H or —SO₃H; and I is —NHR'"R"" or —NR'"C(O)R"", where R', R", R'" and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;

thereby binding a plurality of said ligands to said transcription factor.

5. A hybrid complex comprising:

double-stranded DNA; and a compound that comprises a sequence of ligands, said compound having the formula:

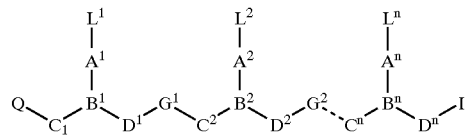

wherein:

n is at least 2, each of $L^1$ and $L^n$ is independently selected from the group consisting of hydrogen, hydroxy, ($C_1$-$C_4$), alkanoyl, naturally occurring nucleobases, non-naturally occurring nucleobases, aromatic moieties, DNA intercalators, nucleobase-binding groups, heterocyclic moieties, and reporter ligands; wherein at least one of $L^1$ and $L^n$ is a naturally occurring or non-naturally occurring nucleobase;

each of $C^1$ and $C^n$ is $(CR^6R^7)$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where:

each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino; and $R^5$ is hydrogen, $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;

each of $D^1-D^n$ is $(CR^6R^7)_z$ where $R^6$ and $R^7$ are as defined above;

each of y and z is zero or an integer from 1 to 10, the sum y+z being greater than 2 but not more than 10;

each of $G^1-G^{n-1}$ is $-NR^3CO-$, $-NR^3CS-$, $-NR^3SO-$ or $-NR^3SO_2-$, in either orientation, where $R^3$ is as defined above;

each of $A^1-A^n$ and $B^1-B^n$ are selected such that:
(a) A is a group of formula (IIa), (IIb), (IIc) or (IId), and B is N or $R^3N^+$; or
(b) A is a group of formula (IId) and B is CH;

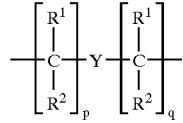  (IIa)

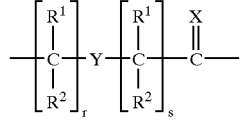  (IIb)

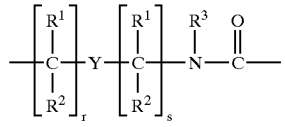  (IIc)

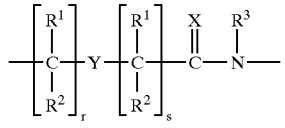  (IId)

where:
X is O, S, Se, $NR^3$, $CH_2$ or $C(CH_3)_2$;
Y is a single bond, O, S or $NR^4$;
each of p and q is zero or an integer from 1 to 5, the sum p+q being not more than 10;
each of r and s is zero or an integer from 1 to 5, the sum r+s being not more than 10;
each of $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and Q is $-CO_2H$, $-CONR'R''$, $-SO_3H$ or $-SO_2NR'R''$ or an activated derivative of $-CO_2H$ or $-SO_3H$; and I is $-NHR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;

wherein a plurality of said ligands interact with said double-stranded DNA.

6. The compound of claim 5 further comprising a step of contacting RNA polymerase with at least one of said DNA and said compound.

7. A process comprising:
forming a chimeric structure by covalently bonding a first strand section including DNA or RNA and a second strand section including a sequence of ligands of the formula:

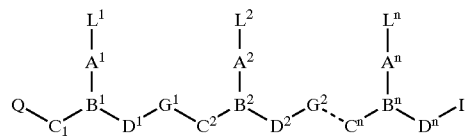

wherein:
n is at least 2,
each of $L^1$ and $L^n$ is independently selected from the group consisting of hydrogen, hydroxy, $(C_1-C_4)$, alkanoyl, naturally occurring nucleobases, non-naturally occurring nucleobases, aromatic moieties, DNA intercalators, nucleobase-binding groups, heterocyclic moieties, and reporter ligands; wherein at least one of $L^1$ and $L^n$ is a naturally occurring or non-naturally occurring nucleobase;

each of $C^1$ and $C^n$ is $(CR^6R^7)$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where:

each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino; and $R^5$ is hydrogen, $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;

each of $D^1-D^n$ is $(CR^6R^7)_z$ where $R^6$ and $R^7$ are as defined above;

each of y and z is zero or an integer from 1 to 10, the sum y+z being greater than 2 but not more than 10;

each of $G^1-G^{n-1}$ is $-NR^3CO-$, $-NR^3CS-$, $-NR^3SO-$ or $-NR^3SO_2-$, in either orientation, where $R^3$ is as defined above;

each of $A^1-A^n$ and $B^1-B^n$ are selected such that:
(a) A is a group of formula (IIa), (IIb), (IIc) or (IId), and B is N or $R^3N^+$; or (b) A is a group of formula (IId) and B is CH;

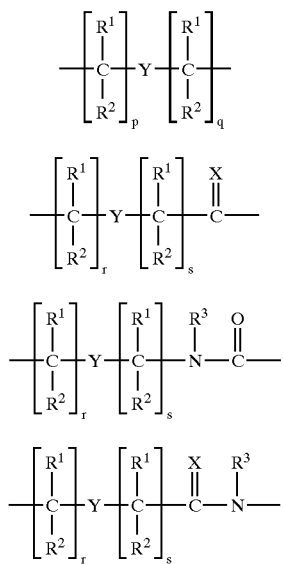

where:
X is O, S, Se, NR³, CH₂ or C(CH₃)₂;
Y is a single bond, O, S or NR⁴;
each of p and q is zero or an integer from 1 to 5, the sum p+q being not more than 10;
each of r and s is zero or an integer from 1 to 5, the sum r+s being not more than 10;
each of R¹ and R² is independently selected from the group consisting of hydrogen, (C₁–C₄)alkyl which may be hydroxy- or alkoxy- or alkylthio-substituted, hydroxy, alkoxy, alkylthio, amino and halogen; and
Q is —CO₂H, —CONR'R", —SO₃H or —SO₂NR'R" or an activated derivative of —CO₂H or —SO₃H; and
I is —NHR'''R"" or —NR'''C(O)R"", where R', R", R''' and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;

wherein a plurality of said ligands bind with said transcription factor; and introducing said chimeric structure into a cell.

8. The process of claim 7 further including selecting said ligands and said DNA or RNA such that a plurality of said ligands bind with the sugar-phosphate backbone of said RNA or DNA.

9. A process comprising:
forming a compound that comprises a sequence of ligands of the formula:

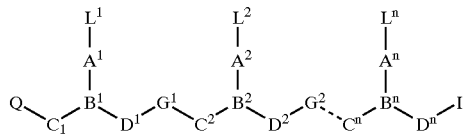

wherein:
n is at least 2,
each of L¹ and Lⁿ is independently selected from the group consisting of hydrogen, hydroxy, (C₁–C₄), alkanoyl, naturally occurring nucleobases, non-naturally occurring nucleobases, aromatic moieties, DNA intercalators, nucleobase-binding groups, heterocyclic moieties, and reporter ligands; wherein at least one of L¹ and Lⁿ is a naturally occurring or non-naturally occurring nucleobase;
each of C¹ and Cⁿ is (CR⁶R⁷) where R⁶ is hydrogen and R⁷ is selected from the group consisting of the side chains of naturally occurring alpha amino acids, or R⁶ and R⁷ are independently selected from the group consisting of hydrogen, (C₂–C₆)alkyl, aryl, aralkyl, heteroaryl, hydroxy, (C₁–C₆)alkoxy, (C₁–C₆) alkylthio, NR³R⁴ and SR⁵, where:
each R³ and R⁴ is independently selected from the group consisting of hydrogen, (C₁–C₄)alkyl, hydroxy- or alkoxy- or alkylthio-substituted (C₁–C₄)alkyl, hydroxy, alkoxy, alkylthio and amino; and
R⁵ is hydrogen, (C₁–C₆)alkyl, hydroxy-, alkoxy-, or alkylthio-substituted (C₁–C₆)alkyl, or R⁶ and R⁷ taken together complete an alicyclic or heterocyclic system;
each of D¹–Dⁿ is (CR⁶R⁷)z where R⁶ and R⁷ are as defined above;
each of y and z is zero or an integer from 1 to 10, the sum y+z being greater than 2 but not more than 10;
each of G¹–G$^{n-1}$ is —NR³CO—, —NR³CS—, —NR³SO— or —NR³SO₂—, in either orientation, where R³ is as defined above;
each of A¹–Aⁿ and B¹–Bⁿ are selected such that:
(a) A is a group of formula (IIa), (IIb), (IIc) or (IId), and B is N or R³N⁺; or
(b) A is a group of formula (IId) and B is CH;

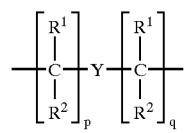

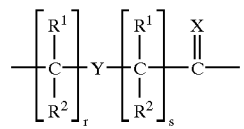

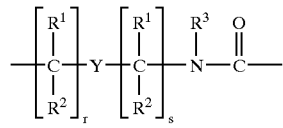

-continued

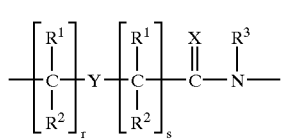

(IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each of $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and Q is —$CO_2H$, —$CONR^4R''$, —$SO_3H$ or —$SO_2NHR^7$ or an activated derivative of —$CO_2H$ or —$SO_3H$; and I is —NHR'''R'''' or —NR'''C(O)R'''', where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers;

wherein a plurality of said ligands bind to a protein; and introducing said structure into a cell.

* * * * *

UNITED STATES PATENT AND TRADEMARK OFFICE
CERTIFICATE OF CORRECTION

PATENT NO. : 6,770,738 B1  Page 1 of 1
DATED : August 3, 2004
INVENTOR(S) : Ecker et al.

It is certified that error appears in the above-identified patent and that said Letters Patent is hereby corrected as shown below:

Title page,
Item [60], Related U.S. Application Data, please delete "May 19, 1992" and insert -- May 22, 1992 --.

Column 1,
Line 12, please delete "May 19, 1992" and insert -- May 22, 1992 --.

Signed and Sealed this

Twenty-seventh Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,770,738 B1
DATED : August 3, 2004
INVENTOR(S) : David J. Ecker et al.

It is certified that error appears in the above-identified patent and that said Letters Patent is hereby corrected as shown below:

Column 107,
Line 53, delete "$C_1$" and insert -- $C^1$ --;

Column 108,
Line 55, delete "$^{and\ R7}$" and insert -- and $R^7$ --;

Column 109,
Line 61, delete "$C_1$" and insert -- $C^1$ --;

Column 111,
Line 30, delete "$C_1$" and insert -- $C^1$ --;
Line 53, delete "allyl" and insert -- alkyl --;

Column 112,
Line 63, delete "$C_1$" and insert -- $C^1$ --;

Column 114,
Line 29, delete "$C_1$" and insert -- $C^1$ --;

Column 116,
Line 7, delete "$C_1$" and insert -- $C^1$ --;

Column 118,
Line 1, delete "-CONR$^4$R' " and insert -- -CONR'R" --;
Line 2, delete "-SO$_2$NHR$^7$" and insert -- SO$_2$NR'R" --.

Signed and Sealed this

Eighteenth Day of April, 2006

JON W. DUDAS
*Director of the United States Patent and Trademark Office*

SEQUENCE LISTING

<160> NUMBER OF SEQ ID NOS: 89

<210> SEQ ID NO 1
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
      N-acetyl(2-aminoethyl)glycine through the N-acetyl
      group at position 1 of the base."
<220> FEATURE:
<221> NAME/KEY: misc_feature
<222> LOCATION: (3)..(3)
<223> OTHER INFORMATION: /note= "Heterocyclic base is attached to
      N-acetyl(2-aminoethyl)glycine through the N-acetyl
      group at position 9 of the base."
<220> FEATURE:
<221> NAME/KEY: misc_feature
<222> LOCATION: (4)..(5)
<223> OTHER INFORMATION: /note= "Heterocyclic base is attached to
      N-acetyl(2-aminoethyl)glycine through the N-acetyl
      group at position 1 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl)glycine through the N-acetyl
      group at position 9 of the base."
<220> FEATURE:
<221> NAME/KEY: misc_feature
<222> LOCATION: (7)..(10)
<223> OTHER INFORMATION: /note= "Heterocyclic base is attached to
      N-acetyl(2-aminoethyl)glycine through the N-acetyl
      group at position 1 of the base."

<400> SEQUENCE: 1

Xaa Xaa Xaa Xaa Xaa Xaa Xaa Xaa Xaa Xaa Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(10)
<223> OTHER INFORMATION: /note= "Heterocyclic base is attached to
      N-Acetyl (2-aminoethyl) glycine through the
      N-acetyl group at position 1 of the base."

<400> SEQUENCE: 2

Xaa Xaa Xaa Xaa Xaa Xaa Xaa Xaa Xaa Xaa Lys
1               5                   10

<210> SEQ ID NO 3
<211> LENGTH: 20
<212> TYPE: DNA
<213> ORGANISM: Artificial Sequence
<220> FEATURE:
<223> OTHER INFORMATION: Novel Sequence

<400> SEQUENCE: 3

-continued

```
aaaaaaaaaa tttttttttt                                              20

<210> SEQ ID NO 4
<211> LENGTH: 20
<212> TYPE: DNA
<213> ORGANISM: Artificial Sequence
<220> FEATURE:
<223> OTHER INFORMATION: Novel Sequence

<400> SEQUENCE: 4
aaaaagaaaa ttttcttttt                                              20

<210> SEQ ID NO 5
<211> LENGTH: 10
<212> TYPE: DNA
<213> ORGANISM: Artificial Sequence
<220> FEATURE:
<223> OTHER INFORMATION: Novel Sequence

<400> SEQUENCE: 5
aagaagaaaa                                                         10

<210> SEQ ID NO 6
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(5)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (7)..(10)
<223> OTHER INFORMATION: /note= "Heterocyclic base is attached to
      N-acetyl(2-aminoethyl) glycine through the
      N-acetyl group at position 1 of the base."

<400> SEQUENCE: 6

Xaa Xaa Xaa Xaa Xaa Xaa Xaa Xaa Xaa Xaa Lys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(6)
<223> OTHER INFORMATION: /note= "Heterocyclic base is attached to
      N-acetyl(2-aminoethyl) glycine through the
      N-acetyl group at position 1 of the base."

<400> SEQUENCE: 7

Xaa Xaa Xaa Xaa Xaa Xaa Lys
1               5

<210> SEQ ID NO 8
```

```
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(10)
<223> OTHER INFORMATION: /note= "Heterocyclic base is attached to
      N-acetyl(2-aminoethyl) glycine through the
      N-acetyl group at position 1 of the base."

<400> SEQUENCE: 8

Xaa Xaa Xaa Xaa Xaa Xaa Xaa Xaa Xaa Xaa Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(7)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (8)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(10)
<223> OTHER INFORMATION: /note= "Heterocyclic base is attached to
      N-acetyl(2-aminoethyl) glycine through the
      N-acetyl group at position 1 of the base."

<400> SEQUENCE: 9

Xaa Xaa Xaa Xaa Xaa Xaa Xaa Xaa Xaa Xaa Lys
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Novel Sequence
```

```
<220> FEATURE:
<221> NAME/KEY: misc_feature
<222> LOCATION: (1)..(1)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (2)..(2)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (3)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(6)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (7)..(7)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (8)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (11)..(12)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (13)..(13)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (14)..(15)
<223> OTHER INFORMATION: /note= "Heterocyclic base is attached to
      N-acetyl(2-aminoethyl) glycine through the
      N-acetyl group at position 1 of the base."

<400> SEQUENCE: 10

Xaa Xaa Xaa Xaa Xaa Xaa Xaa Xaa Xaa Xaa Xaa Xaa Xaa Xaa Xaa
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: Novel Sequence
```

-continued

```
<220> FEATURE:
<221> NAME/KEY: misc_feature
<222> LOCATION: (1)..(2)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (3)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(7)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (8)..(9)
<223> OTHER INFORMATION: /note= "Heterocyclic base is attached to
      N-acetyl(2-aminoethyl) glycine through the
      N-acetyl group at position 1 of the base."

<400> SEQUENCE: 11

Xaa Xaa Xaa Xaa Xaa Xaa Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (3)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(7)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (8)..(9)
<223> OTHER INFORMATION: /note= "Heterocyclic base is attached to
      N-acetyl(2-aminoethyl) glycine through the
      N-acetyl group at position 9 of the base."

<400> SEQUENCE: 12

Xaa Xaa Xaa Xaa Xaa Xaa Xaa Xaa Xaa
1               5

<210> SEQ ID NO 13
<211> LENGTH: 15
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
      N-acetyl(2-aminoethyl) glycine through the
```

```
      N-acetyl group at position 1 of the base."
<220> FEATURE:
<221> NAME/KEY: misc_feature
<222> LOCATION: (3)..(3)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (4)..(7)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (8)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (11)..(13)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (14)..(14)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (15)..(15)
<223> OTHER INFORMATION: /note= "Heterocyclic base is attached to
      N-acetyl(2-aminoethyl) glycine through the
      N-acetyl group at position 1 of the base."

<400> SEQUENCE: 13

Xaa Xaa Xaa Xaa Xaa Xaa Xaa Xaa Xaa Xaa Xaa Xaa Xaa Xaa Xaa
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(1)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (2)..(2)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (3)..(4)
<223> OTHER INFORMATION: /note= "Heterocyclic base is attached to
      N-acetyl(2-aminoethyl) glycine through the
```

```
    N-acetyl group at position 1 of the base."
<220> FEATURE:
<221> NAME/KEY: misc_feature
<222> LOCATION: (5)..(6)
<223> OTHER INFORMATION: /note= "Heterocyclic base is attached to
    N-acetyl(2-aminoethyl) glycine through the
    N-acetyl group at position 9 of the base."
<220> FEATURE:
<221> NAME/KEY: misc_feature
<222> LOCATION: (7)..(7)
<223> OTHER INFORMATION: /note= "Heterocyclic base is attached to
    N-acetyl(2-aminoethyl) glycine through the
    N-acetyl group at position 9 of the base."
<220> FEATURE:
<221> NAME/KEY: misc_feature
<222> LOCATION: (8)..(8)
<223> OTHER INFORMATION: /note= "Heterocyclic base is attached to
    N-acetyl(2-aminoethyl) glycine through the
    N-acetyl group at position 9 of the base."
<220> FEATURE:
<221> NAME/KEY: misc_feature
<222> LOCATION: (9)..(9)
<223> OTHER INFORMATION: /note= "Heterocyclic base is attached to
    N-acetyl(2-aminoethyl) glycine through the
    N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
    N-acetyl(2-aminoethyl) glycine through the
    N-acetyl group at position 9 of the base."
<220> FEATURE:
<221> NAME/KEY: misc_feature
<222> LOCATION: (11)..(12)
<223> OTHER INFORMATION: /note= "Heterocyclic base is attached to
    N-acetyl(2-aminoethyl) glycine through the
    N-acetyl group at position 1 of the base."
<220> FEATURE:
<221> NAME/KEY: misc_feature
<222> LOCATION: (13)..(13)
<223> OTHER INFORMATION: /note= "Heterocyclic base is attached to
    N-acetyl(2-aminoethyl) glycine through the
    N-acetyl group at position 9 of the base."
<220> FEATURE:
<221> NAME/KEY: misc_feature
<222> LOCATION: (14)..(15)
<223> OTHER INFORMATION: /note= "Heterocyclic base is attached to
    N-acetyl(2-aminoethyl) glycine through the
    N-acetyl group at position 1 of the base."

<400> SEQUENCE: 14

Xaa Xaa Xaa Xaa Xaa Xaa Xaa Xaa Xaa Xaa Xaa Xaa Xaa Xaa Xaa
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
    N-acetyl(2-aminoethyl) glycine through the
    N-acetyl group at position 9 of the base."
<220> FEATURE:
<221> NAME/KEY: misc_feature
<222> LOCATION: (3)..(3)
<223> OTHER INFORMATION: /note= "Heterocyclic base is attached to
    N-acetyl(2-aminoethyl) glycine through the
    N-acetyl group at position 1 of the base."
<220> FEATURE:
<221> NAME/KEY: misc_feature
<222> LOCATION: (4)..(4)
<223> OTHER INFORMATION: /note= "Heterocyclic base is attached to
    N-acetyl(2-aminoethyl) glycine through the
```

```
     N-acetyl group at position 9 of the base."
<220> FEATURE:
<221> NAME/KEY: misc_feature
<222> LOCATION: (5)..(5)
<223> OTHER INFORMATION: /note= "Heterocyclic base is attached to
     N-acetyl(2-aminoethyl) glycine through the
     N-acetyl group at position 1 of the base."
<220> FEATURE:
<221> NAME/KEY: misc_feature
<222> LOCATION: (6)..(8)
<223> OTHER INFORMATION: /note= "Heterocyclic base is attached to
     N-acetyl(2-aminoethyl) glycine through the
     N-acetyl group at position 9 of the base."

<400> SEQUENCE: 15

Xaa Xaa Xaa Xaa Xaa Xaa Xaa Xaa Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(4)
<223> OTHER INFORMATION: /note= "Heterocyclic base is attached to
     N-acetyl(2-aminoethyl) glycine through the
     N-acetyl group at position 1 of the base."
<220> FEATURE:
<221> NAME/KEY: misc_feature
<222> LOCATION: (5)..(5)
<223> OTHER INFORMATION: /note= "Heterocyclic base is attached to
     N-acetyl(2-aminoethyl) glycine through the
     N-acetyl group at position 9 of the base."
<220> FEATURE:
<221> NAME/KEY: misc_feature
<222> LOCATION: (6)..(9)
<223> OTHER INFORMATION: /note= "Heterocyclic base is attached to
     N-acetyl(2-aminoethyl) glycine through the
     N-acetyl group at position 1 of the base."

<400> SEQUENCE: 16

Xaa Xaa Xaa Xaa Xaa Xaa Xaa Xaa Xaa
1               5

<210> SEQ ID NO 17
<211> LENGTH: 16
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(9)
<223> OTHER INFORMATION: /note= "Heterocyclic base is attached to
     N-acetyl(2-aminoethyl) glycine through the
     N-acetyl group at position 1 of the base."
<220> FEATURE:
<221> NAME/KEY: misc_feature
<222> LOCATION: (10)..(16)
<223> OTHER INFORMATION: /note= "Heterocyclic base is attached to
     N-acetyl(2-aminoethyl) glycine through the
     N-acetyl group at position 9 of the base."

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

<210> SEQ ID NO 18
<211> LENGTH: 16
<212> TYPE: PRT
```

```
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(7)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (8)..(16)
<223> OTHER INFORMATION: /note= "Heterocyclic base is attached to
      N-acetyl(2-aminoethyl) glycine through the
      N-acetyl group at position 1 of the base."

<400> SEQUENCE: 18

Xaa Xaa Xaa Xaa Xaa Xaa Xaa Xaa Xaa Xaa Xaa Xaa Xaa Xaa Xaa Xaa
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (3)..(3)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (4)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(7)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (8)..(10)
<223> OTHER INFORMATION: /note= "Heterocyclic base is attached to
      N-acetyl(2-aminoethyl) glycine through the
      N-acetyl group at position 9 of the base."

<400> SEQUENCE: 19

Xaa Xaa Xaa Xaa Xaa Xaa Xaa Xaa Xaa Xaa
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
```

```
<222> LOCATION: (3)..(3)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (4)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (7)..(7)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (8)..(8)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 1 of the base."

<400> SEQUENCE: 20

Xaa Xaa Xaa Xaa Xaa Xaa Xaa Xaa Xaa Xaa
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(5)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (7)..(7)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
```

```
<222> LOCATION: (8)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (11)..(11)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (12)..(12)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (13)..(13)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (14)..(14)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (15)..(15)
<223> OTHER INFORMATION: /note= "Heterocyclic base is attached to
      N-acetyl(2-aminoethyl) glycine through the
      N-acetyl group at position 1 of the base."

<400> SEQUENCE: 21

Xaa Xaa Xaa Xaa Xaa Xaa Xaa Xaa Xaa Xaa Xaa Xaa Xaa Xaa Xaa
1               5                   10                  15

<210> SEQ ID NO 22
<211> LENGTH: 29
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (7)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
```

```
<222> LOCATION: (9)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (11)..(12)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (13)..(16)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (17)..(17)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (18)..(18)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (19)..(19)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (20)..(20)
<223> OTHER INFORMATION: /note= "Heterocyclic base is attached to
      N-acetyl(2-aminoethyl) glycine through the
      N-acetyl group at position 9 of the base."

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys Lys Lys Lys Lys Lys Lys Lys Lys
            20                  25

<210> SEQ ID NO 23
<211> LENGTH: 21
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(1)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (2)..(8)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (9)..(11)
<223> OTHER INFORMATION: /note= "Heterocyclic base is attached to
      N-acetyl(2-aminoethyl) glycine through the
```

-continued

```
        N-acetyl group at position 9 of the base."
<220> FEATURE:
<221> NAME/KEY: misc_feature
<222> LOCATION: (12)..(12)
<223> OTHER INFORMATION: /note= "Heterocyclic base is attached to
        N-acetyl(2-aminoethyl) glycine through the
        N-acetyl group at position 1 of the base."
<220> FEATURE:
<221> NAME/KEY: misc_feature
<222> LOCATION: (13)..(13)
<223> OTHER INFORMATION: /note= "Heterocyclic base is attached to
        N-acetyl(2-aminoethyl) glycine through the
        N-acetyl group at position 9 of the base."
<220> FEATURE:
<221> NAME/KEY: misc_feature
<222> LOCATION: (14)..(15)
<223> OTHER INFORMATION: /note= "Heterocyclic base is attached to
        N-acetyl(2-aminoethyl) glycine through the
        N-acetyl group at position 1 of the base."
<220> FEATURE:
<221> NAME/KEY: misc_feature
<222> LOCATION: (16)..(18)
<223> OTHER INFORMATION: /note= "Heterocyclic base is attached to
        N-acetyl(2-aminoethyl) glycine through the
        N-acetyl group at position 9 of the base."
<220> FEATURE:
<221> NAME/KEY: misc_feature
<222> LOCATION: (19)..(19)
<223> OTHER INFORMATION: /note= "Heterocyclic base is attached to
        N-acetyl(2-aminoethyl) glycine through the
        N-acetyl group at position 1 of the base."
<220> FEATURE:
<221> NAME/KEY: misc_feature
<222> LOCATION: (20)..(20)
<223> OTHER INFORMATION: /note= "Heterocyclic base is attached to
        N-acetyl(2-aminoethyl) glycine through the
        N-acetyl group at position 9 of the base."

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys
            20

<210> SEQ ID NO 24
<211> LENGTH: 20
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(1)
<223> OTHER INFORMATION: /note= "Heterocyclic base is attached to
        N-acetyl(2-aminoethyl) glycine through the
        N-acetyl group at position 9 of the base."
<220> FEATURE:
<221> NAME/KEY: misc_feature
<222> LOCATION: (2)..(2)
<223> OTHER INFORMATION: /note= "Heterocyclic base is attached to
        N-acetyl(2-aminoethyl) glycine through the
        N-acetyl group at position 1 of the base."
<220> FEATURE:
<221> NAME/KEY: misc_feature
<222> LOCATION: (3)..(3)
<223> OTHER INFORMATION: /note= "Heterocyclic base is attached to
        N-acetyl(2-aminoethyl) glycine through the
        N-acetyl group at position 9 of the base."
<220> FEATURE:
<221> NAME/KEY: misc_feature
<222> LOCATION: (4)..(4)
<223> OTHER INFORMATION: /note= "Heterocyclic base is attached to
        N-acetyl(2-aminoethyl) glycine through the
        N-acetyl group at position 1 of the base."
<220> FEATURE:
<221> NAME/KEY: misc_feature
```

```
<222> LOCATION: (5)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (7)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(10)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (11)..(12)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (13)..(13)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (14)..(14)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (15)..(16)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (17)..(17)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (18)..(18)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (19)..(19)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (20)..(20)
<223> OTHER INFORMATION: /note= "Heterocyclic base is attached to
      N-acetyl(2-aminoethyl) glycine through the
      N-acetyl group at position1 of the base."

<400> SEQUENCE: 24

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20
```

```
<210> SEQ ID NO 25
<211> LENGTH: 21
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(7)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (8)..(8)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (10)..(11)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (12)..(14)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (15)..(15)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (16)..(17)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (18)..(18)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (19)..(19)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (20)..(20)
<223> OTHER INFORMATION: /note= "Heterocyclic base is attached to
      N-acetyl(2-aminoethyl) glycine through the
      N-acetyl group at position 1 of the base."

<400> SEQUENCE: 25

Xaa Xaa Xaa Xaa Xaa Xaa Xaa Xaa Xaa Xaa Xaa Xaa Xaa Xaa Xaa Xaa
1               5                   10                  15
```

-continued

Xaa Xaa Xaa Xaa Lys
            20

<210> SEQ ID NO 26
<211> LENGTH: 20
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(5)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (7)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (11)..(12)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (13)..(16)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (17)..(17)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (18)..(18)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (19)..(19)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (20)..(20)
<223> OTHER INFORMATION: /note= "Heterocyclic base is attached to
      N-acetyl(2-aminoethyl) glycine through the
      N-acetyl group at position 9 of the base."

<400> SEQUENCE: 26

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 27
<211> LENGTH: 21
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(1)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (2)..(2)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (3)..(4)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (5)..(5)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (6)..(8)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (9)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (11)..(11)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (12)..(12)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (13)..(13)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (14)..(14)
<223> OTHER INFORMATION: /note= "Heterocyclic base is attached to
      N-acetyl(2-aminoethyl) glycine through the
      N-acetyl group at position 9 of the base."
```

```
<220> FEATURE:
<221> NAME/KEY: misc_feature
<222> LOCATION: (15)..(15)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (16)..(16)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (17)..(17)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (18)..(19)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (20)..(20)
<223> OTHER INFORMATION: /note= "Heterocyclic base is attached to
      N-acetyl(2-aminoethyl) glycine through the
      N-acetyl group at position 1 of the base."

<400> SEQUENCE: 27

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys
            20

<210> SEQ ID NO 28
<211> LENGTH: 12
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(5)
<223> OTHER INFORMATION: /note= "Beat isoform of alanine."
<220> FEATURE:
<221> NAME/KEY: misc_feature
<222> LOCATION: (6)..(6)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (7)..(11)
<223> OTHER INFORMATION: /note= "Heterocyclic base is attached to
      N-acetyl(2-aminoethyl) glycine through the
      N-acetyl group at position 1 of the base."

<400> SEQUENCE: 28

Xaa Xaa Xaa Xaa Ala Xaa Xaa Xaa Xaa Xaa Xaa Lys
1               5                   10

<210> SEQ ID NO 29
<211> LENGTH: 12
<212> TYPE: PRT
<213> ORGANISM: Artificial Sequence
```

```
<220> FEATURE:
<223> OTHER INFORMATION: Novel Sequence
<220> FEATURE:
<221> NAME/KEY: misc_feature
<222> LOCATION: (1)..(4)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (5)..(5)
<223> OTHER INFORMATION: /note= "Beat isoform of alanine."
<220> FEATURE:
<221> NAME/KEY: misc_feature
<222> LOCATION: (6)..(11)
<223> OTHER INFORMATION: /note= "Heterocyclic base is attached to
      N-acetyl(2-aminoethyl) glycine through the
      N-acetyl group at position 1 of the base."

<400> SEQUENCE: 29

Xaa Xaa Xaa Xaa Ala Xaa Xaa Xaa Xaa Xaa Lys
1               5                   10

<210> SEQ ID NO 30
<211> LENGTH: 26
<212> TYPE: DNA
<213> ORGANISM: Artificial Sequence
<220> FEATURE:
<223> OTHER INFORMATION: Novel Sequence

<400> SEQUENCE: 30
aaaaagaaaa gtcgacaaaa agaaaa                                          26

<210> SEQ ID NO 31
<211> LENGTH: 20
<212> TYPE: DNA
<213> ORGANISM: Artificial Sequence
<220> FEATURE:
<223> OTHER INFORMATION: Novel Sequence

<400> SEQUENCE: 31
aaaaaaaaaa tttttttttt                                                 20

<210> SEQ ID NO 32
<211> LENGTH: 38
<212> TYPE: DNA
<213> ORGANISM: Artificial Sequence
<220> FEATURE:
<223> OTHER INFORMATION: Novel Sequence

<400> SEQUENCE: 32
gtcgacaaaa agaaaagtcg actttttcttt ttgtcgac                            38

<210> SEQ ID NO 33
<211> LENGTH: 20
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<222> LOCATION: (8)..(13)
<223> OTHER INFORMATION: N is any nucleotide

<400> SEQUENCE: 33
tttttttnnn nnntttttttt                                                20

<210> SEQ ID NO 34
<211> LENGTH: 16
```

```
<212> TYPE: DNA
<213> ORGANISM: Artificial Sequence
<220> FEATURE:
<223> OTHER INFORMATION: Novel Sequence

<400> SEQUENCE: 34
gatccaaaaa aaaaag                                                    16

<210> SEQ ID NO 35
<211> LENGTH: 16
<212> TYPE: DNA
<213> ORGANISM: Artificial Sequence
<220> FEATURE:
<223> OTHER INFORMATION: Novel Sequence

<400> SEQUENCE: 35
gatccttttt tttttg                                                    16

<210> SEQ ID NO 36
<211> LENGTH: 16
<212> TYPE: DNA
<213> ORGANISM: Artificial Sequence
<220> FEATURE:
<223> OTHER INFORMATION: Novel Sequence

<400> SEQUENCE: 36 tcgactttc tttttg                                                     16

<210> SEQ ID NO 37
<211> LENGTH: 16
<212> TYPE: DNA
<213> ORGANISM: Artificial Sequence
<220> FEATURE:
<223> OTHER INFORMATION: Novel Sequence

<400> SEQUENCE: 37
tcgacaaaaa gaaaag                                                    16

<210> SEQ ID NO 38
<211> LENGTH: 16
<212> TYPE: DNA
<213> ORGANISM: Artificial Sequence
<220> FEATURE:
<223> OTHER INFORMATION: Novel Sequence

<400> SEQUENCE: 38
caagaagaaa actgca                                                    16

<210> SEQ ID NO 39
<211> LENGTH: 16
<212> TYPE: DNA
<213> ORGANISM: Artificial Sequence
<220> FEATURE:
<223> OTHER INFORMATION: Novel Sequence

<400> SEQUENCE: 39
gttttcttct tctgca                                                    16

<210> SEQ ID NO 40
<211> LENGTH: 9
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(8)
```

```
<223> OTHER INFORMATION: /note= "Heterocyclic base is attached to
      N-acetyl(2-aminoethyl) glycine through the
      N-acetyl group at position 1 of the base."

<400> SEQUENCE: 40

Xaa Xaa Xaa Xaa Xaa Xaa Xaa Xaa Lys
1               5

<210> SEQ ID NO 41
<211> LENGTH: 5
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(5)
<223> OTHER INFORMATION: /note= "Heterocyclic base is attached to
      N-acetyl(2-aminoethyl) glycine through the
      N-acetyl group at position 1 of the base."

<400> SEQUENCE: 41

Xaa Xaa Xaa Xaa Xaa
1               5

<210> SEQ ID NO 42
<211> LENGTH: 196
<212> TYPE: DNA
<213> ORGANISM: Artificial Sequence
<220> FEATURE:
<223> OTHER INFORMATION: Novel Sequence

<400> SEQUENCE: 42
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaatt tttttttttt tttttttttt     120
tttttttttt tttttttttt tttttttttt tttttttttt tttttttttt tttttttttt     180
tttttttttt tttttt                                                    196

<210> SEQ ID NO 43
<211> LENGTH: 10
<212> TYPE: DNA
<213> ORGANISM: Artificial Sequence
<220> FEATURE:
<223> OTHER INFORMATION: Novel Sequence

<400> SEQUENCE: 43
aaaagaaaaa                                                            10

<210> SEQ ID NO 44
<211> LENGTH: 20
<212> TYPE: DNA
<213> ORGANISM: Artificial Sequence
<220> FEATURE:
<223> OTHER INFORMATION: Novel Sequence

<400> SEQUENCE: 44
aaaagaagaa ttcttctttt                                                 20

<210> SEQ ID NO 45
<211> LENGTH: 8
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
```

```
<222> LOCATION: (1)..(7)
<223> OTHER INFORMATION: /note= "Heterocyclic base is attached to
      N-acetyl(2-aminoethyl) glycine through the
      N-acetyl group at position 1 of the base."

<400> SEQUENCE: 45

Xaa Xaa Xaa Xaa Xaa Xaa Xaa Lys
1               5

<210> SEQ ID NO 46
<211> LENGTH: 50
<212> TYPE: DNA
<213> ORGANISM: Artificial Sequence
<220> FEATURE:
<223> OTHER INFORMATION: Novel Sequence

<400> SEQUENCE: 46
aaacagggca ggaaacagca tattttcttt taaaattagc aggaagatgg         50

<210> SEQ ID NO 47
<211> LENGTH: 15
<212> TYPE: DNA
<213> ORGANISM: Artificial Sequence
<220> FEATURE:
<223> OTHER INFORMATION: Novel Sequence

<400> SEQUENCE: 47
tagttgtgac gtaca                                               15

<210> SEQ ID NO 48
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(1)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (2)..(3)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (4)..(4)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (5)..(6)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (7)..(7)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (8)..(8)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
```

```
<222> LOCATION: (9)..(9)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 1 of the base."

<400> SEQUENCE: 48

Xaa Xaa Xaa Xaa Xaa Xaa Xaa Xaa Xaa Xaa Lys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(1)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (2)..(2)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (3)..(3)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (4)..(4)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (5)..(6)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (7)..(7)
<223> OTHER INFORMATION: /note= "Heterocyclic base is attached to
      N-acetyl(2-aminoethyl) glycine through the
      N-acetyl group at position 9 of the base."
<220> FEATURE:
<221> NAME/KEY: misc_feature
<222> LOCATION: (8)..(9)
<223> OTHER INFORMATION: /note= "Heterocyclic base is attached to
      N-acetyl(2-aminoethyl) glycine through the
      N-acetyl group at position 1 of the base."
<220> FEATURE:
<221> NAME/KEY: misc_feature
<222> LOCATION: (10)..(10)
<223> OTHER INFORMATION: /note= "Heterocyclic base is attached to
      N-acetyl(2-aminoethyl) glycine through the
      N-acetyl group at position 9 of the base."

<400> SEQUENCE: 49

Xaa Xaa Xaa Xaa Xaa Xaa Xaa Xaa Xaa Xaa Lys
1               5                   10

<210> SEQ ID NO 50
```

```
<211> LENGTH: 16
<212> TYPE: DNA
<213> ORGANISM: Artificial Sequence
<220> FEATURE:
<223> OTHER INFORMATION: Novel Sequence

<400> SEQUENCE: 50
caacttgata ttaata                                                        16

<210> SEQ ID NO 51
<211> LENGTH: 8
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(2)
<223> OTHER INFORMATION: /note= "Heterocyclic base is attached to
     N-acetyl(2-aminoethyl) glycine through the
     N-acetyl group at position 1 of the base."
<220> FEATURE:
<221> NAME/KEY: misc_feature
<222> LOCATION: (3)..(3)
<223> OTHER INFORMATION: /note= "Heterocyclic base is attached to
     N-acetyl(2-aminoethyl) glycine through the
     N-acetyl group at position 9 of the base."
<220> FEATURE:
<221> NAME/KEY: misc_feature
<222> LOCATION: (4)..(5)
<223> OTHER INFORMATION: /note= "Heterocyclic base is attached to
     N-acetyl(2-aminoethyl) glycine through the
     N-acetyl group at position 1 of the base."
<220> FEATURE:
<221> NAME/KEY: misc_feature
<222> LOCATION: (6)..(6)
<223> OTHER INFORMATION: /note= "Heterocyclic base is attached to
     N-acetyl(2-aminoethyl) glycine through the
     N-acetyl group at position 9 of the base."
<220> FEATURE:
<221> NAME/KEY: misc_feature
<222> LOCATION: (7)..(7)
<223> OTHER INFORMATION: /note= "Heterocyclic base is attached to
     N-acetyl(2-aminoethyl) glycine through the
     N-acetyl group at position 1 of the base."

<400> SEQUENCE: 51

Xaa Xaa Xaa Xaa Xaa Xaa Xaa Lys
1               5

<210> SEQ ID NO 52
<211> LENGTH: 15
<212> TYPE: DNA
<213> ORGANISM: Artificial Sequence
<220> FEATURE:
<223> OTHER INFORMATION: Novel Sequence

<400> SEQUENCE: 52
acatgcagtg ttgat                                                         15

<210> SEQ ID NO 53
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(10)
<223> OTHER INFORMATION: /note= "Heterocyclic base is attached to
     N-acetyl(2-aminoethyl) glycine through the
     N-acetyl group at position 9 of the base."
```

```
<400> SEQUENCE: 53

Xaa Xaa Xaa Xaa Xaa Xaa Xaa Xaa Xaa Xaa Lys
1               5                   10

<210> SEQ ID NO 54
<211> LENGTH: 10
<212> TYPE: DNA
<213> ORGANISM: Artificial Sequence
<220> FEATURE:
<223> OTHER INFORMATION: Novel Sequence

<400> SEQUENCE: 54
aaaaggagag                                                              10

<210> SEQ ID NO 55
<211> LENGTH: 10
<212> TYPE: DNA
<213> ORGANISM: Artificial Sequence
<220> FEATURE:
<223> OTHER INFORMATION: Novel Sequence

<400> SEQUENCE: 55
gagaggaaaa                                                              10

<210> SEQ ID NO 56
<211> LENGTH: 11
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (1)..(10)
<223> OTHER INFORMATION: /note= "Heterocyclic base is attached to
      N-acetyl(2-aminoethyl) glycine through the
      N-acetyl group at position 9 of the base."

<400> SEQUENCE: 56

Xaa Xaa Xaa Xaa Xaa Xaa Xaa Xaa Xaa Xaa Lys
1               5                   10

<210> SEQ ID NO 57
<211> LENGTH: 10
<212> TYPE: DNA
<213> ORGANISM: Artificial Sequence
<220> FEATURE:
<223> OTHER INFORMATION: Novel Sequence

<400> SEQUENCE: 57
aagaagaaaa                                                              10

<210> SEQ ID NO 58
<211> LENGTH: 10
<212> TYPE: DNA
<213> ORGANISM: Artificial Sequence
<220> FEATURE:
<223> OTHER INFORMATION: Novel Sequence

<400> SEQUENCE: 58
aaaaagaaaa                                                              10

<210> SEQ ID NO 59
<211> LENGTH: 10
<212> TYPE: DNA
<213> ORGANISM: Artificial Sequence
<220> FEATURE:
<223> OTHER INFORMATION: Novel Sequence
```

<400> SEQUENCE: 59
aaaaaaaaaa                                                        10

<210> SEQ ID NO 60
<211> LENGTH: 22
<212> TYPE: DNA
<213> ORGANISM: Artificial Sequence
<220> FEATURE:
<223> OTHER INFORMATION: Novel Sequence

<400> SEQUENCE: 60
ggatccaaaa aaaaaaggat cc                                          22

<210> SEQ ID NO 61
<211> LENGTH: 22
<212> TYPE: DNA
<213> ORGANISM: Artificial Sequence
<220> FEATURE:
<223> OTHER INFORMATION: Novel Sequence

<400> SEQUENCE: 61
ggatcctttt tttttggat cc                                           22

<210> SEQ ID NO 62
<211> LENGTH: 24
<212> TYPE: DNA
<213> ORGANISM: Artificial Sequence
<220> FEATURE:
<223> OTHER INFORMATION: Novel Sequence

<400> SEQUENCE: 62
ctgcagaaga agaaaactgg gcag                                        24

<210> SEQ ID NO 63
<211> LENGTH: 22
<212> TYPE: DNA
<213> ORGANISM: Artificial Sequence
<220> FEATURE:
<223> OTHER INFORMATION: Novel Sequence

<400> SEQUENCE: 63
ctgcagtttt cttcttctgc ag                                          22

<210> SEQ ID NO 64
<211> LENGTH: 10
<212> TYPE: DNA
<213> ORGANISM: Artificial Sequence
<220> FEATURE:
<223> OTHER INFORMATION: Novel Sequence

<400> SEQUENCE: 64
ttttcttctt                                                        10

<210> SEQ ID NO 65
<211> LENGTH: 10
<212> TYPE: DNA
<213> ORGANISM: Artificial Sequence
<220> FEATURE:
<223> OTHER INFORMATION: Novel Sequence

<400> SEQUENCE: 65
aagaagaaaa                                                        10

<210> SEQ ID NO 66

```
<211> LENGTH: 10
<212> TYPE: DNA
<213> ORGANISM: Artificial Sequence
<220> FEATURE:
<223> OTHER INFORMATION: Novel Sequence

<400> SEQUENCE: 66
ttcttctttt                                                            10

<210> SEQ ID NO 67
<211> LENGTH: 9
<212> TYPE: DNA
<213> ORGANISM: Artificial Sequence
<220> FEATURE:
<223> OTHER INFORMATION: Novel Sequence

<400> SEQUENCE: 67 aaaagaaaa                                                              9

<210> SEQ ID NO 68
<211> LENGTH: 16
<212> TYPE: DNA
<213> ORGANISM: Artificial Sequence
<220> FEATURE:
<223> OTHER INFORMATION: Novel Sequence

<400> SEQUENCE: 68
gggggggaaa aaaaaa                                                     16

<210> SEQ ID NO 69
<211> LENGTH: 10
<212> TYPE: DNA
<213> ORGANISM: Artificial Sequence
<220> FEATURE:
<223> OTHER INFORMATION: Novel Sequence

<400> SEQUENCE: 69
cccttcctcc                                                            10

<210> SEQ ID NO 70
<211> LENGTH: 10
<212> TYPE: DNA
<213> ORGANISM: Artificial Sequence
<220> FEATURE:
<223> OTHER INFORMATION: Novel Sequence

<400> SEQUENCE: 70
gggaaggagg                                                            10

<210> SEQ ID NO 71
<211> LENGTH: 10
<212> TYPE: DNA
<213> ORGANISM: Artificial Sequence
<220> FEATURE:
<223> OTHER INFORMATION: Novel Sequence

<400> SEQUENCE: 71
tctctctctt                                                            10

<210> SEQ ID NO 72
<211> LENGTH: 10
<212> TYPE: DNA
<213> ORGANISM: Artificial Sequence
<220> FEATURE:
<223> OTHER INFORMATION: Novel Sequence

<400> SEQUENCE: 72
```

```
agagagagaa                                                        10

<210> SEQ ID NO 73
<211> LENGTH: 15
<212> TYPE: DNA
<213> ORGANISM: Artificial Sequence
<220> FEATURE:
<223> OTHER INFORMATION: Novel Sequence

<400> SEQUENCE: 73
tgaacgtcac aacta                                                  15

<210> SEQ ID NO 74
<211> LENGTH: 15
<212> TYPE: DNA
<213> ORGANISM: Artificial Sequence
<220> FEATURE:
<223> OTHER INFORMATION: Novel Sequence

<400> SEQUENCE: 74
tagttgagtc gtaca                                                  15

<210> SEQ ID NO 75
<211> LENGTH: 15
<212> TYPE: DNA
<213> ORGANISM: Artificial Sequence
<220> FEATURE:
<223> OTHER INFORMATION: Novel Sequence

<400> SEQUENCE: 75
tgtacgtcac aacta                                                  15

<210> SEQ ID NO 76
<211> LENGTH: 15
<212> TYPE: RNA
<213> ORGANISM: Artificial Sequence
<220> FEATURE:
<223> OTHER INFORMATION: Novel Sequence

<400> SEQUENCE: 76
uaguugugac guaca                                                  15

<210> SEQ ID NO 77
<211> LENGTH: 50
<212> TYPE: DNA
<213> ORGANISM: Artificial Sequence
<220> FEATURE:
<223> OTHER INFORMATION: Novel Sequence

<400> SEQUENCE: 77
ccatcttcct gctaatttta aaagaaaata tgctgtttcc tgccctgttt             50

<210> SEQ ID NO 78
<211> LENGTH: 9
<212> TYPE: DNA
<213> ORGANISM: Artificial Sequence
<220> FEATURE:
<223> OTHER INFORMATION: Novel Sequence

<400> SEQUENCE: 78 aaaagaaaa                                                          9

<210> SEQ ID NO 79
<211> LENGTH: 10
<212> TYPE: DNA
```

```
<213> ORGANISM: Artificial Sequence
<220> FEATURE:
<223> OTHER INFORMATION: Novel Sequence

<400> SEQUENCE: 79
gtagatcact                                                          10

<210> SEQ ID NO 80
<211> LENGTH: 10
<212> TYPE: DNA
<213> ORGANISM: Artificial Sequence
<220> FEATURE:
<223> OTHER INFORMATION: Novel Sequence

<400> SEQUENCE: 80
agtcatctac                                                          10

<210> SEQ ID NO 81
<211> LENGTH: 16
<212> TYPE: DNA
<213> ORGANISM: Artificial Sequence
<220> FEATURE:
<223> OTHER INFORMATION: Novel Sequence

<400> SEQUENCE: 81
tgtacgtcac aactac                                                   16

<210> SEQ ID NO 82
<211> LENGTH: 15
<212> TYPE: DNA
<213> ORGANISM: Artificial Sequence
<220> FEATURE:
<223> OTHER INFORMATION: Novel Sequence

<400> SEQUENCE: 82
tagttgtgac gtaca                                                    15

<210> SEQ ID NO 83
<211> LENGTH: 16
<212> TYPE: DNA
<213> ORGANISM: Artificial Sequence
<220> FEATURE:
<223> OTHER INFORMATION: Novel Sequence

<400> SEQUENCE: 83
caacttgata ttaata                                                   16

<210> SEQ ID NO 84
<211> LENGTH: 26
<212> TYPE: DNA
<213> ORGANISM: Artificial Sequence
<220> FEATURE:
<223> OTHER INFORMATION: Novel Sequence

<400> SEQUENCE: 84 ttttcccct gtcgacccct cttttt                                         26

<210> SEQ ID NO 85
<211> LENGTH: 22
<212> TYPE: DNA
<213> ORGANISM: Artificial Sequence
<220> FEATURE:
<223> OTHER INFORMATION: Novel Sequence

<400> SEQUENCE: 85
cctaggtttt tttttccta gg                                             22
```

```
<210> SEQ ID NO 86
<211> LENGTH: 9
<212> TYPE: DNA
<213> ORGANISM: Artificial Sequence
<220> FEATURE:
<223> OTHER INFORMATION: Novel Sequence

<400> SEQUENCE: 86 ttttctttt                                                                  9

<210> SEQ ID NO 87
<211> LENGTH: 16
<212> TYPE: DNA
<213> ORGANISM: Artificial Sequence
<220> FEATURE:
<223> OTHER INFORMATION: Novel Sequence

<400> SEQUENCE: 87 ccccccttt tttttt                                                          16

<210> SEQ ID NO 88
<211> LENGTH: 16
<212> TYPE: DNA
<213> ORGANISM: Artificial Sequence
<220> FEATURE:
<223> OTHER INFORMATION: Novel Sequence

<400> SEQUENCE: 88
aaaaaaaaag gggggg                                                         16

<210> SEQ ID NO 89
<211> LENGTH: 15
<212> TYPE: DNA
<213> ORGANISM: Artificial Sequence
<220> FEATURE:
<223> OTHER INFORMATION: Novel Sequence

<400> SEQUENCE: 89
acaugcagug uugau                                                          15
```